US011284894B2

(12) United States Patent
Park

(10) Patent No.: US 11,284,894 B2
(45) Date of Patent: Mar. 29, 2022

(54) DEVICE AND METHOD FOR ASSISTING SELECTION OF SURGICAL STAPLE HEIGHT

(71) Applicant: Chul Hi Park, Seoul (KR)

(72) Inventor: Chul Hi Park, Seoul (KR)

( * ) Notice: Subject to any disclaimer, the term of this patent is extended or adjusted under 35 U.S.C. 154(b) by 136 days.

(21) Appl. No.: 16/932,873

(22) Filed: Jul. 20, 2020

(65) Prior Publication Data

US 2021/0038221 A1 Feb. 11, 2021

Related U.S. Application Data

(60) Provisional application No. 62/883,036, filed on Aug. 5, 2019, provisional application No. 62/912,659, filed on Oct. 9, 2019, provisional application No. 62/971,161, filed on Feb. 6, 2020.

(51) Int. Cl.
*A61B 17/072* (2006.01)
*A61B 17/068* (2006.01)

(52) U.S. Cl.
CPC ........ *A61B 17/072* (2013.01); *A61B 17/0686* (2013.01); *A61B 2017/0725* (2013.01); *A61B 2560/0266* (2013.01); *A61B 2562/0261* (2013.01)

(58) Field of Classification Search
CPC .............. A61B 17/088; A61B 17/072; A61B 17/07207; A61B 17/07292; A61B 17/0644; A61B 2017/00477; A61B 2017/00017; A61B 2017/07214; A61B 2017/07271
See application file for complete search history.

(56) References Cited

U.S. PATENT DOCUMENTS

| 5,865,361 A * | 2/1999 | Milliman ............. A61B 17/072 227/176.1 |
| 9,358,003 B2 * | 6/2016 | Hall ....................... A61B 90/90 |
| 10,682,139 B2 | 6/2020 | Park |
| 2006/0151568 A1 * | 7/2006 | Weller ............... A61B 17/0218 227/175.1 |
| 2006/0273135 A1 * | 12/2006 | Beetel ............. A61B 17/07207 227/175.1 |
| 2006/0289600 A1 * | 12/2006 | Wales ............ A61B 17/320016 227/175.1 |
| 2008/0078806 A1 * | 4/2008 | Omaits ............ A61B 17/07207 227/181.1 |
| 2008/0185419 A1 * | 8/2008 | Smith .............. A61B 17/07207 227/179.1 |
| 2012/0228358 A1 * | 9/2012 | Zemlok .................. A61B 90/90 227/176.1 |
| 2012/0241499 A1 * | 9/2012 | Baxter, III ......... A61B 17/0643 227/176.1 |

(Continued)

*Primary Examiner* — Nathaniel C Chukwurah

(57) ABSTRACT

A surgical compression gauge instrument comprising a compression gauge jaw member and an anvil jaw member for measuring a reactionary force from tissue captured and compressed to a predetermined gap distance between the two jaw members is disclosed herein. The compression gauge jaw member comprises a force gauge assembly for measuring the tissue reactionary force, and a spacer assembly for holding the two jaw members at a predetermined gap distance, which comprises an adjustable spacer member and a stopper for providing a positive stop to the adjustable spacer member. The spacer assembly is configured to selectively adjust the gap distance between the two jaw members.

17 Claims, 59 Drawing Sheets

(56) References Cited

U.S. PATENT DOCUMENTS

| | | | | |
|---|---|---|---|---|
| 2013/0256375 A1* | 10/2013 | Shelton, IV | ....... | A61B 17/0643 227/176.1 |
| 2014/0001230 A1* | 1/2014 | Soltz | .................... | A61B 17/072 227/175.1 |
| 2015/0209035 A1* | 7/2015 | Zemlok | ................ | G01D 18/008 73/1.01 |
| 2015/0316431 A1* | 11/2015 | Collins | .................. | A61B 90/98 606/219 |

* cited by examiner

DEVICE AND METHOD FOR ASSISTING SELECTION OF SURGICAL STAPLE HEIGHT

CROSS REFERENCE TO RELATED APPLICATIONS

The present application claims the benefit of and priority to U.S. Provisional Patent Applications No. 62/883,036, filed on Aug. 5, 2019, No. 62/912,659, filed on Oct. 9, 2019 and No. 62/971,161, filed on Feb. 6, 2020, the entire contents of which are incorporated by reference herein.

The present application is related to U.S. patent application Ser. No. 16/852,464, filed on Apr. 18, 2020, which is a Continuation application of U.S. patent application Ser. No. 15/893,638, filed on Feb. 11, 2018, now U.S. Pat. No. 10,682,139, the entire contents of which are incorporated by reference herein.

TECHNICAL FIELD

The present invention relates to a medical device and method for use in surgical procedures. More particularly, the present invention relates to a surgical device and method for assisting selection of surgical staple height in a surgical stapling operation.

BACKGROUND OF THE INVENTION

The utilization of mechanical tissue fastening instruments, notably, open and endoscopic surgical staplers have been increasing steadily in recent years as a substitute for suturing in joining a tissue, joining and cutting a tissue simultaneously and performing anastomosis of tubular organs belonging to the digestive system in a number of surgical disciplines. Over the years these instruments have proven to provide significant clinical benefits of improved patient outcome in addition to procedural benefits of reduced procedure time and simplified surgical tasks when compared to laborious and time consuming suturing, and related cost savings. In certain types of surgical procedures use of surgical staplers has become the preferred method of joining a tissue including the bariatric, thoracic and colorectal surgeries.

There are several known types of surgical stapler instruments specifically adapted for use in various procedures such as end-to-end anastomosis, gastrointestinal anastomosis, endoscopic gastrointestinal anastomosis, and transverse anastomosis. Examples of stapler instruments for these various procedures can be found in U.S. Pat. Nos. 5,915, 616; 6,202,914; 5,865,361; and 5,964,394, which are each herein incorporated by reference.

Known endoscopic surgical stapler instruments comprise a handle and an end effector that are fixedly attached to either ends of an elongate shaft and operatively engaged with each other. An end effector simultaneously makes a longitudinal incision in tissue and applies lines of staples on opposing sides of the incision. An end effector includes a pair of opposed jaw members that, if the instrument is intended for endoscopic or laparoscopic applications, are capable of passing through a cannula passageway. One of the jaw members, often referred to as a cartridge jaw member, receives a staple cartridge having at least two laterally spaced rows of staples in an elongate cartridge channel or a cartridge bay. The other jaw member, often referred to as an anvil jaw member, defines an anvil having staple-forming pockets aligned with the rows of staples in the staple cartridge. The instrument commonly includes a plurality of reciprocating wedges which, when driven distally, pass through openings in the staple cartridge and engage drivers supporting the staples to effect the firing of the staples toward the anvil.

In surgical stapling operation a physician operator first positions the end effector of a surgical stapler instrument to capture a target tissue between the two jaw members in open position and then operates the handle to close the two jaw members to clamp and compress the target tissue to a nominal thickness defined by the gap distance between the tissue contacting surfaces of the staple cartridge and the anvil prior to the firing of the staples. In the designs of presently available stapler instruments a physician has no means to control the degree or force of target tissue compression but is presented with a set of standardized staple cartridges colored coded according to the formed height(s) of staples contained therein, which correlates with the gap distance between the tissue contacting surfaces of the stale cartridge and anvil. Presently, the standardized set of staple cartridges, typically color coded white, blue, gold, green and black in the ascending order of staple heights contained therein, includes staples with formed heights between 1 mm and 2.3 mm in discrete increment. There are also in the market a set of staple cartridges, each cartridge containing a combination staples of varying heights with its own unique color coding tailored for application on tissue with varying compressed thickness. In compressing the target tissue the two jaw members comprising the end effector of stapler instrument are subject to a distributed reactionary load from the compressed tissue usually resulting in deflection of the two jaw members increasing progressively along the length thereof going from the proximal to distal end and more so, in the anvil than in the cartridge jaw member which is more substantial and structurally rigid. The corresponding variation in the gap distance between the tissue contacting surfaces of the staple cartridge and the anvil makes the tissue compression non-uniform decreasing progressively going from the proximal to distal ends of the end effector.

The level of tissue compression is one of the key factors that determine success of a surgical stapling operation often defined by adequate hemostasis and minimal damage of tissue along the staple line, and leak-free sealing of the target tubular organ among other considerations. It is known that a desirable clinical outcome of a surgical stapling operation is most likely achieved when the target tissue is compressed to a compression force between 6 g/mm$^2$ or 8 g/mm$^2$. Since present surgical stapler technology does not provide means to control the compression force of the target tissue a physician needs to choose a staple cartridge out of a standard set that would best approximate the optimal compression force for the target tissue when the two jaw members are closed with the chosen staple cartridge mounted in the cartridge bay. Having no practical means to help direct selection of staple cartridge, for example, accessory tools to directly assess a key mechanical property or condition of the target tissue, a physician is left to rely solely on his or her experience, or educated guess in selecting a staple cartridge, which leaves open possibility of under- or over-compression of the target tissue. Under-compression of tissue could lead to inadequate hemostasis and potential leakage of content contained within the tissue while over-compression to tearing of tissue or ischemia requiring prolonged period of healing. The staple cartridge selection is particularly difficult for a target tissue belonging to an organ with naturally occurring, large thickness variation such as in the stomach or an organ with unknown variation in mechanical properties such as in the lung at different disease state.

Manufacturers of present surgical stapler instruments instruct a physician to verify the adequacy of selected staple cartridge in compressing a target tissue by the feedback force felt in the hand operating the handle of the stapler instrument to apply the tissue compression. The instructions basically say to switch to a new staple cartridge with staples of larger formed height if it is overly difficult to operate the handle to apply compression to the target tissue specifically to guard against over-compression. This method is proven to be hardly practical in the field because the feedback force felt in the palm of the physician's hand may not necessarily correlates with the level of tissue compression due to the facts that the feedback force may be distorted being passed down through mechanical linkages and joints comprising the operating mechanism for the end effector and that the two jaw members comprising the end effector undergoes deflection caused by the reactionary load from the compressed tissue. In addition a unit of change in the compressed tissue thickness represented by the standard set of staple cartridges typically corresponds to only around few tens of gram of force in tissue compression which is barely discernible by the haptic sense felt in the palm of the hand alone even under the best of circumstances. Corresponding instruction for staple cartridge selection for preventing under-compression of a target tissue does not even exist.

U.S. Pat. No. 8,893,946 to Boudreaux et al., which is herein incorporated by reference, describes a surgical instrument that includes components for measuring the thickness of a tissue clamped between the two jaw members of an end effector thereof relying on a strain gauge or strain gauges as a means to generate a signal or signals corresponding to the tissue thickness and/or a compression load applied to the tissue. This disclosure describes the strain gauges as being used stand-alone but fails to describe how the strain gauges are practically implemented, for example, in the form of a load cell, well known to those of skill in the art, to generate such signals that could be converted to the thickness of tissue or the compression load acting thereon. The surgical instrument in this disclosure does not include any means to prevent or compensate for the potential deflection of a jaw member comprising an end effector as a result of a reactionary load from the compressed tissue nor for the effect of the play present in the closure mechanism of the two jaw members comprising the end effector on the tissue thickness measurement. This disclosure also fails to define the thickness of the clamped tissue in such sufficient detail for it to be of practical use in the selection of a staple cartridge for a stapling operation on the tissue.

Therefore, significant needs exist for a surgical device and method that would aid a physician in selecting a staple cartridge from the standard set of staple cartridges.

BRIEF SUMMARY OF THE INVENTION

The present invention is directed toward a surgical device and method for use in surgical procedures. More particularly, the present invention relates to a surgical device and method for assisting selection of a staple cartridge from the standard set of staple cartridges optimal for a target tissue of a surgical stapling operation.

To address the foregoing needs and with other objects in view there are provided, in accordance with the present invention, a surgical device for enabling a surgical stapler instrument to compress a tissue consistently to a predetermined thickness and measure a reactionary load therefrom and a method for assisting a physician in selecting a staple cartridge optimal for a tissue of a surgical stapling operation.

In a preferred embodiment of the present invention, a compression gauge cartridge for use mounted in a cartridge bay of a cartridge jaw member comprising an end effector, together with an anvil jaw member having a tissue contacting surface, of a surgical stapler instrument to compress a tissue consistently to a predetermined thickness and measure a reactionary load therefrom for assisting selection of a staple cartridge and assessing the condition of the tissue comprises: a cartridge body having a proximal end and a distal end, and a tissue supporting surface, wherein said cartridge body is configured for said compression gauge cartridge to be releasably mounted in said cartridge bay and for said tissue supporting surface to be at least at a predetermined distance from said tissue contacting surface of said anvil jaw member when said cartridge jaw member and said anvil jaw member are in a fully closed position; a force gauge assembly comprising a force transducer and a compression head having a tissue compression face, wherein said force gauge assembly is supported by said cartridge body positioned between said proximal end and said distal end thereof and wherein said compression head is configured and disposed so that said tissue compression face thereof lies substantially closer to said tissue contacting surface of said anvil jaw member than said tissue supporting surface of said cartridge body; and a spacer member extending from said tissue supporting surface of said cartridge body, wherein said compression head comprising said force gauge assembly is positioned distally with respect to said spacer member. In an alternate embodiment said tissue supporting surface of said cartridge body may be contoured in such a way to further reduce compression of said tissue disposed between said tissue supporting surface and said tissue contacting surface when said cartridge jaw member and said anvil jaw member are in a fully closed position.

In an alternate embodiment of the present invention, a compression gauge cartridge for use mounted in a cartridge bay of a cartridge jaw member comprising an end effector, together with an anvil jaw member having a tissue contacting surface, of a surgical stapler instrument to compress a tissue so that said cartridge jaw member and said anvil jaw member come to a predetermined angular positional relationship with each other and measure a reactionary load therefrom for assisting selection of a staple cartridge comprises: a cartridge body having a proximal end and a distal end, and a tissue supporting surface, wherein said cartridge body is configured for said compression gauge cartridge to be releasably mounted in said cartridge bay and for said tissue supporting surface to be at least at a predetermined distance from said tissue contacting surface of said anvil jaw member when said cartridge jaw member and said anvil jaw member are in a fully closed position; and a force gauge assembly comprising a force transducer and a compression head having a tissue compression face, wherein said force gauge assembly is supported by said cartridge body positioned between said proximal end and said distal end thereof and wherein said compression head is configured and disposed so that said tissue compression face thereof lies substantially closer to said tissue contacting surface of said anvil jaw member than said tissue supporting surface of said cartridge body. In an alternate embodiment said tissue supporting surface of said cartridge body may be contoured in such a way to further reduce compression of said tissue disposed between said tissue supporting surface and said tissue contacting surface when said cartridge jaw member and said anvil jaw member are in a fully closed position.

In an embodiment of the present invention, a surgical stapler instrument may further include a spacer block of a predetermined height disposed at a handle comprising said surgical stapler instrument for defining a predetermined extent said handle may be operated to close a cartridge jaw member and an anvil jaw member comprising an end effector comprising said surgical stapler instrument so that said cartridge jaw member and said anvil jaw member come to a predetermined angular positional relationship with each other.

In a preferred embodiment of the present invention, a surgical compression gauge instrument for compressing a tissue consistently to a predetermined thickness and measuring a reactionary load therefrom for assisting selection of a staple cartridge and assessing the condition of the tissue comprises: a handle portion; a body portion extending distally from said handle portion and defining a longitudinal axis; and a tool assembly disposed at a distal end of and operatively connected to said body portion, and comprising a compression gauge jaw member having a proximal end and a distal end and a tissue supporting surface, and an anvil jaw member having a tissue contacting surface, wherein said compression gauge jaw member is configured for said tissue supporting surface thereof to be at least at a predetermined distance from said tissue contacting surface of said anvil jaw member when said compression gauge jaw member and said anvil jaw member are in a fully closed position, and configured to open and close when operated by said handle portion, wherein said compression gauge jaw member comprises a force gauge assembly, supported therein and positioned between said proximal end and said distal end thereof, comprising a force transducer and a compression head having a tissue compression face, wherein said compression head is configured and disposed so that said tissue compression face thereof lies substantially closer to said tissue contacting surface of said anvil jaw member than said tissue supporting surface of said compression gauge jaw member; and a spacer member extending from said tissue supporting surface of said compression gauge jaw member, wherein said compression head comprising said force gauge assembly is positioned distally with respect to said spacer member.

In a preferred embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from the standard set of staple cartridges containing staples of a height corresponding to said predetermined thickness of said compressed tissue if the result of comparison is case (1), or a staple cartridge containing staples of a height smaller than said predetermined thickness of said compressed tissue taking into account said size of difference if the result of comparison is case (2), or a staple cartridge containing staples of a height larger than said predetermined thickness of said compressed tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined average height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to an average height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from said standard set of staple cartridges containing staples of an average height corresponding to said predetermined thickness of said compressed tissue if the result of comparison is case (1), or a staple cartridge containing staples of an average height smaller than said predetermined thickness of said compressed tissue taking into account said size of difference if the result of comparison is case (2), or a staple cartridge containing staples of an average height larger than said predetermined thickness of said compressed tissue taking into account said size of difference if the result of comparison is case (3). In an alternate embodiment, a method for selecting a staple cartridge from the standard set of staple cartridges, each containing staples of a predetermined average height, optimal for a tissue of a surgical stapling operation may further comprise a step of waiting for a predetermined length of time after closing said cartridge jaw member and said anvil jaw member to compress said tissue.

In another alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a green cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value; selecting a green cartridge from the standard set of staple cartridges if the result of comparison is case (1) or a blue cartridge if the result of comparison is case (2), or a black cartridge if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; providing a reference tissue for which an optimal staple height for a surgical stapling operation is known; comparing said reactionary load reading with a reactionary load from said reference tissue compressed to said predetermined thickness over the same area of said reference tissue as that of said tissue compression face of said compression head to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member having a tissue contacting surface, of a surgical stapler instrument; capturing a tissue between said cartridge jaw member and said anvil jaw member; closing said cartridge jaw member and said anvil jaw member to compress said tissue captured there-between so that said cartridge jaw member and said anvil jaw member come to a predetermined angular positional relationship with each other; reading out a reactionary load from said compressed tissue displayed on a force transducer indicator; providing a reference tissue for which an optimal staple height for a surgical stapling operation is known; comparing said reactionary load reading with a reactionary load from said reference tissue compressed so that said cartridge jaw member and said anvil jaw member come to said predetermined angular positional relationship with each other to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In order to make an informed selection of a staple cartridge for a tissue of a surgical stapling operation or to assess a condition of a tissue in a surgery, a physician mounts a compression gauge cartridge of the present invention in a cartridge bay of a cartridge jaw member of a surgical stapler instrument prepared to be used for the stapling operation or employ a dedicated surgical instrument with a tool assembly, a jaw member of which is instrumented with a compression gauge device including a force gauge assembly and a spacer member. The physician then operates the handle portion of the surgical stapler instrument or the dedicated surgical instrument to capture a tissue between the two jaw members comprising the end effector or a tool assembly and close the two jaw members to compress the tissue to a predetermined thickness set by the spacer member comprising the compression gauge cartridge or the compression gauge device. The surgical stapler instrument instrumented with the compression gauge cartridge and the dedicated surgical instrument instrumented with the compression gauge device is capable of providing a predetermined gap distance consistently and with a high degree of repeatability between the tissue compression face of the compression head comprising the force gauge assembly and the tissue contacting surface of the anvil jaw member. The compression of tissue takes place over the area covered by the tissue compression face of the compression head, which reduces the tissue to a predetermined thickness corresponding to the predetermined gap distance. Preferably, the predetermined thickness of the compressed tissue is the formed height of staples contained in a green staple cartridge from the standard set of staple cartridges. The compression head transfer a reactionary load from the compressed tissue exerted thereon to the force transducer comprising the force gauge assembly, which is displayed on a force transducer indicator connected to the force transducer comprising the force gauge assembly. Comparing the reactionary load with a known optimal tissue compression force for a surgical stapling operation the physician may decide to choose a green staple cartridge or other staple cartridges, blue or black, containing staples of a height smaller or larger than the green cartridge in the standard set of staple cartridges. Preferably, the control program for the force transducer indicator includes a software function for performing the comparison of the measured reactionary load with a set of values stored in the internal memory to provide a signal indicating a recommendation on the staple cartridge selection, for example, in the form of a color coded signal lights or other easily recognizable forms.

The presently disclosed compression gauge cartridge and method, together with attendant advantages, will be more clearly illustrated below by the description of the drawings and the detailed description of the embodiments.

BRIEF DESCRIPTION OF THE DRAWINGS

The following exemplary figures are provided to supplement the description below and more clearly describe the invention. In the figures, like elements are generally designated with the same reference numeral for illustrative convenience and should not be used to limit the scope of the present invention.

DETAILED DESCRIPTION OF THE INVENTION

Figure 1:
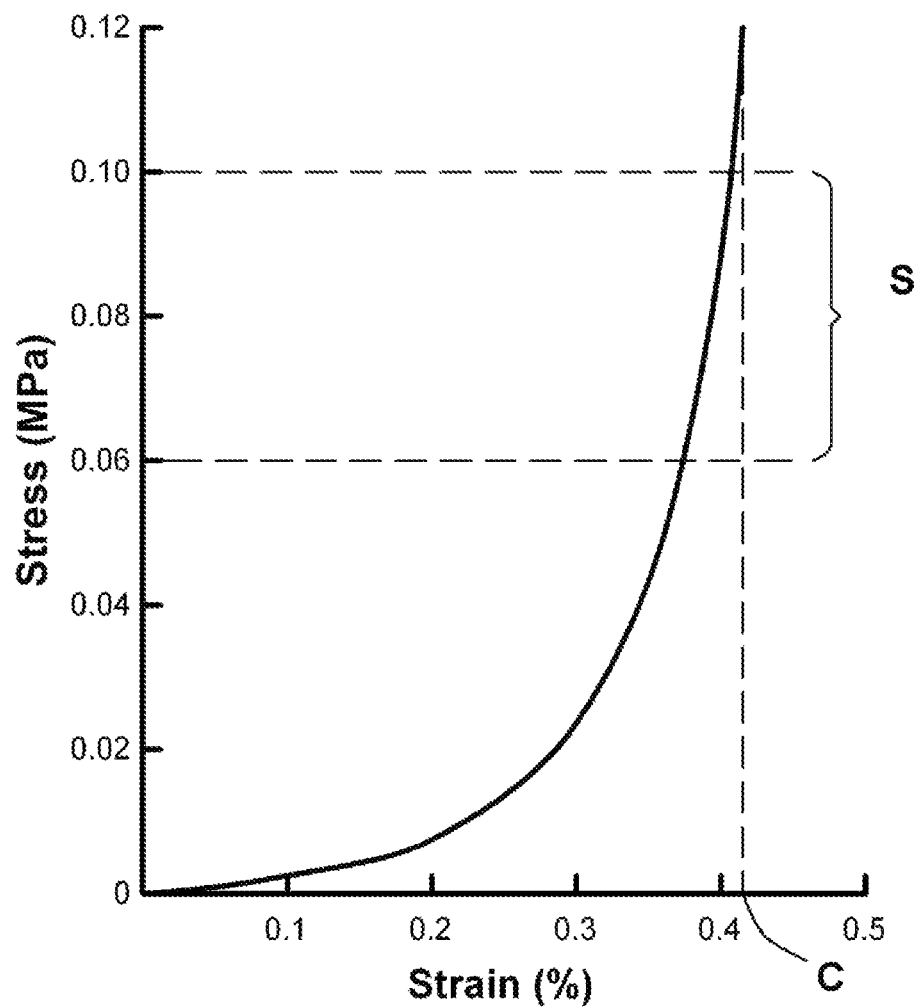
FIG. 1 is a plot of a stress-strain curve of a stomach tissue according to an embodiment of the present invention.

The novel features of the present invention will become apparent to those of skill in the art upon examination of the following detailed description of the invention. It should be understood, however, that the detailed description of the invention and the specific examples presented, while indicating certain embodiments of the present invention, are provided for illustration purposes only because various changes and modifications within the spirit and scope of the invention will become apparent to those of skill in the art from the detailed description of the invention and claims that follow.

Embodiments of the presently disclosed surgical device will now be described in detail with reference to the drawing figures wherein like reference numerals identify similar or identical elements. In the drawings and in the description which follows, the term "proximal", as is traditional, will refer to the end of the surgical device which is closest to a physician while the term "distal" will refer to the end of the device which is furthest from a physician. However, surgical instruments are used in many orientations and positions, and these terms are not intended to be limiting and absolute. The terms "force", "load", and "force load" may be used interchangeably herein to describe various mechanical forces including a reaction thereto. It should be appreciated that spatial terms such as vertical, horizontal, right, left or above, etc., are given herein with reference to the figures. In actual practice, however, a surgical device or instrument may be oriented at various angles and, as such, these spatial terms are used relative to the surgical device or instrument.

The present invention relates to a surgical device and method for use in a surgical procedure. More particularly, the present invention relates to a surgical device for enabling compression of a tissue consistently to a predetermined thickness with a high degree of repeatability and measurement of a reactionary load from the compressed tissue to assist in the selection of a staple cartridge from the standard set of staple cartridges optimal for the tissue of a surgical stapling operation and to assess a condition of a tissue of a surgical operation in a surgical procedure. In an embodiment a surgical device of the present invention may be advantageously adapted for use, as an add-on accessory, mounted in a cartridge bay comprising a cartridge jaw member of an end effector of an endoscopic surgical stapler instrument. A surgical device of the present invention may be configured to include retention features similar to a staple cartridge for releasably mounting in an open cartridge bay, if available in a surgical stapler instrument, or otherwise fixedly integrated with a cartridge jaw member of a disposable reload unit found in certain surgical stapler instruments in the market. Advantages of a surgical device of the present invention implemented as an add-on accessory to existing surgical stapler instrument include a reduced cost of use and ease of use to a physician who is already familiar with the operation of such surgical stapler instrument. In an alternate embodiment a surgical device of the present invention may be integrated with or configured as an add-on accessory to a surgical instrument dedicated to implementation of the capabilities offered by a surgical device of the present invention, which may generally comprise two opposing jaw members comprising a tool assembly, corresponding to an end effector of a surgical stapler instrument, fixedly and operably attached to a handle assembly via an elongate body and configured to open and close when operated by the handle assembly. Although the implementation and operation of a surgical device in various embodiments of the present invention will be described in the following as it relates to a endoscopic surgical stapler instrument and endoscopic surgical instrument, it should be apparent to those of skill in the art that the aspects of the present disclosure may be readily adapted for use with other surgical stapler instruments as well as other types of surgical instruments.

The present invention is being discussed in terms of endoscopic procedures and apparatus. However, use herein of terms such as "endoscopic", should not be construed to limit the present invention to a surgical instrument for use only in conjunction with an endoscopic tube (i.e., trocar). On the contrary, it is to be understood that the present invention may find use in any procedure where access is limited to a small incision, including but not limited to laparoscopic procedures, as well as open procedures.

The characteristic behavior of a tissue undergoing deformation under external stress load, for example, a compressive stress load applied by a pair of jaw members comprising an end effector of a surgical stapler instrument, has been widely studied (for example, Jacob Rosen et. al., "Biomechanical Properties of Abdominal Organs In Vivo and Postmortem Under Compression Loads," Journal of Biomedical Engineering, Vol. 130, pp. 1-17) and is generally represented by a stress-strain curve plot, well known to those of skill in the art, shown in FIG. 1 in an exemplary representation for a stomach tissue. In response to a compressive stress load, depicted in the vertical axis of the plot, the stomach tissue undergoes a rapid deformation, represented as strain, defined as a percentile reduction in tissue thickness, and depicted in the horizontal axis of the plot, in response to a relatively small change in the compressive stress load at the lower level thereof. At the higher level the stress-strain curve becomes close to a line indicating a linear elastic behavior of the stomach tissue characterized by an elastic modulus defined as the largely constant slope of the stress-strain curve. This general characteristic behavior of a stomach tissue as well as other bodily tissue under a compressive stress load is often described as a viscoelastic behavior, by those of skill in the art, exhibiting typical characteristics of both a viscous liquid and an elastic solid subject to an external compressive stress load. The initial rapid deformation of the stomach tissue at the lower level of compressive stress load is largely due to initial displacement of viscous, liquid-like components of the tissue causing a rapid reduction in thickness of the tissue under a relatively weak compressive stress load applied to an area thereof. The elastic response of the tissue at the higher level of compressive stress load is largely due to relatively immobile fibrous, solid-like components of the tissue responding to the compressive stress load collectively with substantially elastic behavior. At further higher up in the compressive stress load level the strain of the tissue reaches what is known to those of skill in the art as the ultimate tensile strength or the breaking point, labeled with a letter C in FIG. 1 where the internal structure of the tissue starts to break down and eventually completely loses ability to recoverably respond to an additional compressive stress load.

The almost linear correlation between the stress and strain of a stomach tissue and, to an extent, similar behavior exhibited in other bodily tissues at the compressive stress load interval of interest, particularly, as it relates to a surgical stapling operation, indicated by a bracket labeled with a letter S in FIG. 1, makes it possible to infer the change in the compressive stress load acting on the stomach tissue if the change in the thickness of the stomach tissue resulting therefrom is known and vice versa. Based on this observation, one could devise a practical scheme for the selection of a staple cartridge, containing staples of optimal height for a tissue of a surgical stapling operation, from the standard set of staple cartridges, which generally include steps of compressing a tissue to a predetermined thickness, i.e., to a predetermined strain; measuring a compressive stress load, i.e., a reactionary load from the compressed tissue, required to cause such reduction in thickness; comparing the measured compressive stress load to the known optimal value for a surgical stapling operation, for example, 8 g/mm² as previously described in the BACKGROUND, noting the size of difference between the measured compressive stress load and the optimal value; and based on the result of comparison, deciding whether to select a staple cartridge with staples of formed height closest to the compressed tissue thickness or of different formed heights taking into account the size of difference, i.e., change the strain induced on the tissue to a direction and level to modify the compressive stress load exerted on the tissue to be closer to the optimal value. As will be described in detail hereinafter, implementation of such a scheme on a platform of existing surgical instrument, particularly, a surgical stapler instrument may heavily rely on being able to methodically constrain the closure of the two jaw members comprising an end effector or a tool assembly to compress a tissue consistently to a predetermined thickness with a high degree of repeatability and to measure a reactionary load from the compressed tissue.

Figure 2A:
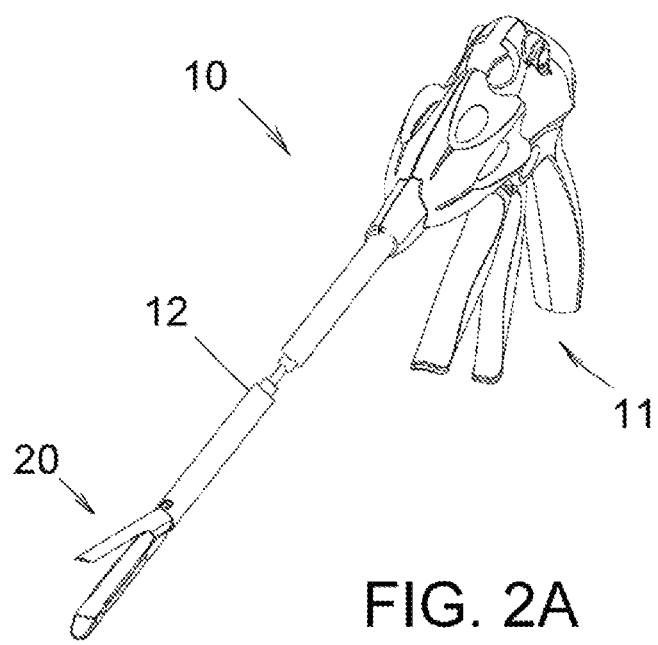
FIG. 2A is a perspective view of an exemplary surgical stapler instrument according to an embodiment of the present invention.
Figure 2B:
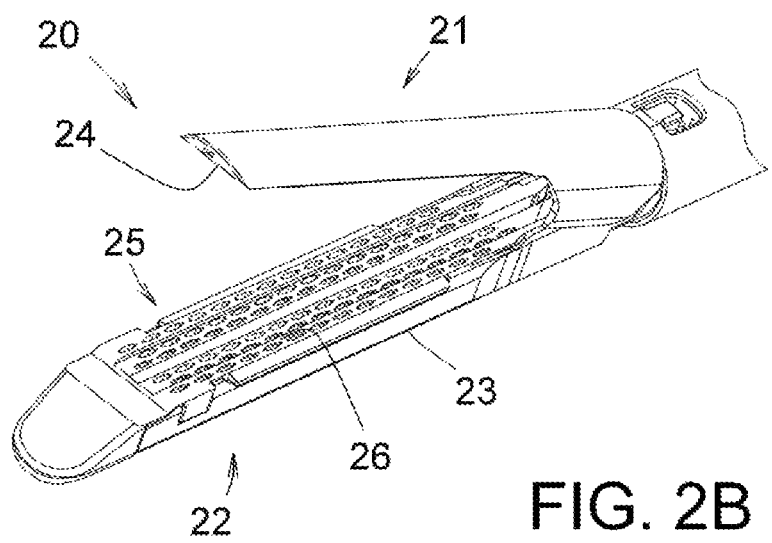
FIG. 2B is a perspective view of an end effector of an exemplary surgical stapler instrument according to an embodiment of the present invention.

Referring to FIGS. 2A and 2B, an exemplary surgical stapler instrument 10 and an enlarged view of an end effector 20 thereof are shown. Surgical stapling instrument 10 includes a handle assembly 11, end effector 20 and an elongate tube 12 that operatively connects handle assembly 11 and end effector 20 through a drive mechanism (not shown in the FIGURES). End effector 20 comprises a first jaw member 21 and a second jaw member 22. Second jaw member 22 comprises an elongate channel 23, sometimes referred to as a cartridge bay, configured to receive a staple cartridge 25 having a tissue contacting surface 26. First jaw member 21 comprises an anvil having a tissue contacting surface 24 that is aligned and pivotally engaged through a pivot mechanism (not shown) with second jaw member 22 forming a pair of opposed jaw members that open and close, when driven by the drive mechanism operated with handle assembly 11 by a physician, to capture and compress a tissue there-between for stapling. Various different drive mechanisms, well known to those of skill in the art, are employed to actuate a pivot mechanism joining two jaw members 21, 22 to cause opening and closing thereof including a drive pin and cam groove mechanism, reciprocating closure tube assemblies, gear mechanisms, rack and pinion mechanism, and pulley mechanism, etc. Typically, handle assembly 11 driving end effector 20 is configured in such a way that first and second jaw members 21, 22 are capable of rigidly holding their approximated positional relationship, i.e., a locked position, when closed to capture and compress the tissue prior to the deployment and formation of staples. Those of skill in the art would appreciate that the exemplary surgical stapler instrument depicted in the FIGURES comprises one surgical stapler instrument version with which various embodiments of a surgical device of the present invention may be advantageously employed.

The pivotal engagement between two jaw members 21, 22 comprising an end effector 20 may take various configurations including a hinge about which two jaw members 21, 22 are configured to rotate and a cam groove along which a drive pin is configured to translate to open or close end effector 20. The clearances built in the mechanical designs of the pivot mechanism and the drive mechanism to ensure smooth operations thereof and, to a lesser extent, unavoidable manufacturing tolerances in the parts thereof inevitably introduce a measurable play in the pivotal motion of two jaw members 21, 22, which manifests as an inherent uncertainty in the positional relationship between two jaw members 21, 22, particularly, in the relative angular position thereof even under unloaded condition, that is, without a tissue captured and compressed there-between. Of particular significance to a device and method in an embodiment of the present invention is a variation in the relative angular position of the two jaw members that may be appropriately referred as a backlash, i.e., a tendency for the closed jaw members to open back up, the size of which is strongly dependent on the level of compression of a tissue there-between. The variation in the backlash introduces, in effect, variability in the gap distance, defined as a distance between tissue contacting surfaces 24, 26, of two jaw members 21, 22 at a given position along the length of end effector 20, which also varies with the size of a reactionary load from the compressed tissue. The uncertainty in the gap distance due to the play in the pivot mechanism tends to become more pronounced going farther away distally from pivot mechanism due to a lever arm effect. A reactionary load from the compressed tissue acting on two jaw members 21, 22 may add to variability in the gap distance by potentially causing a deformation or a deflection of two jaw members 21, 22, more likely, an anvil the less stiffer of the two, the degree of which differs depending the size of the reactionary load and, therefore, is not easy to estimate or measure. In practice, the gap distance has been observed to vary very significantly from one tissue to another mostly due to the deflection of the anvil, irrespective of particular brands of surgical stapler instrument in the market, and in fact, there are no dedicated mechanisms implemented on the existing surgical stapler instrument products to precisely and actively control the gap distance during compression of a tissue. Instead, when critically needed, for example, in case of a very thick tissue, an external constraining means is employed to control the gap distance to some extent in certain surgical stapler instruments in the market. For this reason, a surgical stapler instrument presently being marketed does not make a suitable platform on which to implement the staple cartridge selection scheme, described previously, which hinges on an ability to compress a tissue consistently to a well defined thickness and measure a reactionary load therefrom. A surgical device and method proposed in this disclosure seeks to remedy such deficiencies in a surgical stapler instrument or a new surgical instrument dedicated for implementation of such a scheme with a mechanical and operational configuration similar to those of a surgical stapler instrument without requiring a radical redesign of the instruments by providing relatively simple features that are added-on to help bring under control the variability in the gap distance between the two jaw members comprising an end effector or a tool assembly and to introduce a capability to the instruments to measure a reactionary load from the compressed tissue as will be described hereinafter.

Figure 3A:
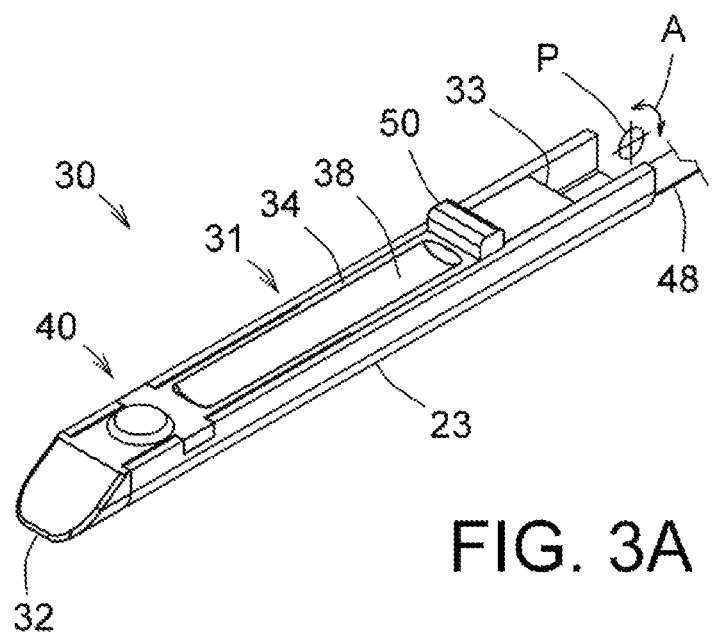
FIG. 3A is a perspective view of a compression gauge cartridge disposed in a cartridge bay of a cartridge jaw member of an end effector of an exemplary surgical stapler instrument according to an embodiment of the present invention.
Figure 3B:
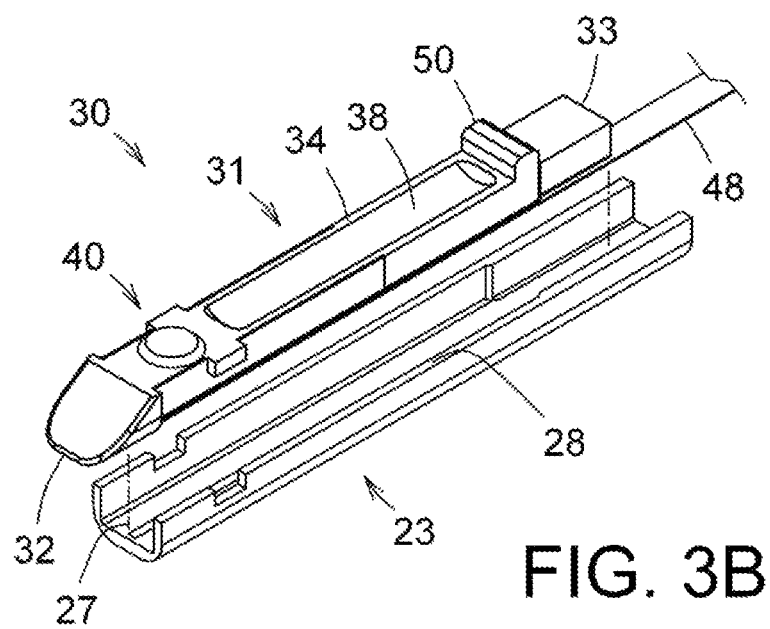
FIG. 3B is a perspective view of a compression gauge cartridge positioned spaced apart from a cartridge bay according to an embodiment of the present invention.
Figure 3C:
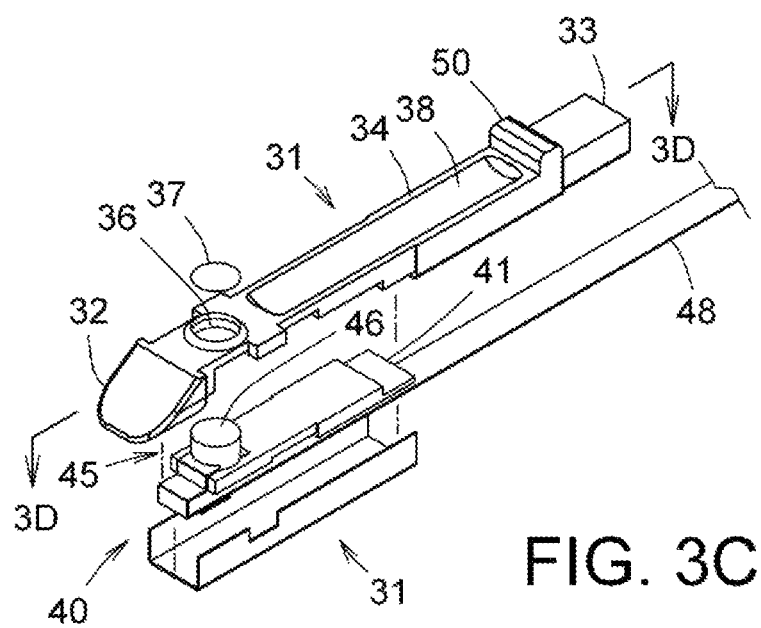
FIG. 3C is an exploded view of a compression gauge cartridge according to an embodiment of the present invention.
Figure 3D:
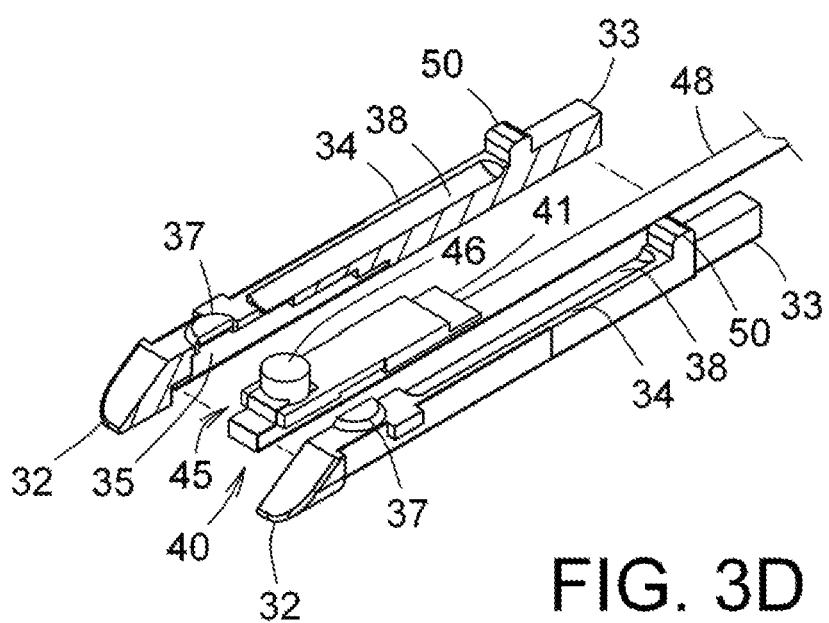
FIG. 3D is a perspective view of a compression gauge cartridge with a cartridge body sectioned along the line 3D-3D shown in FIG. 3C and spaced apart according to an embodiment of the present invention.

Referring to FIG. 3A, a compression gauge cartridge 30 is shown, in a perspective view, mounted in cartridge bay 23 of cartridge jaw member 22 of end effector 20 of surgical stapler instrument 10, as shown in FIGS. 2A and 2B, for compressing a tissue consistently to a predetermined thickness and measuring a reactionary load therefrom in an embodiment of the present invention. Anvil jaw member 21 is omitted for clarity in FIG. 3A and a pivot mechanism joining the two jaw members 21, 22 is schematically represented by a symbol labeled with a letter P and a pivotal motion by a double headed, curved arrow labeled with a letter A. In FIG. 3B compression gauge cartridge 30 is shown released from cartridge bay 23. Referring to FIG. 3C, details of construction of compression gauge cartridge 30 is shown in an exploded view in an embodiment of the present invention. In a preferred embodiment of the present invention, compression gauge cartridge 30 for use mounted in cartridge bay 23 of cartridge jaw member 22 comprising end effector 20 of surgical stapler instrument 10, together with anvil jaw member 21 having a tissue contacting surface 24, to compress a tissue consistently to a predetermined thickness and measure a reactionary load therefrom for assisting in selection of a staple cartridge optimal for a tissue of a surgical stapling operation and assessing a condition of a tissue of a surgical operation comprises: a cartridge body 31 having a proximal end 32 and a distal end 33, and a tissue supporting surface 34 corresponding to tissue contacting surface 26 of staple cartridge 25, wherein cartridge body 31 may be configured for compression gauge cartridge 30 to be releasably mounted in cartridge bay 23 and for tissue supporting surface 34 to be at least at a predetermined distance from tissue contacting surface 24 of anvil jaw member 21 when cartridge jaw member 22 and anvil jaw member 21 are in a fully closed position; a force gauge assembly 40 comprising a force transducer 41 and a compression head 45 having a tissue compression face 46, wherein force gauge assembly 40 may be supported by cartridge body 31 positioned between proximal end 32 and distal end 33 thereof, and wherein compression head 45 comprising said force gauge assembly 40 may be configured and disposed so that tissue compression face 46 thereof may lie substantially closer to tissue contacting surface 24 of anvil jaw member 21 than tissue supporting surface 34 of cartridge body 31; and a spacer member 50 extending from tissue supporting surface 34 of said cartridge body 31, wherein force gauge assembly 40 may be positioned distally with respect to spacer member 50. In an alternate embodiment tissue supporting surface 34 of cartridge body 31 may be contoured in such a way to further reduce compression of a tissue disposed between tissue supporting surface 34 and tissue contacting surface 21 when cartridge jaw member 22 and anvil jaw member 21 are in a fully closed position. Further details of compression gauge cartridge 30 can be seen in FIG. 3D showing, in a perspective view, cartridge body 31 sectioned along the line 3D-3D shown in FIG. 3C and spaced apart in an embodiment of the present invention. As will become more clear with the following description, compression gauge cartridge 30 is configured to allow an existing surgical stapler instrument to be used without modification in applying a compression to a predetermined area of a tissue captured between the two jaw members comprising an end effector thereof consistently and with a high degree of repeatability to a predetermined thickness substantially free of variations of mechanical and structural origins and measuring a reactionary load from the compressed area of the tissue dynamically throughout the compression operation. In an embodiment of the present invention cartridge body 31 comprising compression gauge cartridge 30 may be configured for compression gauge cartridge 30 to be releasably mounted and securely retained in cartridge bay 23 comprising cartridge jaw member 22 of end effector 20. In an alternate embodiment cartridge body 31 comprising compression gauge cartridge 30 may be configured to be fixedly mounted in cartridge bay 23 to be integrated with cartridge jaw member 22 of end effector 20 of surgical stapler instrument 10. In another alternate embodiment cartridge body 31 comprising compression gauge cartridge 30 may be configured to be fixedly mounted in a cartridge bay to be integrated with a cartridge jaw member of an end effector comprising a disposable reload unit of a certain surgical stapler instrument product in the market.

Figure 4A:
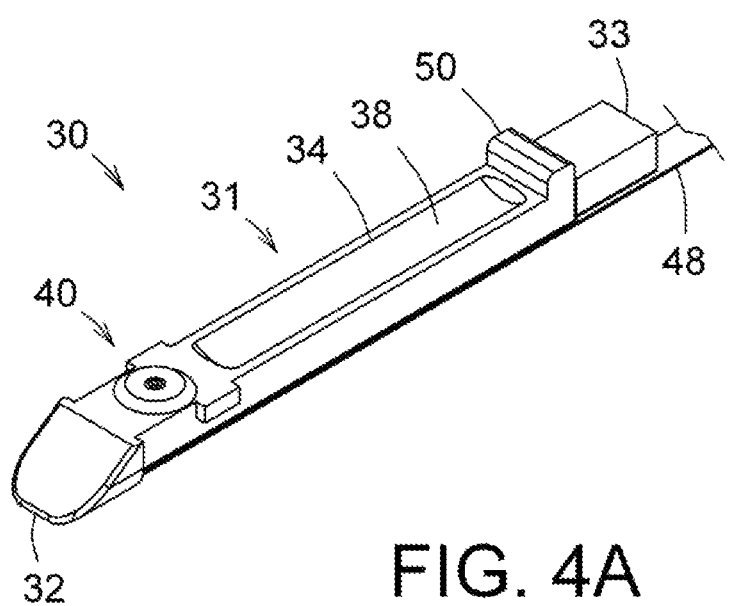
FIG. 4A is a perspective view of a compression gauge cartridge according to an alternate embodiment of the present invention.
Figure 4B:
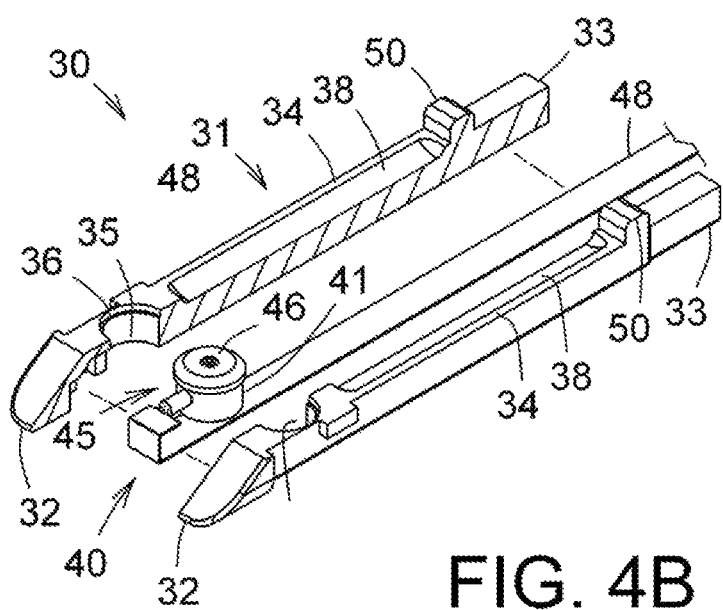
FIG. 4B is a perspective view of a compression gauge cartridge, shown in FIG. 4A, with a cartridge body sectioned similarly to that shown in FIG. 3C and spaced apart according to an alternate embodiment of the present invention.
Figure 5A:
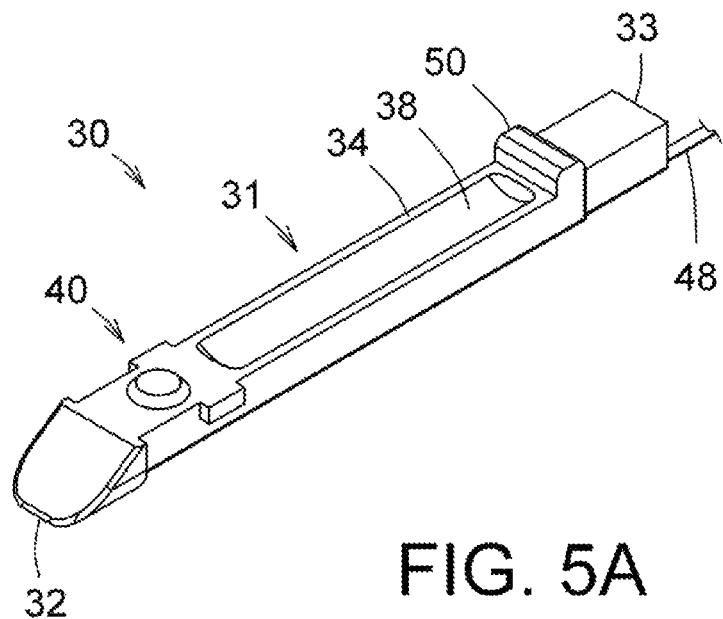
FIG. 5A is a perspective view of a compression gauge cartridge according to another alternate embodiment of the present invention.
Figure 5B:
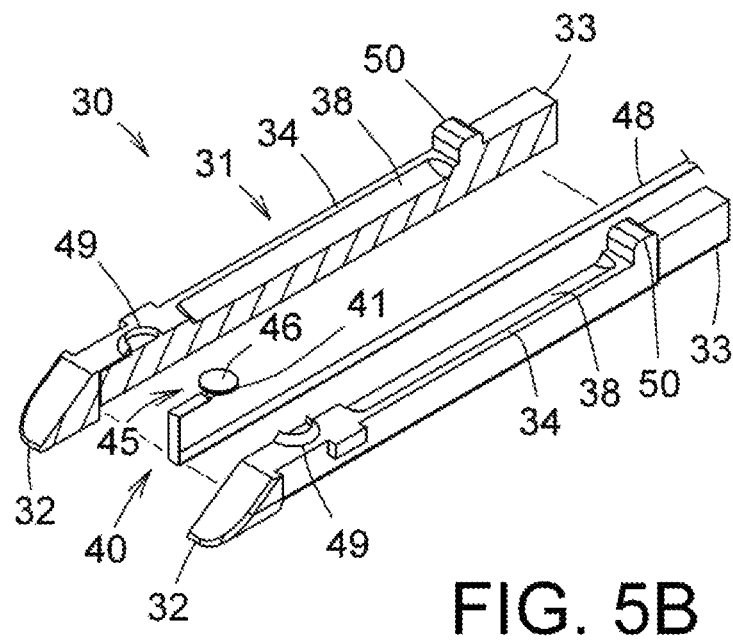
FIG. 5B is a perspective view of a compression gauge cartridge, shown in FIG. 5A, with a cartridge body sectioned similarly to that shown in FIG. 3C and spaced apart according to another alternate embodiment of the present invention.

Referring to FIGS. 3A-3D force transducer 41 comprising force gauge assembly 40 is depicted as having a configuration of a beam supported by cartridge body 31 housed in a cavity 35 therein in an embodiment of the present invention. In an alternate embodiment force transducer 41 comprising force gauge assembly 40 may have a configuration of a button supported by cartridge body 31 housed in a cavity 35 therein as shown in FIGS. 4A and 4B in similar arrangements to FIGS. 3A and 3D, respectively. In another alternate embodiment force transducer 41 comprising force gauge assembly 40 may have a substantially planar configuration supported by cartridge body 31 disposed on tissue supporting surface 34 thereof as shown in FIGS. 5A and 5B in similar arrangements to FIGS. 3A and 3D, respectively. In various embodiments of the present invention cartridge body 31 comprising compression gauge cartridge 30 provides a structurally stable platform upon which force transducer 41 relies in performing a force measurement operation exerted thereon. More detailed descriptions will follow hereinafter in a section dedicated to the force transducer.

In an embodiment of the present invention cartridge body 31 comprising compression gauge cartridge 30 may be configured to include selected design features similar to those found in a conventional staple cartridge that allow a conventional staple cartridge to be releasably mounted and securely retained in a cartridge bay of a cartridge jaw member during a stapling operation. In an alternate embodiment cartridge body 31 may include additional design features for releasable mounting and secure retention thereof in a cartridge bay and safety features for safe and effective use of a surgical stapler instrument instrumented with compression gauge cartridge 30 by a physician with average level of experience and skill in use of an ordinary surgical stapler instrument. In an embodiment, materials and method of manufacture substantially similar to those used to construct a conventional staple cartridge may be employed and appropriately adapted to manufacture cartridge body 31 comprising compression gauge cartridge 30. In an alternate embodiment cartridge body 31 may include structural reinforcements and/or unconventional construction materials, not ordinarily found in a conventional staple cartridge, to ensure proper operation of force gauge assembly 40 comprising compression gauge cartridge 30 and compression of a tissue in cooperation with an anvil jaw member comprising an end effector. As will be described hereinafter, the distribution of a reactionary load on cartridge body 31 from a tissue under compression in operation of surgical stapler instrument 10 instrumented with compression gauge cartridge 30 may be different, by design, from that on a conventional staple cartridge mounted in a cartridge bay of the same or comparable surgical stapler instrument in an embodiment of the present invention.

Referring to back FIGS. 3C and 3D, in an embodiment of the present invention cartridge body 31 may be configured to support force gauge assembly 40 in an open cavity 35 defined therein with an opening 36 disposed on tissue supporting surface 34 interconnecting cavity 35 and an external space above tissue supporting surface 34, through which compression head 45 comprising force gauge assembly 40 is disposed. In an embodiment opening 36 may be hermetically capped with a seal member 37 to prevent introduction of unwanted contaminant, such as bodily fluid, into cavity 35. Seal member 37 may be configured to be in contact with tissue compression face 46 of compression head 45 and provided with sufficient flexibility or, otherwise, a freedom of movement to allow displacement of compression head 45 in response to a load exerted thereto from a compressed tissue to take place substantially freely, which is generally very small and required in a normal operation of force transducer 41, as will be described later in a dedicated section. In an alternate embodiment seal member 37 may be integrated with compression head 45 on tissue compression face 46 thereof to substantially freely move concurrently therewith. In an embodiment cavity 35 may be configured, preferably, to substantially rigidly hold a stationary portion of force transducer 41 of a beam configuration to provide a structural support necessary for optimal operation thereof and to leave sufficient space to ensure unobstructed deflection of a deflectable portion of force transducer 41 and compression head engaged therewith, which is a key aspect of force measurement operation of a force transducer of a beam configuration, as is well known to those of skill in the art. Referring to FIG. 4B, in an embodiment of the present invention cavity 35 may be configured to accommodate to rigidly hold force transducer 41 of a button configuration and leave sufficient space for free movement of compression head 45 engaged therewith. In a further embodiment cartridge body 31 may be configured to support force gauge assembly 40 of a planar configuration substantially on tissue supporting surface 34 as shown in FIGS. 5A and 5B. In an embodiment a retention feature 49 may be provided to securely position force gauge assembly 40 on tissue supporting surface 34.

Figure 6A:
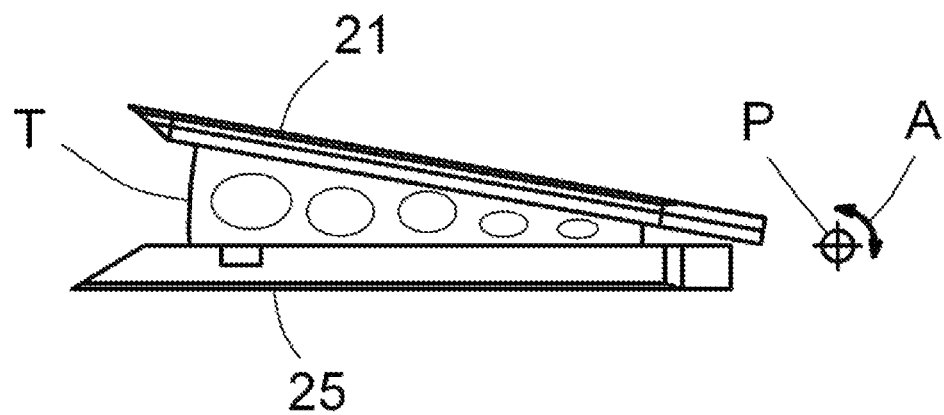
FIG. 6A is a schematic, side elevation view of a tissue captured between an anvil jaw member and a staple cartridge comprising a cartridge jaw member in an open position according to an embodiment of the present invention.
Figure 6B:
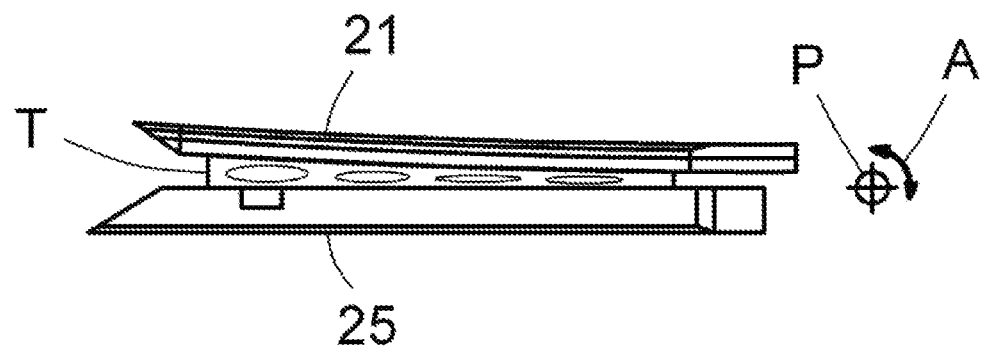
FIG. 6B is a schematic, side elevation view of a tissue compressed between an anvil jaw member and a staple cartridge in a closed position according to an embodiment of the present invention.

Referring to FIGS. 6A and 6B, schematically showing a tissue T captured and compressed, respectively, between anvil jaw member 21 and a conventional staple cartridge 25 representing a cartridge jaw member 22 as shown in FIG. 2B, the distributed reactionary load from compressed tissue T over the length of anvil jaw member 21 comprising end effector 20 often causes anvil jaw member 21 to deflect to a substantial degree typically being less stiffer than cartridge jaw member 22 instrumented with staple cartridge 25. The extent, to which anvil jaw member 21 deflects, strongly depends on the degree of compression of tissue T and gradually increases as one goes distally along the length of end effector 20 from pivot mechanism P due to a cumulative nature of the reactionary load from compressed tissue T. This is a major reason why it is not practically possible to controllably compress a tissue consistently to a known thickness with existing surgical stapler instrument mounted with a conventional stapler cartridge in a cartridge jaw member thereof in addition the inevitable plays in the pivot and drive mechanisms.

Figure 6C:
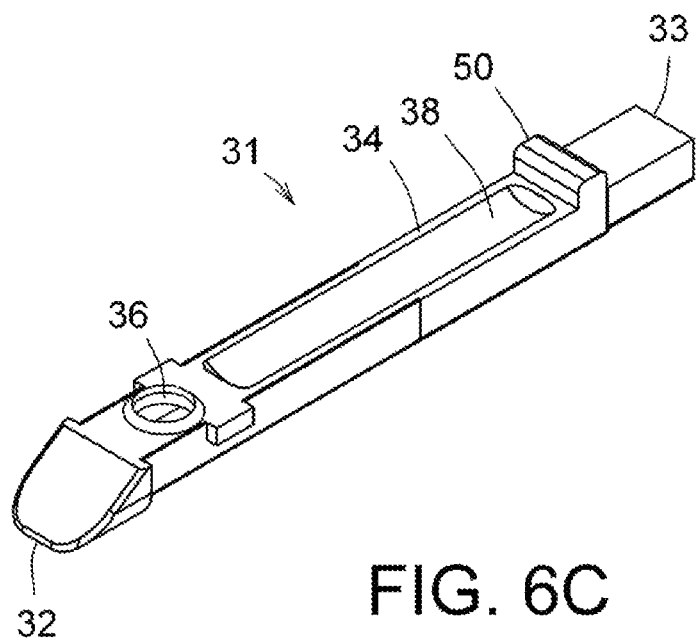
FIG. 6C is a perspective view of a cartridge body comprising a compression gauge cartridge according to an embodiment of the present invention.

With a view to substantially eliminate incontrollable deflection of an anvil jaw member, comprising an end effector together with a cartridge jaw member instrumented with a compression gauge cartridge, in performing tissue compression captured there-between, in an embodiment of the present invention, cartridge body 31, as shown in FIG. 6C in a perspective view, may be configured so that tissue supporting surface 34 thereof may be at the minimum at a predetermined distance from a tissue contacting surface of an anvil jaw member when a cartridge jaw member and an anvil jaw member are in a fully closed position with or without a tissue captured and compressed there-between. Preferably, the gap distance, defined as a distance between tissue supporting surface 34 and the tissue contacting surface of an anvil jaw member, at a position along the length of the end effector may be substantially larger than the largest gap distance provided by any one from the standard set of staple cartridges at the same position and under the same loading condition from the compressed tissue, if present, so that compression of a tissue disposed over an area covered by tissue supporting surface 34 may be minimized to substantially eliminate a distributed reactionary load acting on the anvil jaw member. In an embodiment tissue supporting surface 34 may include surface contours such as a recess 38 in order to further reduce compression applied to a tissue in contact therewith. The need to keep the tissue compression under control over the area of tissue supporting surface 34 must be balanced against the requirement for the structural stiffness of a cartridge jaw member to guard against deformation thereof. Referring back to FIG. 3B, in an embodiment of the present invention cartridge body 31 may be configured for tissue supporting surface 34 thereof to lie substantially even with a top portion 28 of cartridge bay 23. In an alternate embodiment, cartridge body 31 may be configured for tissue supporting surface 34 thereof to lie substantially above top portion 28. In another alternate embodiment, cartridge body 31 may be configured for tissue supporting surface 34 thereof to lie substantially below top portion 28.

Figure 6D:
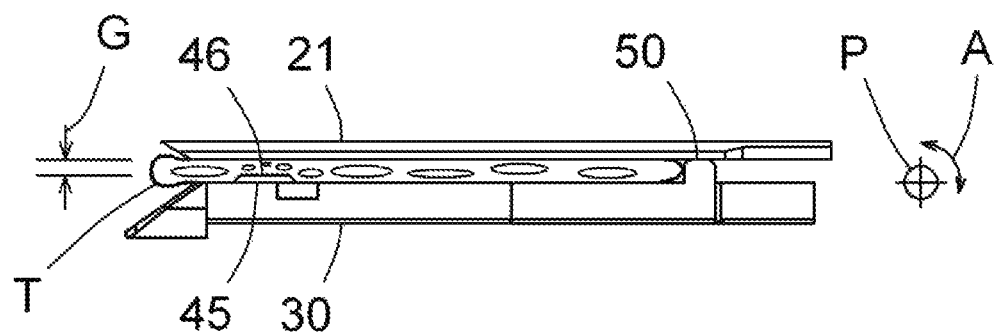
FIG. 6D is a schematic, side elevation view of a tissue compressed between a compression gauge cartridge comprising a cartridge jaw member and an anvil jaw member in a closed position according to an embodiment of the present invention.
Figure 6E:
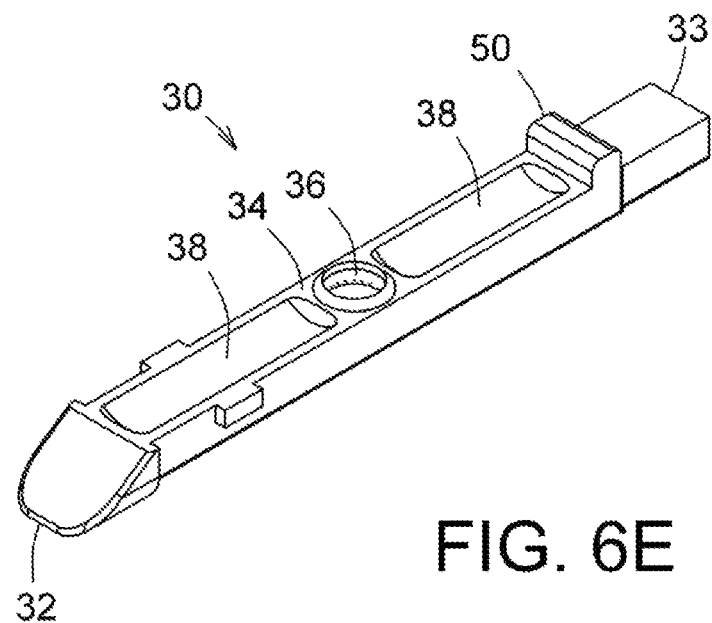
FIG. 6E is a perspective view of a cartridge body comprising a compression gauge cartridge according to an alternate embodiment of the present invention.

Located at a predetermined position along the length of cartridge body 31 on tissue supporting surface 34 thereof is an opening 36, as shown in FIGS. 3C, 3D and 4B, in an embodiment of the present invention, through which compression head 45 comprising force gauge assembly 40 is disposed. In an alternate embodiment, as shown in FIGS. 5A and 5B, force gauge assembly 40 comprising force transducer 41 of a planar configuration and compression head 45 may be disposed at a predetermined position along the length of cartridge body 31 on tissue supporting surface 34. In a preferred embodiment of the present invention compression head 45 comprising force gauge assembly 40 may be configured and disposed with respect to cartridge body 31 so that tissue compression face 46 thereof lie substantially above tissue supporting surface 34 of cartridge body 31 and closer to tissue contacting surface 24 of anvil jaw member 21, as shown in FIG. 2B, than tissue supporting surface 34 of cartridge body 31 when cartridge jaw member 22 and anvil jaw member 21 are in a fully closed position. Under such configuration, a tissue captured between a compression gauge cartridge mounted in a cartridge bay of a cartridge jaw member and an anvil jaw member experiences compression substantially exclusively over the area covered by tissue compression face 46 when two jaw members are in a fully closed position, as schematically illustrated in FIG. 6D in an embodiment, where a predetermined gap distance over tissue compression face 46 or a predetermined thickness to which a tissue is compressed is labeled by a letter G. In an embodiment of the present invention the area covered tissue compression face 46 may be varied in order to control a reactionary load from a tissue compressed thereon and substantially eliminate potential deflection of an anvil jaw member resulting therefrom. In an alternate embodiment, the position along the length of the end effector of compression head 45 comprising force gauge assembly may be varied to control a lever arm effect, as previously described, of a reactionary load from a tissue compressed thereon and substantially eliminate potential deflection of an anvil jaw member resulting therefrom as schematically shown in FIG. 6E. In another alternate embodiment, the area of tissue compression face 46 and the position along the length of the end effector of compression head 45 may be jointly varied.

Figure 7A:
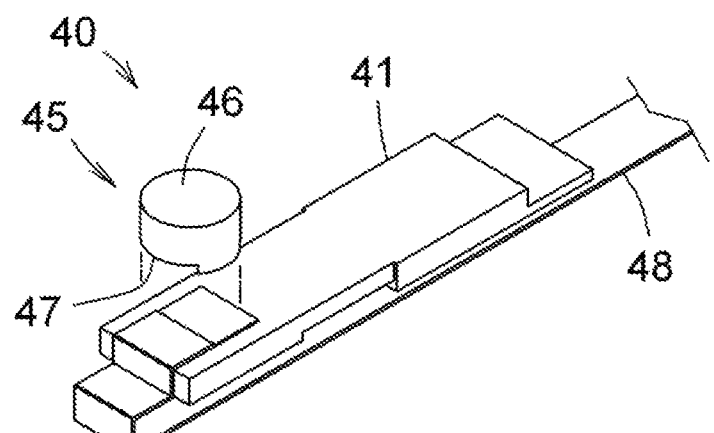
FIG. 7A is a perspective view of a force gauge assembly with a compression head set spaced apart according to an embodiment of the present invention.
Figure 8A:
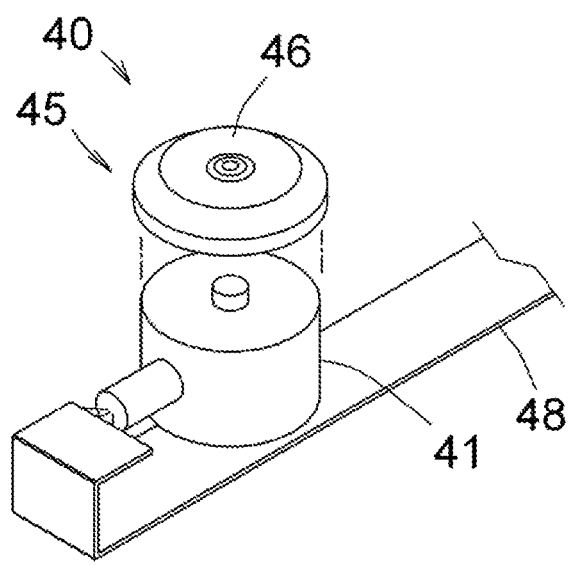
FIG. 8A is a perspective view of a force gauge assembly with a compression head set spaced apart therefrom according to an alternate embodiment of the present invention.
Figure 9A:
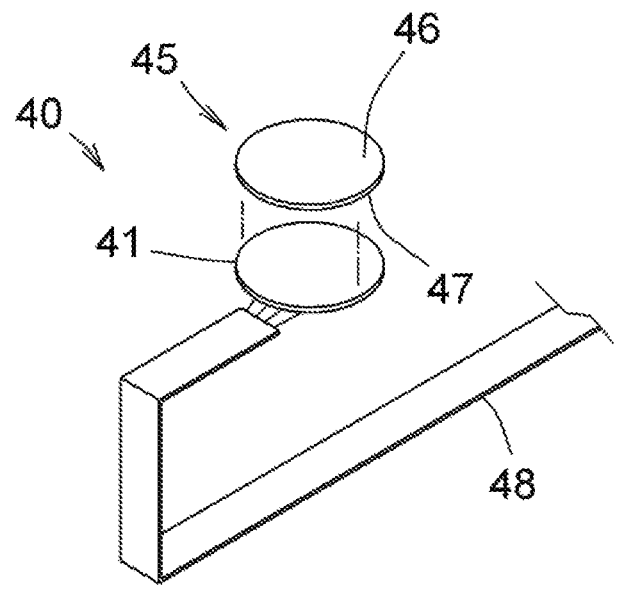
FIG. 9A is a perspective view of a force gauge assembly with a compression head set spaced apart therefrom according to another alternate embodiment of the present invention.

Referring to FIGS. 3C-4B and FIGS. 7A and 8A showing, in a perspective view, a force gauge assembly 40 comprising force transducer 41 and compression head 45 where compression head 45 is shown spaced apart from force transducer 41, in an embodiment of the present invention, force gauge assembly 40 may be disposed for compression head 45 to be located at a predetermined position along the length of cartridge body 31 between proximal end 33 and distal end 32 thereof to provide a measurement of a reactionary load from a tissue compressed in a gap between a tissue contacting surface of an anvil jaw member and tissue compression face 46 of compression head 45. In a preferred embodiment force transducer 41 may be a strain gauge based load cell of various configurations capable of generating an electrical signal when stimulated including load cells of a beam configuration including, for example, a cantilever bending beam and a parallel bending beam, as schematically illustrated in FIG. 7A, and of a button configuration, as schematically illustrated in FIG. 8A, as are well known to those of skill in the art. Strain gauge based load cells are widely available from a multitude of vendors at relatively low price levels due to their wide spread uses in industrial applications and consumer weight measurement equipments such as personal and kitchen electronic scales. In an embodiment of the present invention there is provided a signal conduction means 48 electrically connected to force transducer 41 for conducting a signal therefrom to a force transducer indicator or a controller (not shown in the FIGURES) disposed remotely from the surgical site, for example, external to a surgery patient. Appropriate signal conduction means 48 for a strain gauge based load cell and other types of load cell generating an electric signal includes a flexible flat cable and thin gauge electrical wires, both of which are widely available commercially at low cost and of such a small thickness to be able to freely pass through an annular gap between an elongate tube of a surgical stapler instrument and the inside wall of a trocar through which the instrument is deployed. In an alternate embodiment force transducer 41 may be a load cell of a planar configuration, as schematically illustrated in FIG. 9A, a piezoelectric load cell capable of generating an electrical signal when stimulated, commercially available from a multiple vendors, and a resistive film type force sensor capable of generating an electrical signal when stimulated, for example, FlexiForce Sensor® commercially available from Tekscan Inc.

Figure 7B:
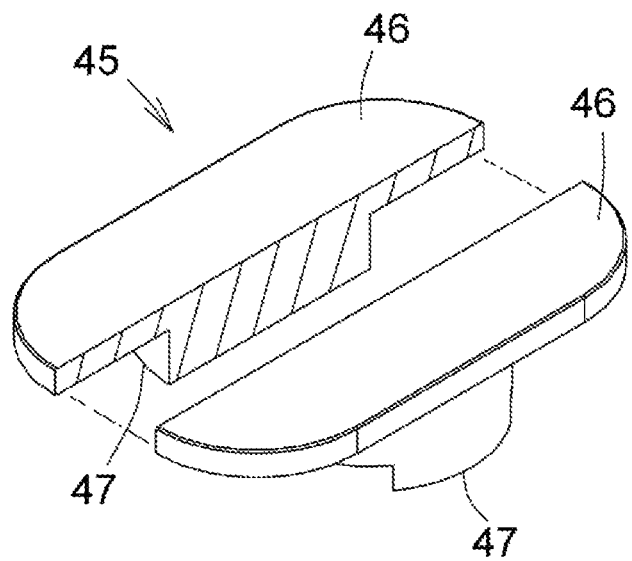
FIG. 7B is a perspective view of a compression head comprising a force gauge assembly sectioned along a long symmetry plane and spaced apart according to an alternate embodiment of the present invention.
Figure 7C:
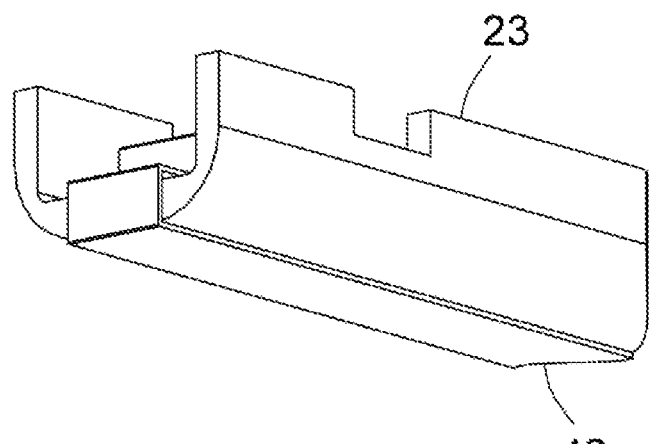
FIG. 7C is a perspective view of a signal conduction means and a cartridge jaw member partially broken away according to an embodiment of the present invention.
Figure 7D:
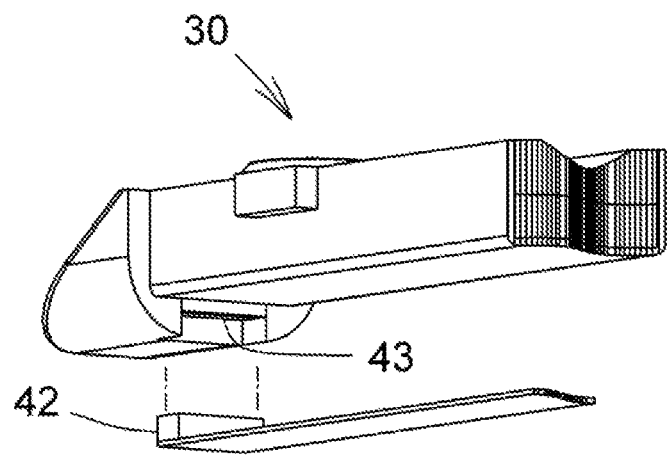
FIG. 7D is a perspective view of a signal conduction means comprising a compression gauge cartridge partially broken away according to an alternate embodiment of the present invention.

Preferably, signal conduction means 48, appropriately selected for force transducer 41, may work bi-directionally conducting a signal from force transducer 41 to a force transducer indicator or a controller disposed remotely from a surgical site for signal processing and display of result therefrom and providing a power and control signals needed for operation of force transducer. As shown in FIG. 7C, signal conduction means 48 may be routed to pass around a distal end of cartridge jaw member 23 as it exits cartridge body 31 in an embodiment of the present invention. As shown in FIG. 7D, in an alternate embodiment, signal conduction means 48 may be configured to comprise at least two parts, one part connected to force transducer 41 on one end and terminating with a connector 43 on the other end, and the other part connected to a force transducer indicator on one end and terminating to a connector 42 complementary to connector 43 on the other end. In an embodiment a force transducer indicator or a controller may be disposed externally to the patient and may include an off-the-shelf, commercial weight indicator unit, a custom designed, microprocessor controlled indicator and a signal processor electronics controlled by a computer with a display. In an alternate embodiment of the present invention, at least for a force transducer configured to be electrically powered and generate an electric signal when stimulated, an electrical power source, for example, a battery, and at least a part of processing and display circuitry may be disposed in and supported by a cartridge body comprising a compression gauge cartridge. In another alternate embodiment the cartridge body may further include a wireless communication means for wirelessly sending a signal to an indicator or a controller disposed externally from a surgical site for further processing and display.

In an embodiment, force transducer 41 may be dimensionally adaptable for use supported in a cartridge body disposed in a cartridge bay of a cartridge jaw member of an end effector. In an alternate embodiment, force transducer 41 may be dimensionally adaptable for use supported in one of the jaw members comprising an end effector of a surgical instrument dedicated to implementation of the present invention. Preferably, the deflection of a deflectable portion of force transducer 41, which normally accompanies operation of force transducer 41 in varying forms and to a different degree, at a maximum level of the reactionary load from the compressed tissue does not exceed a predetermined fraction of a strain induced on the tissue by the compression applied thereto. As previously described in reference to FIG. 1, a relatively small change in the strain of a tissue, for example, due to interaction with force transducer 41, could result in a substantial variation in the stress thereof potentially skewing the measurement of the reactionary load therefrom. Typically, a maximum deflection a strain gauge based load cell or a hydraulic load cell experiences at the load limit does not exceed a few thousandths of an inch easily satisfying the requirement for use on a tissue. A load cell of a planar configuration, at least those include in the examples described previously, does not require any deflection to perform a force measurement.

In an embodiment of the present invention, compression head 45 comprising force gauge assembly 40 mechanically interfaces between a tissue undergoing compression and force transducer 41 for measuring a reactionary force therefrom. Referring to FIGS. 3A-5B and 7A, 8A and 9A, in an embodiment compression head 45 may be configured and disposed, with respect to cartridge body 31, to contact force transducer 41 on one end, a transducer contact face 47, and the tissue on the other end, tissue compression face 46 participating in compression of the tissue cooperating with anvil jaw member 21 and transferring a reactionary load from the compressed tissue to force transducer 41 substantially without a mechanical loss in a manner conducive to the mode of operation of a particular force transducer. In an embodiment compression head 45 may be configured and disposed, with respect to cartridge body 31, so that tissue compression face 46 thereof lies substantially closer to tissue contacting surface 24 of anvil jaw member 21 than tissue supporting surface 34 of cartridge body 31 as schematically shown in FIG. 6D showing, in a side elevation view, a tissue compressed between compression gauge cartridge 30 and anvil jaw member 21 comprising an end effector in a closed position. This is to deliberately encourage the compression of a tissue to take place preferentially over an area, out of tissue contacting surface 24 of an anvil jaw member 21, covered by tissue compression face 46 and to minimize tissue compression over tissue supporting surface 34 to a predetermined gap distance between tissue compression face 46 and tissue contacting surface 24 indicated by a letter G in FIG. 6D.

Figure 8B:
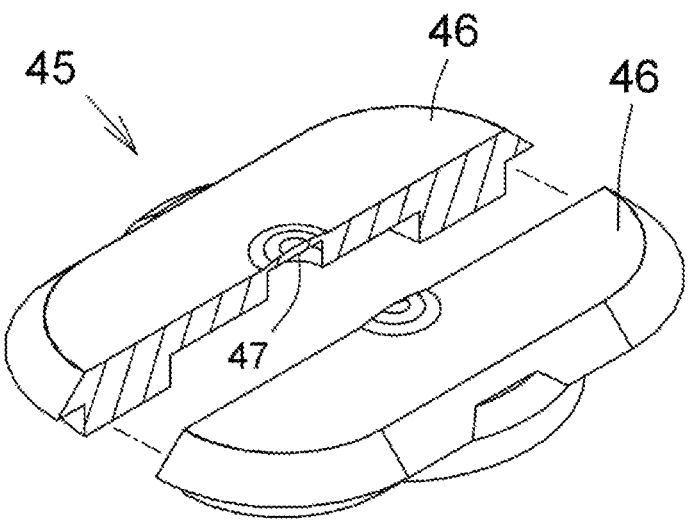
FIG. 8B is a perspective view of a compression head comprising a force gauge assembly sectioned along a long symmetry plane and spaced apart according to an another alternate embodiment of the present invention.
Figure 8C:
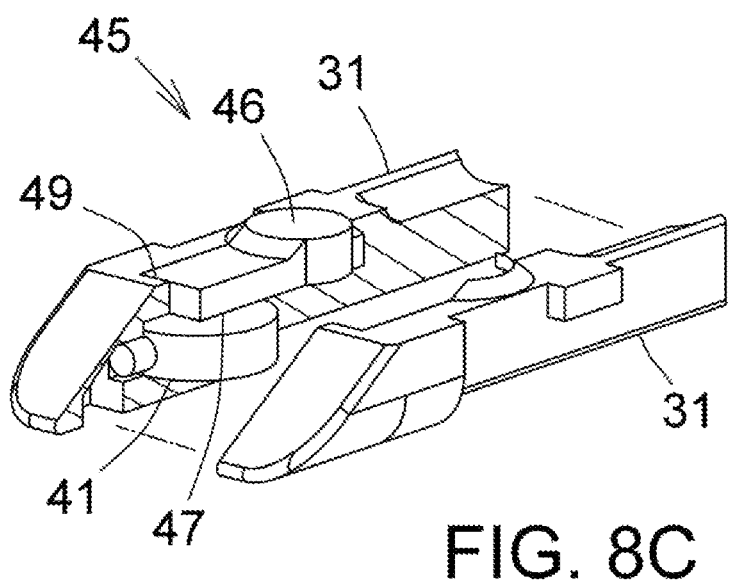
FIG. 8C is a perspective view of a cantilevered compression head comprising a force gauge assembly disposed in a cartridge body shown partially broken away, sectioned along a symmetry plane and spaced apart according to an another alternate embodiment of the present invention.
Figure 8D:
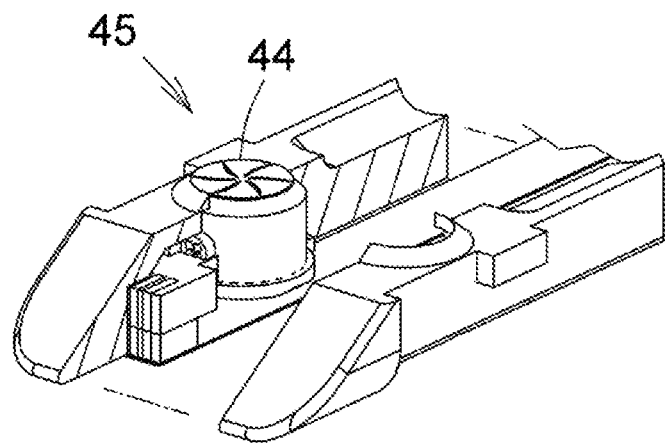
FIG. 8D is a perspective view of a deformable compression head comprising a force gauge assembly disposed in a cartridge body shown partially broken away, sectioned along a symmetry plane and spaced apart according to an another alternate embodiment of the present invention.
Figure 9B:
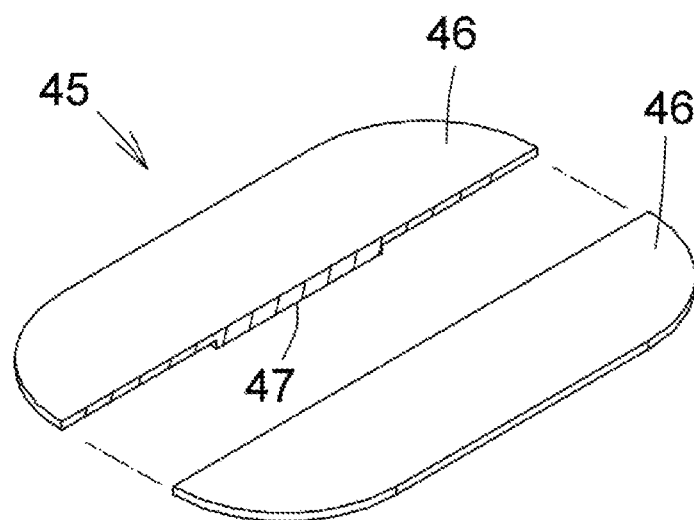
FIG. 9B is a perspective view of a compression head comprising a force gauge assembly sectioned along a symmetry plane and spaced apart according to an another alternate embodiment of the present invention.

In various embodiments of the present invention compression head 45 may take on different configurations and mechanical characteristics that suit a particular application of a compression gauge cartridge of the present invention. For example, as shown in FIGS. 7B, 8B and 9B, configuration of transducer contact face 47 may be varied to accommodate force transducer 41 of different geometry, and the area and profile of tissue compression face 46 may be predetermined, for example, to control the degree of tissue compression optionally in conjunction with variation of a gap distance between tissue compression face 46 and tissue contacting surface 24, which is primarily controllable with a spacer member 50, as will be described hereinafter. In an embodiment compression head 45 may be of substantially rigid construction to be able to transfer a reactionary load imparted on tissue compression face 46 thereof to transducer contact face 47 without a mechanical loss even when the reactionary load is unevenly distributed over tissue compression face 46. In an alternate embodiment compression head 45 may be of substantially rigid construction to be able to resist deformation under a compressive load imparted thereon by the compressed tissue but otherwise of flexible nature as may be the case for a relatively thin compression head that may be employed for a force transducer of a planar configuration as schematically illustrated in FIG. 9B. In an embodiment of the present invention compression head 45 may be configured to float, that is, be left unattached other than the mechanical engagement with force transducer 41 through transducer contact face 47 thereof. In an alternate embodiment compression head 45 may be fixedly joined with cartridge body 31 in such a configuration that allows a displacement thereof, and concomitant deflection of force transducer 41, in response to a reactionary load from a compressed tissue to occur through a predetermined deformation of compression head 45. In an exemplary embodiment, as previously described with reference to FIGS. 3C and 3D, compression head 45 may be fixedly joined with seal member 37 having sufficient flexibility to provide freedom of movement thereto. In an alternate exemplary embodiment, as shown in FIG. 8C, compression head 45 may be configured and disposed to cantilever with respect to a fixed position 49 on cartridge body 31 with tissue compression face 46 thereof positioned remotely from fixed position 49 and transducer contact face 47 positioned therebetween. In another alternate exemplary embodiment, compression head 45 may comprise a deformable member 44 fixedly joined with cartridge body 31 in a predetermined pattern, for example, along the periphery as shown in FIG. 8D schematically illustrating a cartridge body sectioned and spaced apart, and a force gauge assembly, that is configured to flex substantially perpendicularly, i.e., up and down, with respect to tissue contacting surface 46 of cartridge body 31.

Figure 10A:
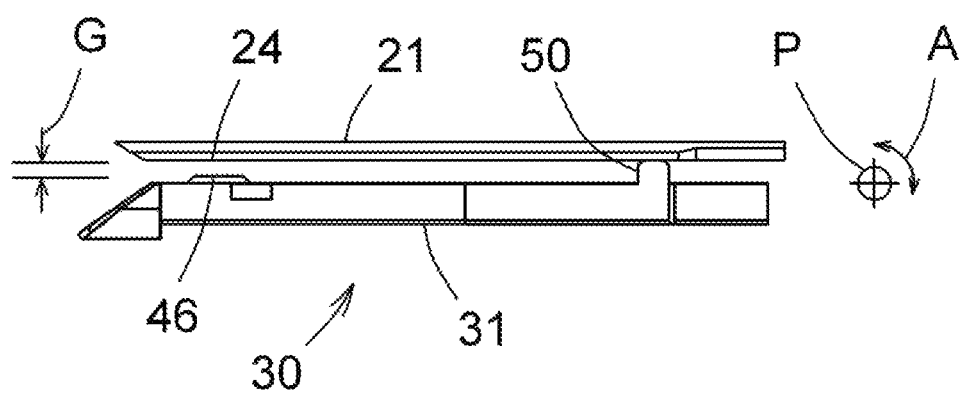
FIGS. 10A and 10B are side elevation views of a compression gauge cartridge comprising a cartridge jaw member and an anvil jaw member according to embodiments of the present invention.
Figure 10B:
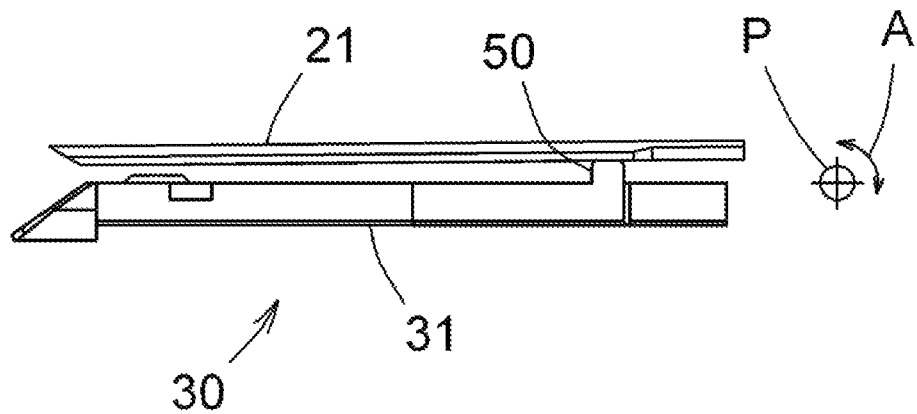

Referring to FIGS. 3A-5B, in a preferred embodiment of the present invention spacer member 50 may be of a rigid construction extending from tissue supporting surface 34 of cartridge body 31 disposed between proximal end 33 and distal end 32 thereof and proximal to compression head 45 comprising force gauge assembly 40. In an embodiment spacer member 50 may be configured to be a positive stop constraining a pivotal motion of the two jaw members comprising an end effector and substantially defining the closest gap distance at the position of spacer member 50 between tissue contacting surfaces 24, 26 of anvil jaw member 21 and cartridge jaw member 22. In the absence of a deflection of an anvil jaw member, spacer member 50 also determines a predetermined gap distance between tissue compression face 46 of compression head 45 and tissue contacting surface 24 of anvil jaw member 21 with two jaw members comprising an end effector in a fully closed position. Spacer member 50 also plays an important role in substantially eliminating variation in the gap distance stemming from a play present in the pivot and drive mechanisms of a pivotal joint of the two jaw members comprising an end effector. Referring to FIGS. 10A and 10B schematically showing, in a side elevation view, a positional relationship between a cartridge jaw member represented by compression gauge cartridge 30 and an anvil jaw member in a fully closed position, in an embodiment of the present invention, spacer member 50 may be dimensioned to make the two planes, substantially defined by tissue supporting surface 34 and tissue contacting surface 24, respectively, to be substantially parallel with each other in providing a predetermined gap distance G between tissue compression face 46 and tissue contacting surface 24. In an alternate embodiment spacer member 50 may be dimensioned to make the two planes to be at a predetermined angle with each other in providing a predetermined gap distance G between tissue compression face 46 and tissue contacting surface 24. In a further embodiment spacer member 50 may be dimensioned so that substantially all the plays in a pivot mechanism and a drive mechanism of a pivotal joint of the two jaw members are fully taken up when the two jaw members are in fully closed position as will be further described in the following section.

Figure 11A:
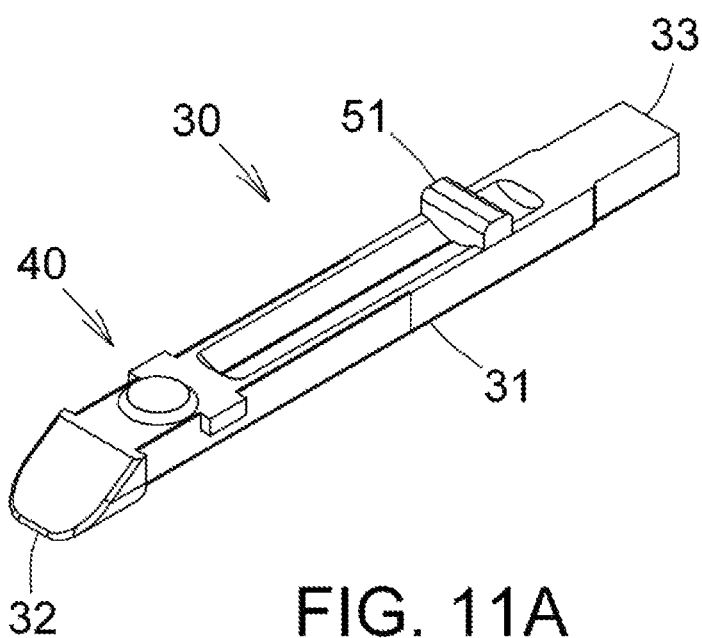
FIG. 11A is a perspective view of a cartridge body and a repositionable spacer member comprising a compression gauge cartridge according to an embodiment of the present invention.

In a preferred embodiment of the present invention, spacer member 50 comprising compression gauge cartridge 30 may be a block of a rigid construction fixedly joined with cartridge body 31. As shown in FIG. 11A, in an embodiment cartridge body 31 and spacer member 51 may be configured so that the position of spacer member 51 along the length of cartridge body 31 may be changed to suit a particular application of a compression gauge cartridge of the present invention. Spacer member 50 plays a significant role in substantially eliminating variation in the positional relationship between the two jaw members comprising an end effector due to plays present in the pivot and drive mechanisms of a pivotal joint of the two jaw members by acting as a rigid fulcrum disposed between the pivot mechanism and a compression head comprising a force gauge assembly that forces the plays to be fully taken up when the two jaw members reach a fully closed and, in some cases, locked position. Even when the tissue contacting surface of the anvil jaw member comes to rest making contact with the spacer member as the two jaw members close driven by the drive mechanism, the drive mechanism continues to drive the pivot mechanism to rotate one or both of the jaw members with respect to the point of contact between the anvil jaw member and the spacer member until all the plays in the pivot and drive mechanisms are fully taken up and the pivotal motion of the two jaw members comes to a solid stop reaching a final positional relationship there-between. Since, in practice, the force involved in driving the pivotal motion of the two jaw members are, by design, much larger than the largest reactionary load normally expected from a compressed tissue between the two jaw members comprising an end effector of a surgical stapler instrument, the final positional relationship between the two jaw members thus achieved remains substantially undisturbed even when the two jaw members are acted upon from the reactionary load from a compressed tissue there-between and is solely determined by the position and configuration of spacer member 50. Barring potential deflection of the anvil jaw member under a reactionary load from a compressed tissue, which can be effectively kept under control as previously described, spacer member 50 thus enables a surgical stapler instrument implemented with a compression gauge cartridge of the present invention to be used, without modification, to provide a predetermined gap distance, between the compression face of the compression head and the tissue contacting surface of the anvil jaw member, consistently and with high degree of repeatability, and concomitantly to compress a tissue consistently to a thickness corresponding to the predetermined gap distance.

Figure 11B:
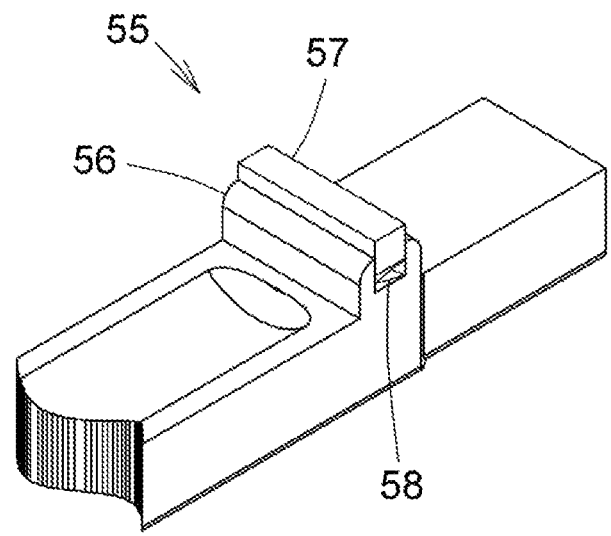
FIGS. 11B and 11C are perspective views of a spacer member with an extension member according to embodiments of the present invention.
Figure 11C:
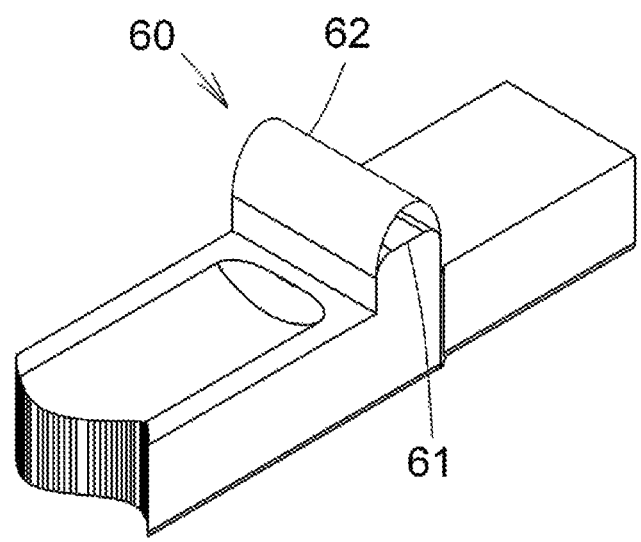
Figure 11D:
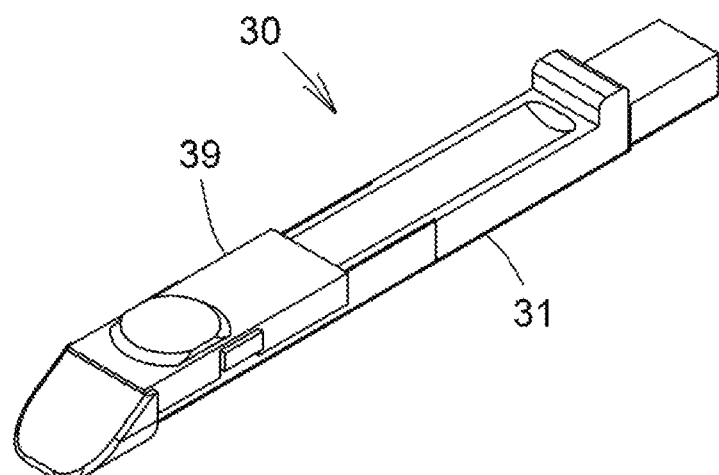
FIG. 11D is a perspective view of a protective cover disposed on a cartridge body comprising a compression gauge cartridge according to an embodiment of the present invention.

In an embodiment of the present invention, a spacer member also functions as a tissue stop defining a proximal most position along the cartridge body to which a tissue can be introduced between the two jaw members comprising an end effector. Referring to FIGS. 11B and 11C, in an embodiment spacer member 55, 60 may further comprise a spacer extension member 57, 62 for preventing a portion of a tissue getting caught, while being captured, and subsequently pinched between a spacer member and a tissue contacting surface of an anvil jaw member as the two jaw members are closed. As shown in FIG. 11B, in an embodiment spacer extension member 57 may be of a retractable/extendable type configured to move in and out of a spacer member body 56, for example, a spring 58 loaded plunger or detent biased to extend out of a cavity in spacer member body 56 to a preset limit and to follow the pivotal motion of the two jaw members keeping the gap between the spacer member and the tissue contacting surface of an anvil jaw member closed. In an alternate embodiment, as shown in FIG. 11C, spacer extension member 62 may be of a collapsible/expandable type including an air filled bladder, resilient foam, a metal spring element and a leaf spring element made of a stiff polymer film, etc, configured to require a minimal force to be collapsed down to a spacer member body 61. Referring to FIG. 11D, in an embodiment a compression gauge cartridge may comprise a protective cover 39 providing protection, for example, undesirable impact during handling, over at least part of cartridge body 31 thereof, preferably, including the general area around the position of the force gauge assembly.

Figure 12A:
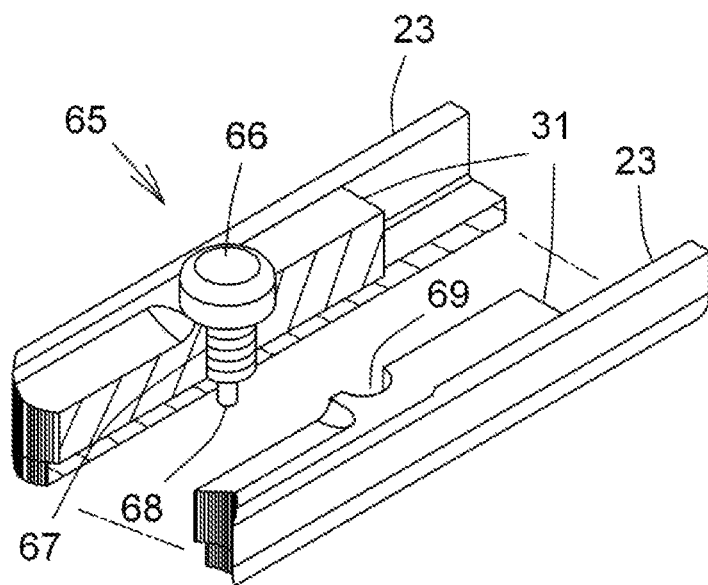
FIGS. 12A-12C are perspective views of a cartridge body and a cartridge bay, partially broken away and sectioned and spaced apart, and an adjustable spacer member comprising a compression gauge cartridge according to various embodiments of the present invention.
Figure 12B:
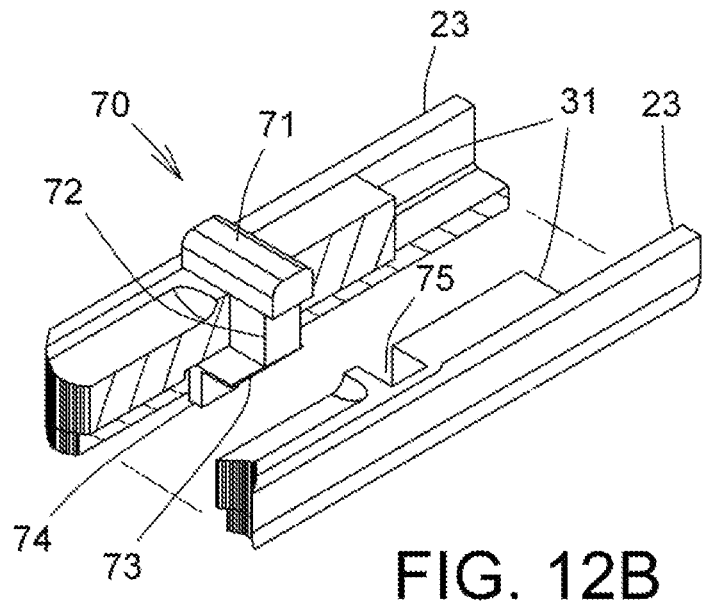
Figure 12C:
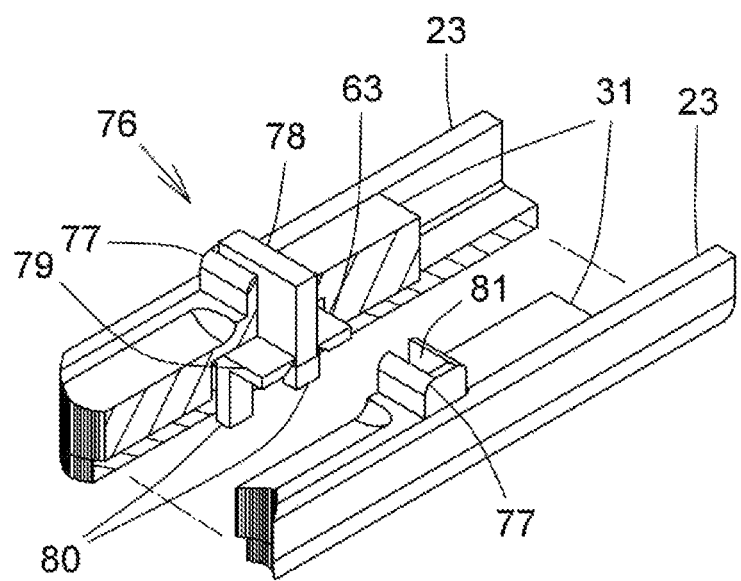

Referring to FIGS. 12A-12C showing a spacer member, and a cartridge body 31 and a cartridge bay 23 broken away and sectioned apart, in an embodiment of the present invention, a spacer member comprising a compression gauge cartridge may be configured so that the height thereof over the tissue supporting surface of the cartridge body, i.e., the vertical extent the spacer member extends from the tissue supporting surface, may be adjusted. As shown in FIG. 12A, in an embodiment of the present invention, an adjustable spacer member 65 having an anvil contacting face 66 may be mounted on a threaded base 67 of a gender disposed in a hole 69 in cartridge body 31 with a matching thread of an opposite gender so that the vertical position of anvil contacting face 66 may be adjusted by turning a control stem 68 fixedly joined with threaded base 67 and disposed through a slot normally found in cartridge bay 23. As shown in FIG. 12B, in an alternate embodiment, an adjustable spacer member 70 having an anvil contacting face 71 may comprise a rigid base 72 disposed in a hole 75 in cartridge body 31 and on a wedge shape platform 73 joined with a control stem 74 disposed through a slot in cartridge bay 23 so that the vertical position of anvil contacting face 71 may be adjusted and locked in a position by sliding control stem 74 along the slot. As shown in FIG. 12C, in another alternate embodiment, an adjustable spacer member 76 may be configured to have a nested structure comprising a stationary base 77 and a movable plunger 78 slidably engaged with stationary base 77 in a hole 81 for vertical movement with respect to the tissue supporting surface and to include at least one break member 79 with a predetermined breaking mechanism, for example, a sharp edge, drivable with control stems 80 fixedly joined therewith and disposed through a slot in cartridge bay 23 so that movable plunger 78 may be securely held immobile once the desired vertical position thereof is reached. In an embodiment adjustable spacer member 65, 70, 76 may be configured with a bias spring that drives adjustable spacer member or a movable part thereof to a final position when triggered by a predetermined event, an example of which will be described hereinafter.

Figure 12D:
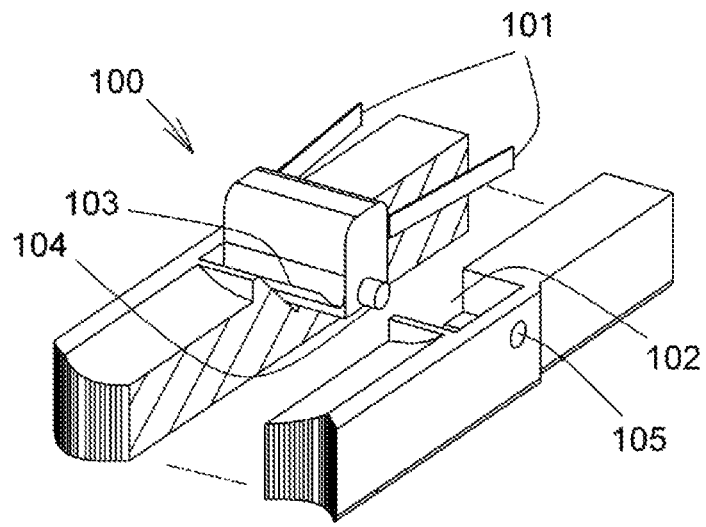
FIGS. 12D and 12E are perspective views of a cartridge body and a cartridge bay, partially broken away and sectioned and spaced apart, and a rotatable spacer member comprising a compression gauge cartridge according to an alternate embodiment of the present invention.
Figure 12E:
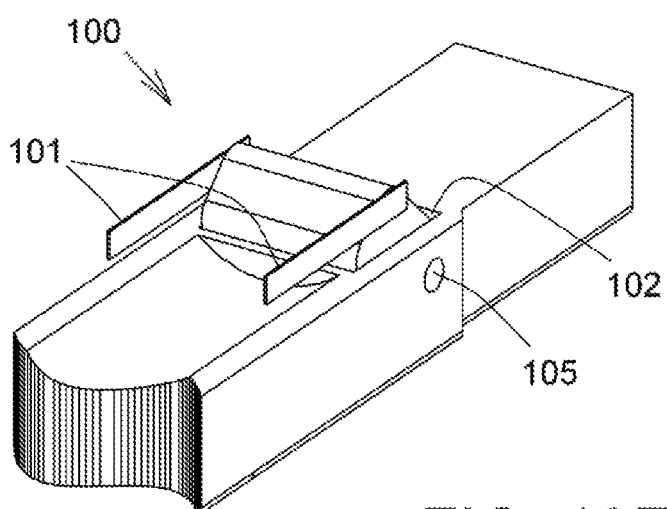

As shown in FIGS. 12D and 12E, in an embodiment of the present invention a spacer member 100 may be configured to include an axle 104, a spring element 103 and at least one flap member 101, and to be disposed in a cavity 102 in a cartridge body comprising a compression gauge cartridge with axel 104 rotatably mated with a pair of holes 105 in the cartridge body so that spacer member 100 may pivot with respect to the cartridge body around axle 104. Spring element 103 may be configured to bias spacer member 100 so that it remains upright with respect to the cartridge body ready to withstand the downward load from the anvil member when the two jaw members comprising the end effector are in a fully closed position. At least one flap member 101 may be configured and disposed with respect to spacer member 100 so that it may be flipped proximally and distally therewith when acted on by the proximal and distal ends of a trocar, respectively, during insertion and removal there-through of a surgical stapler instrument instrumented with the compression gauge cartridge. In an embodiment spacer member 100 may be rotated to reduce the height thereof above the cartridge body, as schematically shown in FIG. 12E, manually by a physician prior to insertion of a surgical stapler instrument or automatically by the interaction thereof with the distal end of the trocar during removal of a surgical stapler instrument. A spacer member of such a configuration would enable use of a compression gauge cartridge with a spacer member so tall that would make an end effector of a surgical stapler instrument instrumented with the compression gauge cartridge impassable through a normally used trocar even with the jaw members in a fully closed position.

Figure 13A:
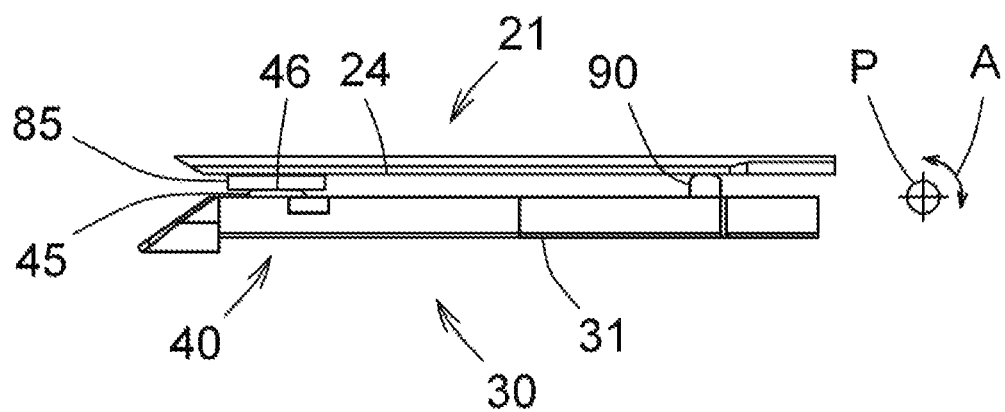
FIG. 13A is a schematic, side elevation view of a reference block, a compression gauge cartridge and an anvil jaw member according to an embodiment of the present invention.
Figure 13B:
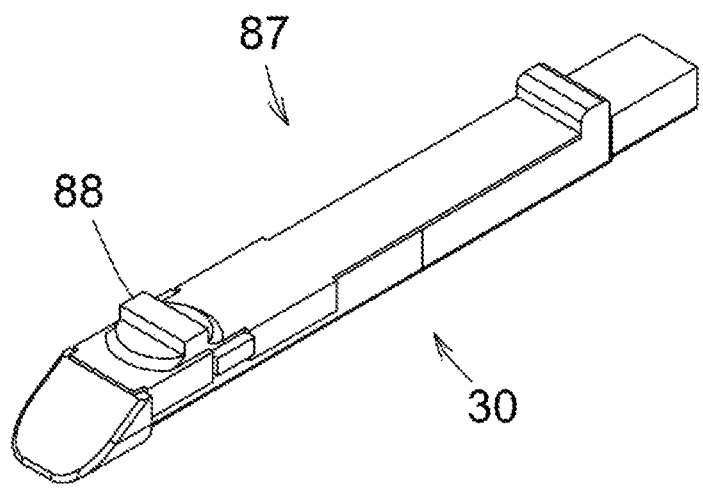
FIG. 13B is a perspective view of a protective cover disposed on a cartridge body according to an embodiment of the present invention.
Figure 13C:
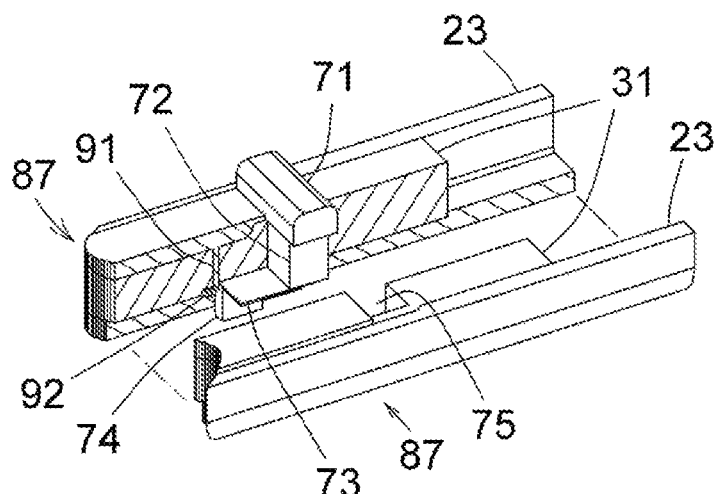
FIG. 13C is a perspective view of a cartridge body, a protective cover and a cartridge bay, partially broken away and sectioned and spaced apart, and an adjustable spacer member biased by a spring according to an embodiment of the present invention.

Surgical stapler instrument products of a design, like any other engineering products, inherently includes certain variations in their mechanical performance, which, by design, are not of significance in originally intended uses in surgical stapling operation but may negatively affect uses of a surgical stapler instrument instrumented with a compression gauge cartridge of the present invention. For example, such variations could manifest between different production lots, for example, due to change in production steps and/or even between different instruments from the same production lot, for example, due to changes in the manufacturing tolerances of parts and/or subassemblies. As described previously, changes in the plays in the pivot and drive mechanism of a surgical stapler instrument, for example, resulting from variations in manufacturing tolerances may degrade the precision in the final positional relationship between the two jaw members in a fully closed and locked position and, in turn, the predetermined gap distance between the tissue compression face of the compression head and the tissue contacting surface of the anvil jaw member corresponding to a predetermined thickness to which a tissue is compressed. To circumvent the potential impact these variations may have on the performance of a compression gauge cartridge mounted on a surgical stapler instrument or a surgical compression gauge instrument, in various embodiments of the present invention, there are provided methods for calibrating the gap distance between the tissue compression face of the compression head and the tissue contacting surface of the anvil jaw member. Referring to FIG. 13A showing, in a side elevation view, an anvil jaw member 21 and a compression gauge cartridge 30 representing a cartridge jaw member, in an embodiment a gap distance calibration method comprises steps of: (1) positioning a reference block 85 over a compression head 45 of height corresponding to a predetermined gap distance between tissue compression face 46 of compression head 45 and the tissue contacting surface 24 of anvil jaw member 21; (2) fully closing the two jaw members of the end effector; and (3) adjusting the height of an adjustable spacer member 90 until the load cell indicator reads zero. In an embodiment the height of reference block 85 may be fine tuned to reflect possible deflection of anvil jaw member 21 due to a reactionary load from reference block 85 during the gap distance calibration procedure. For example, reference block 85 may be made taller than a predetermined target gap distance to account for deflection of anvil jaw member 21. In an embodiment fully closing the two jaw members may involve operating a handle assembly comprising a surgical stapler instrument or a surgical compression gauge instrument to close the two jaw members until the handle assembly reaches a locked state corresponding to a limit of the closing operation. In an alternate embodiment a gap distance calibration method comprises steps of: (1) positioning reference block 85 over a compression head 45 of height corresponding to a predetermined gap distance between tissue compression face 46 of compression head 45 and tissue contacting surface 24 of anvil jaw member 21; (2) fully closing the two jaw members of the end effector; and (3) adjusting the height of adjustable spacer member 90 until it touches tissue contacting surface 24 of anvil jaw member 21. In another alternate embodiment a gap distance calibration method comprises steps of: (1) positioning a reference material over a compression head 45 of known tensile property and dimension between tissue compression face 46 of compression head 45 and tissue contacting surface 24 of anvil jaw member 21; (2) fully closing the two jaw members of the end effector; and (3) adjusting the height of adjustable spacer member 90 until the load cell indicator reads a predetermined value indicating the reference material is compressed to a thickness corresponding to a predetermined gap distance between tissue compression face 46 of compression head 45 and tissue contacting surface 24 of anvil jaw member 21. As shown in FIGS. 13B and 13C, in an embodiment of the present invention a protective cover 87 may be configured to comprise a built-in reference block 88 and a trigger member 91 for causing a spring 92 to drive a locking mechanism 73, 74 for adjustable spacer member 71 to facilitate the gap calibration procedure.

Figure 14:
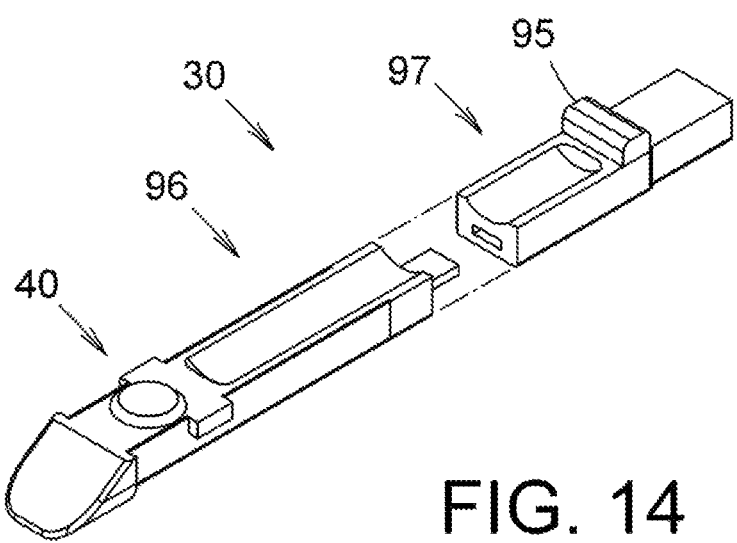
FIG. 14 is an assembly view of a compression gauge cartridge comprising two parts according to an alternate embodiment of the present invention.

Referring to FIG. 14, in an embodiment of the present invention, a compression gauge cartridge 30 may comprise two parts 96, 97, preferably, one part 96 including a force gauge assembly 40 and the other part 97 including a spacer member 95, that are configured to be releasably joined with each other. In an embodiment part 96 may be a part of compression gauge cartridge 30 that can be effectively re-sterilized and part 97 difficult to re-sterilize, for example, due to internal structures present if spacer member 95 is an adjustable spacer member as previously described. After use, part 96 may be kept for reuse following a re-sterilization and used part 97 may be discarded and exchanged with a new one.

Figure 15:
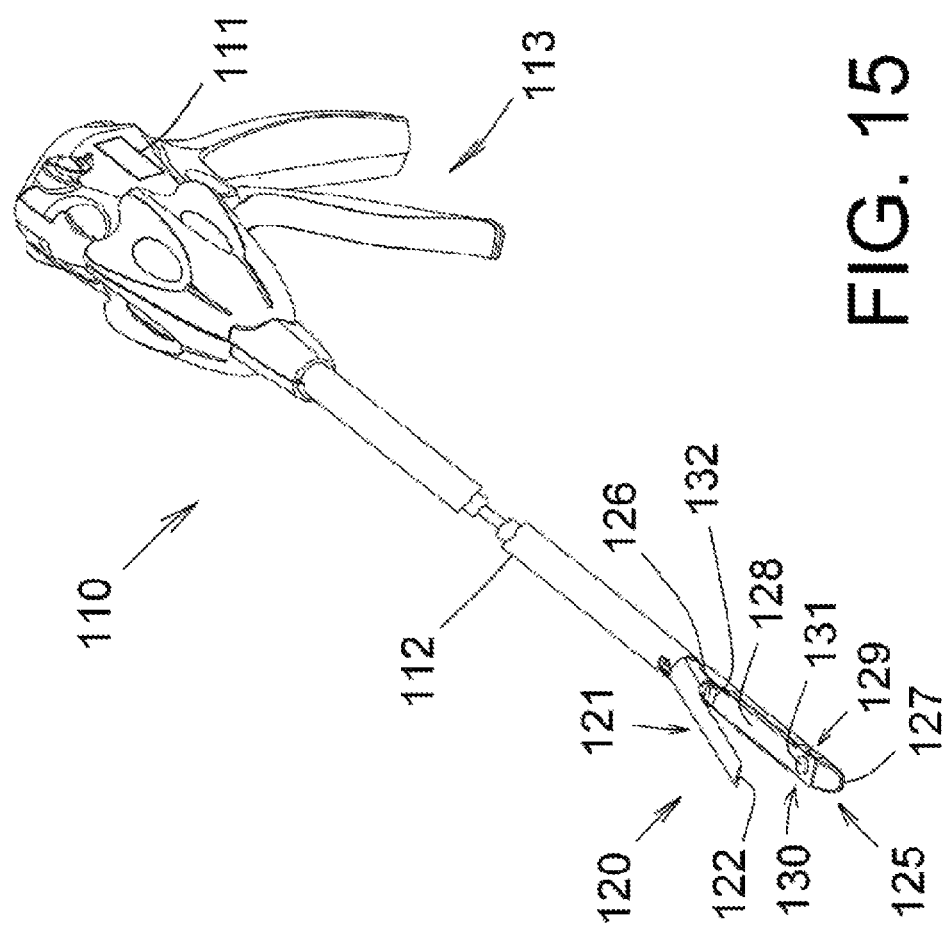
FIG. 15 is a perspective view of a surgical compression gauge instrument comprising a compression gauge jaw member according to an embodiment of the present invention.

Referring to FIG. 15, in an embodiment of the present invention, a surgical compression gauge instrument 110 for compressing a tissue consistently to a predetermined thickness and measure a reactionary load therefrom for assisting selection of a staple cartridge and assessing the condition of the tissue comprises: a handle portion 111; a body portion 112 extending distally from handle portion 111 and defining a longitudinal axis; and a tool assembly 120 at the distal end of and operatively connected to body portion 112, tool assembly 120 comprising an anvil jaw member 121 having a tissue contacting surface 122 and a compression gauge jaw member 125, configured to open and close when operated by handle portion 111, wherein compression gauge jaw member 125 having a proximal end 126 and a distal end 127, and a tissue supporting surface 128 comprises a force gauge assembly 129 comprising a force transducer (not shown in the FIGURE) and a compression head 130 having a tissue compression face 131, supported by compression gauge jaw member 125 positioned between proximal end 126 and distal end 127 thereof, and wherein compression head 130 of force gauge assembly 129 is disposed so that tissue compression face 131 thereof lies substantially closer to tissue contacting surface 122 of anvil jaw member 121 than tissue supporting surface 128 of compression gauge jaw member 125; and a spacer member 132 extending from tissue supporting surface 128 comprising compression gauge jaw member 125, wherein force gauge assembly 129 is positioned distally with respect to spacer member 132.

In a preferred embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from the standard set of staple cartridges containing staples of a height corresponding to said predetermined thickness of said compressed tissue if the result of comparison is case (1), or a staple cartridge containing staples of a height smaller than said predetermined thickness of said compressed tissue taking into account said size of difference if the result of comparison is case (2), or a staple cartridge containing staples of a height larger than said predetermined thickness of said compressed tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined average height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to an average height of staples contained in a predetermined cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value and how large a size of difference is in cases (2) and (3); selecting a staple cartridge from said standard set of staple cartridges containing staples of an average height corresponding to said predetermined thickness of said compressed tissue if the result of comparison is case (1), or a staple cartridge containing staples of an average height smaller than said predetermined thickness of said compressed tissue taking into account said size of difference if the result of comparison is case (2), or a staple cartridge containing staples of an average height larger than said predetermined thickness of said compressed tissue taking into account said size of difference if the result of comparison is case (3). In an alternate embodiment, a method for selecting a staple cartridge from the standard set of staple cartridges, each containing staples of a predetermined average height, optimal for a tissue of a surgical stapling operation may further comprise a step of waiting for a predetermined length of time after closing said cartridge jaw member and said anvil jaw member to compress said tissue.

In another alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance, corresponding to a height of staples contained in a green cartridge from the set of standard staple cartridges, between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; comparing said reactionary load reading with a value known to be optimal for a stapling operation of said tissue to determine if said reactionary load is case (1) within, case (2) below or case (3) above a window of a predetermined width around said optimal value; selecting a green cartridge from the standard set of staple cartridges if the result of comparison is case (1) or a blue cartridge if the result of comparison is case (2), or a black cartridge if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member, of a surgical stapler instrument, a spacer member of which is configured to consistently provide a gap distance between a tissue compression face of a compression head comprising a force gauge assembly comprising said compression gauge cartridge and a tissue contacting surface of said anvil jaw member; capturing a tissue between said cartridge jaw member and said anvil jaw member; closing said cartridge jaw member and said anvil jaw member to compress said tissue captured between said tissue compression face and said tissue contacting surface to a predetermined thickness corresponding to said gap distance there-between; reading out a reactionary load from said compressed tissue displayed on a force transducer indicator; providing a reference tissue for which an optimal staple height for a surgical stapling operation is known; comparing said reactionary load reading with a reactionary load from said reference tissue compressed to said predetermined thickness over the same area of said reference tissue as that of said tissue compression face of said compression head to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

Figure 16:
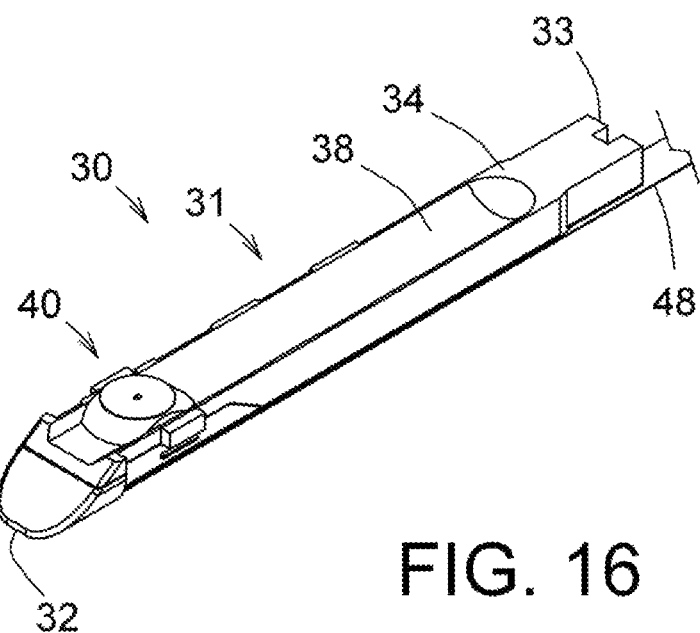
FIG. 16 is a perspective view of a compression gauge cartridge according to an alternate embodiment of the present invention.
Figure 17:
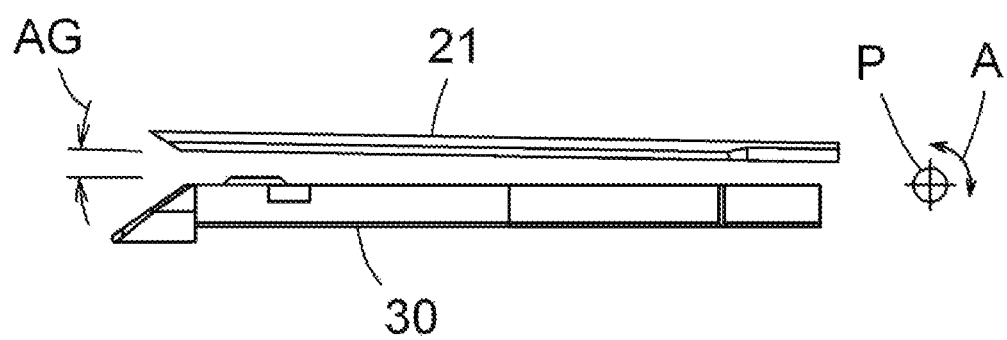
FIG. 17 is a side elevation view of a compression gauge cartridge comprising a cartridge jaw member and an anvil jaw member according to embodiments of the present invention.
Figure 19:
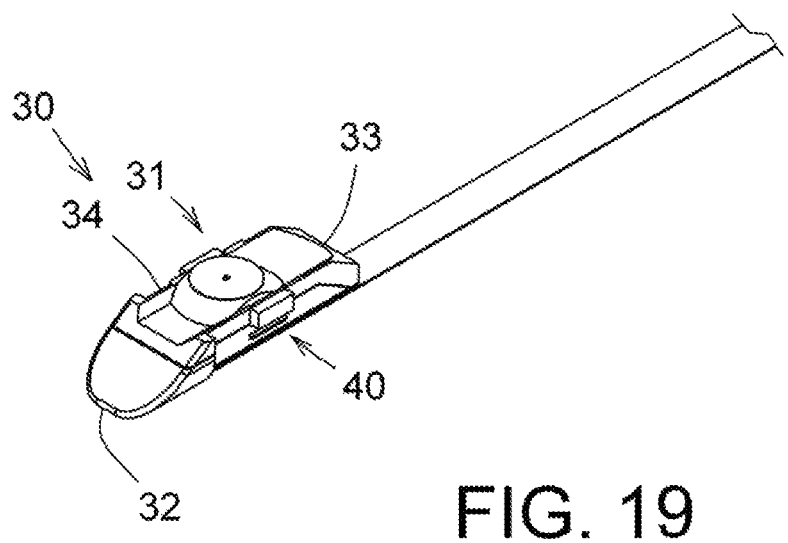
FIG. 19 is a perspective view of a compression gauge cartridge according to an alternate embodiment of the present invention.

Referring to FIG. 16, showing a compression gauge cartridge 30 in a perspective view in an embodiment of the present invention, compression gauge cartridge 30 for use mounted in a cartridge bay of a cartridge jaw member comprising an end effector of a surgical stapler instrument, together with an anvil jaw member having a tissue contacting surface, to compress a tissue so that said cartridge jaw member and said anvil jaw member come to a predetermined angular positional relationship with each other, as indicated in FIG. 17 by a label AG in a schematic representation of an anvil jaw member 21 and compression gauge cartridge 30, and measure a reactionary load therefrom for assisting in selection of a staple cartridge optimal for a tissue of a surgical stapling operation comprises: a cartridge body 31 having a proximal end 32 and a distal end 33, and a tissue supporting surface 34, wherein cartridge body 31 may be configured for compression gauge cartridge 30 to be releasably mounted in said cartridge bay and for tissue supporting surface 34 to be at least at a predetermined distance from said tissue contacting surface of said anvil jaw member when cartridge jaw member and said anvil jaw member are in a fully closed position; and a force gauge assembly 40 comprising a force transducer and a compression head having a tissue compression face, wherein force gauge assembly 40 may be supported by cartridge body 31 positioned between proximal end 32 and distal end 33 thereof, and wherein said compression head comprising said force gauge assembly 40 may be configured and disposed so that said tissue compression face thereof may lie substantially closer to said tissue contacting surface of said anvil jaw member than tissue supporting surface 34 of cartridge body 31. In an alternate embodiment tissue supporting surface 34 of cartridge body 31 may be contoured in such a way to further reduce compression of a tissue disposed between tissue supporting surface 34 and said tissue contacting surface when said cartridge jaw member and said anvil jaw member are in a fully closed position. Compression gauge cartridge 30 is configured to allow an existing surgical stapler instrument to be used without modification in applying a compression to a predetermined area of a tissue captured between the two jaw members comprising an end effector thereof so that the two jaw members come to a predetermined positional relationship with each other and measuring a reactionary load from the compressed area of the tissue. In an embodiment of the present invention cartridge body 31 comprising compression gauge cartridge 30 may be configured for compression gauge cartridge 30 to be releasably mounted and securely retained in a cartridge bay comprising a cartridge jaw member of an end effector. In an alternate embodiment cartridge body 31 comprising compression gauge cartridge 30 may be configured to be fixedly mounted in a cartridge bay to be integrated with a cartridge jaw member of an end effector of a surgical stapler instrument. In another alternate embodiment cartridge body 31 comprising compression gauge cartridge 30 may be configured to be fixedly mounted in a cartridge bay to be integrated with a cartridge jaw member of an end effector comprising a disposable reload unit of a certain surgical stapler instrument product in the market. In an alternate embodiment of the present invention the dimension of a cartridge body comprising a compression gauge cartridge may be varied to suit particular application thereof. For example, as shown in FIG. 19, cartridge body 31 may be configured to be shorter than a conventional staple cartridge along the length of a cartridge bay.

Figure 18:
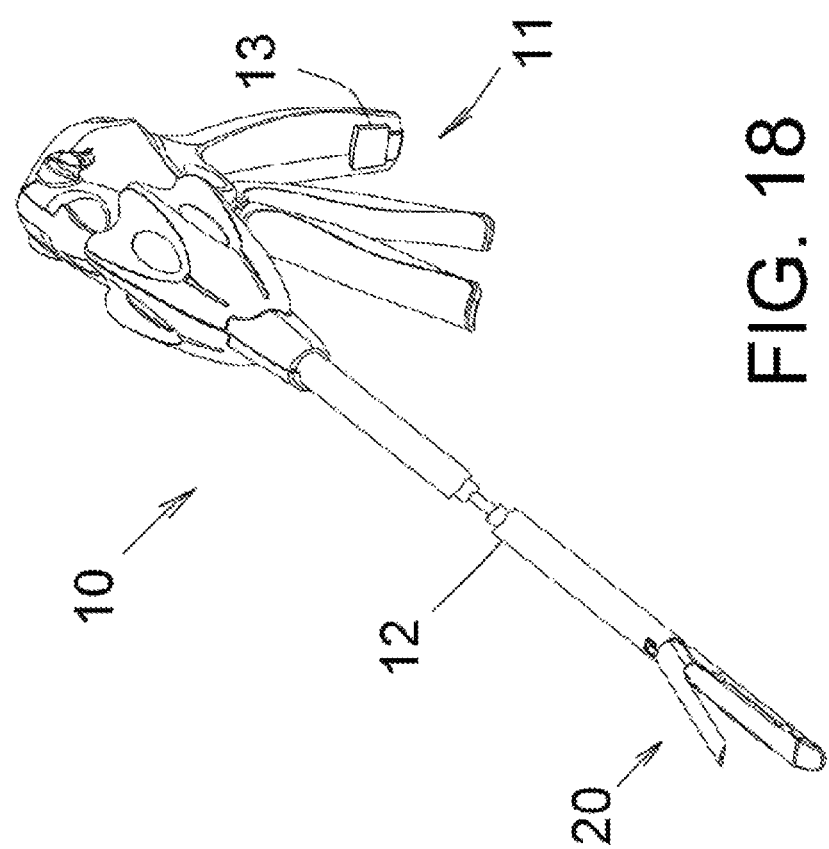
FIG. 18 is a perspective view of a surgical stapler instrument according to an embodiment of the present invention.

Referring to FIG. 18, in an embodiment of the present invention, a surgical stapler instrument 10 may further include a spacer block 13 of a predetermined height disposed at a handle 11 comprising surgical stapler instrument 10 for defining a predetermined extent handle 11 may be operated to close a cartridge jaw member and an anvil jaw member comprising an end effector 20 comprising surgical stapler instrument 10 so that said cartridge jaw member and said anvil jaw member come to a predetermined angular positional relationship with each other.

In an alternate embodiment of the present invention, a method for selecting a staple cartridge from the standard set of staple cartridges, each containing staples of a predetermined height, optimal for a tissue of a surgical stapling operation comprises steps of: mounting a compression gauge cartridge of the present invention in a cartridge bay of a cartridge jaw member comprising an end effector, together with an anvil jaw member having a tissue contacting surface, of a surgical stapler instrument; capturing a tissue between said cartridge jaw member and said anvil jaw member; closing said cartridge jaw member and said anvil jaw member to compress said tissue captured there-between so that said cartridge jaw member and said anvil jaw member come to a predetermined angular positional relationship with each other; reading out a reactionary load from said compressed tissue displayed on a force transducer indicator; providing a reference tissue for which an optimal staple height for a surgical stapling operation is known; comparing said reactionary load reading with a reactionary load from said reference tissue compressed so that said cartridge jaw member and said anvil jaw member come to said predetermined angular positional relationship with each other to determine if said reactionary load is case (1) within, case (2) below or case (3) above a window of a predetermined width around said reactionary load from said reference tissue and how large a size of difference is in cases (2) and (3); selecting a staple cartridge from the standard set of staple cartridges containing staples of a height known to be optimal for said reference tissue if the result of comparison is case (1), or a staple cartridge containing staples of a height smaller than that of staples known to be optimal for said reference tissue taking into account said size of difference if the result of comparison is case (2), or a staple cartridge containing staples of a height larger than that of staples known to be optimal for said reference tissue taking into account said size of difference if the result of comparison is case (3). In an alternate embodiment, a method for selecting a staple cartridge from the standard set of staple cartridges, each containing staples of a predetermined height, optimal for a tissue of a surgical stapling operation may further comprise a step of waiting for a predetermined length of time after closing said cartridge jaw member and said anvil jaw member to compress said tissue.

Figure 20:
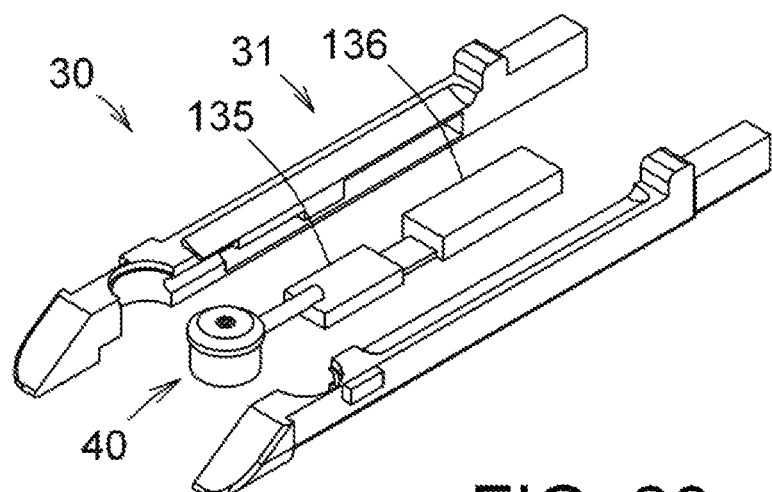
FIG. 20 is a perspective view of a compression gauge cartridge with a cartridge body sectioned similarly to that shown in FIG. 3C and spaced apart according to an alternate embodiment of the present invention.

Referring to FIG. 20, showing a compression gauge cartridge 30 in a perspective view in an embodiment of the present invention, compression gauge cartridge 30 for use mounted in a cartridge bay of a cartridge jaw member comprising an end effector of a surgical stapler instrument to compress a tissue and measure a reactionary load therefrom for assisting in selection of a staple cartridge optimal for a tissue of a surgical stapling operation comprises: a cartridge body 31; and a force gauge assembly 40, an electronic circuit module 135 including a signal processing circuit for conditioning and digitizing a signal from said force gauge assembly 40 and wireless transmission circuit, and a battery module 136 for providing operational power to said force gauge assembly 40 and said electronic circuit module 135 housed in said cartridge body 31. In an embodiment, there is provided a corresponding force transducer indicator (not shown in the FIGURE) configured to receive and display a wireless signal from compression gauge cartridge 30 indicating the result of measurement by said force gauge assembly 40. In an embodiment said battery module 136 may be of rechargeable type.

Figure 21:
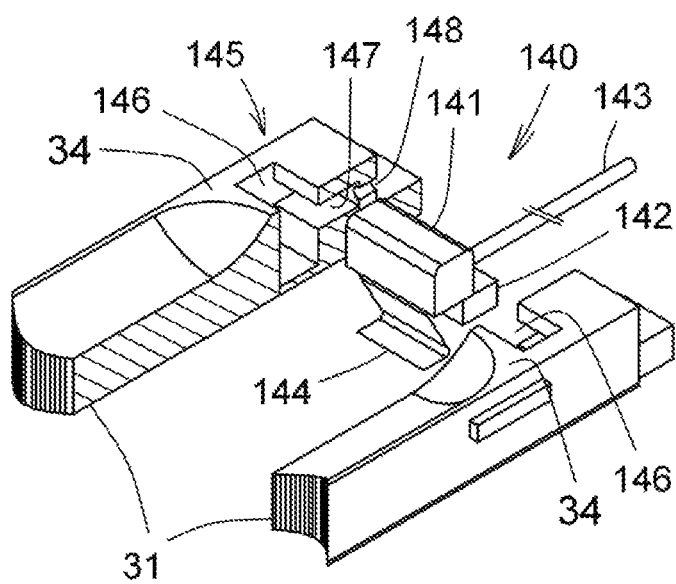
FIG. 21 is a perspective view of a cartridge body, partially broken away, and sectioned and spaced apart, and a spacer assembly according to an embodiment of the present invention.
Figure 22A:
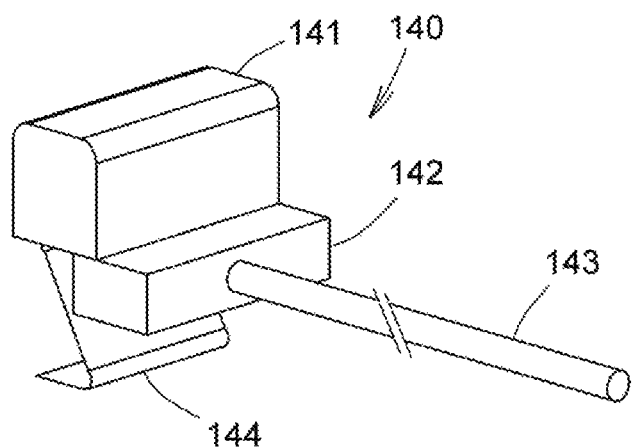
FIG. 22A is a perspective view of a spacer assembly with the stopper in the path of the spacer member according to an embodiment of the present invention.
Figure 22B:
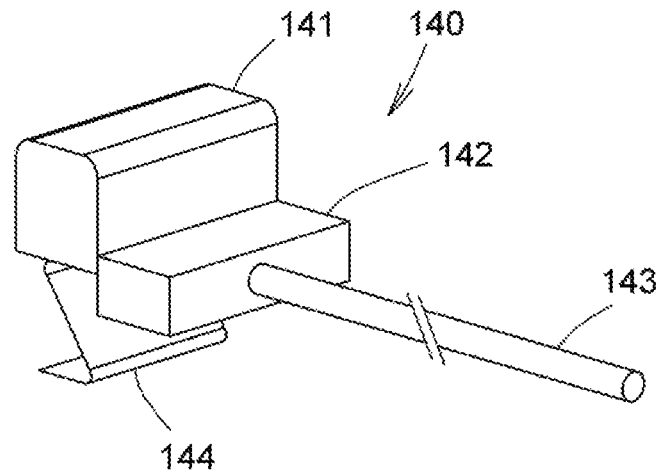
FIG. 22B is a perspective view of a spacer assembly with the stopper out of the path of the spacer member according to an embodiment of the present invention.

In an embodiment of the present invention there is provided a compression gauge cartridge comprising a cartridge body configured to allow a spacer member to be extended to and held in position at a predetermined extent or height above the tissue supporting surface of the cartridge body and retracted to or below the height required for insertion and withdrawal through a trocar of the surgical stapler instrument, the end effector of which the compression gauge cartridge is mounted in. Such a compression gauge cartridge enables a surgical stapler instrument implemented therewith to probe a tissue, that is, compress a tissue and measure a reactionary load therefrom, at compressed tissue thickness that cannot be accommodated by a compression gauge cartridge with a fixed height spacer member due to constraint on the height thereof imposed by the size of a trocar through which the surgical stapler instrument must be inserted and withdrawn. Similarly, a compression gauge jaw member comprising a surgical compression gauge instrument implemented with a retractable spacer member enables the surgical compression gauge instrument to probe a tissue at thickness level that cannot be accommodated by a compression gauge jaw member with a fixed height spacer member due to constraint on the height thereof imposed by the size of a trocar through which the surgical compression gauge instrument must be inserted and withdrawn. Referring to FIG. 21 showing a spacer assembly 140 and a cartridge body 31 comprising a compression gauge cartridge, broken away and sectioned apart, in an embodiment of the present invention, cartridge body 31 may be configured to include a cavity 145 for housing a spacer assembly 140 comprising a spacer member 141, a stopper 142, a stopper control link 143, operatively joined with stopper 142, and a spacer spring 144. Cavity 145 may comprise a spacer channel 146 disposed substantially perpendicularly to tissue supporting surface 34 of cartridge body 31 with one end open to tissue supporting surface 34 for passage of spacer member 141 and the other end closed, and a stopper channel 147 disposed to intersect spacer channel 146 substantially perpendicularly thereto in one end including a passage 148 for stopper control link 143 in the other end. Spacer member 141 may be of rigid construction and configured to slidably engage spacer channel 146 to enable smooth and substantially precise movement along the length of spacer channel 146. Stopper 142 may be configured to slidably engage stopper channel 147 to enable smooth and substantially precise movement along the length of stopper channel 147. Disposed in spacer channel 146 between the closed end thereof and spacer member 141, spacer spring 144 may be configured to bias spacer member 141 to move in the direction of the open end of spacer channel 146. Stopper 142 may be driven by stopper control link 143 to position stopper 142 in, as shown in FIG. 22A, and out, as shown in FIG. 22B, of the path of spacer member 141 in spacer channel 146. In an embodiment stopper 142 may be configured and constructed to provide a rigid stop to spacer member 141 when positioned in the path thereof. Stopper control link 143 may be operatively joined on the one end with stopper 142 and on the other end with a mechanical or electronic control mechanism, preferably located on the handle of a surgical stapler instrument with a compression gauge cartridge or a surgical compression gauge instrument, collectively referred to as the compression gauge instrument hereinafter, to be operated by the physician operator of the compression gauge instrument. In the path of spacer member 141, as shown in FIG. 22A, stopper 142 rigidly holds spacer member 141 in position extended above tissue supporting surface 34 of cartridge body 31 at a predetermined height maintaining a relative positional relationship of the two jaw members of end effector of the compression gauge instrument closed to compress a tissue captured there-between. Out of the path of spacer member 141, as shown in FIG. 22B, stopper 142 allows spacer member 141 to be retracted to or below a height above tissue supporting surface 34 of cartridge body 31 necessary for the two jaw members to be closed sufficiently to allow the end effector of the compression gauge instrument to pass through a trocar.

Figure 23A:
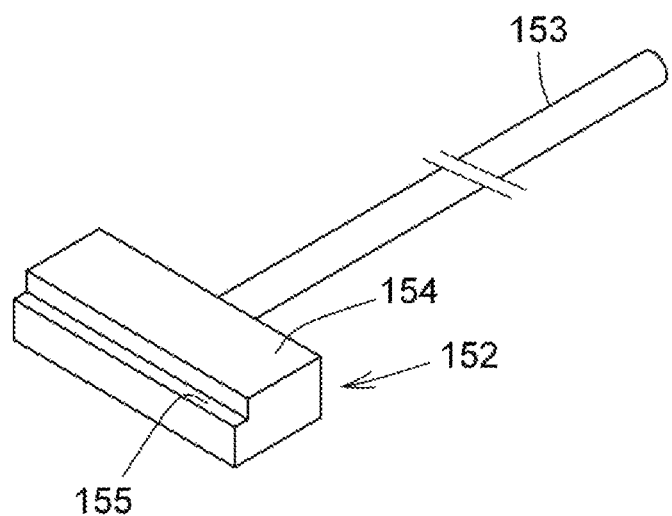
FIG. 23A is a perspective view of a stopper comprising a plurality of steps joined with a stopper control link according to an embodiment of the present invention.
Figure 23B:
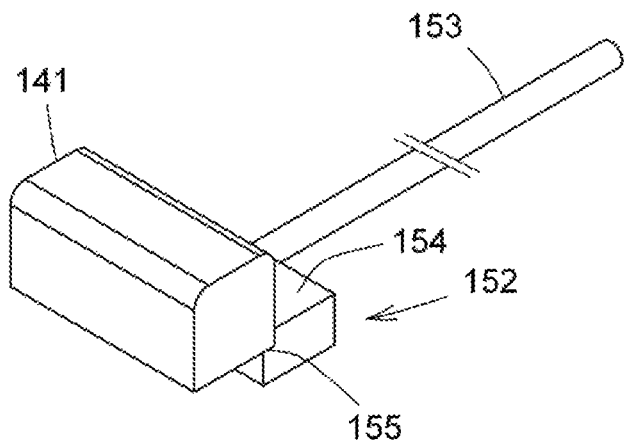
FIG. 23B is a perspective view of a spacer member held in position resting at a step of a stopper comprising a plurality of steps joined with a stopper control link according to an embodiment of the present invention.
Figure 23C:
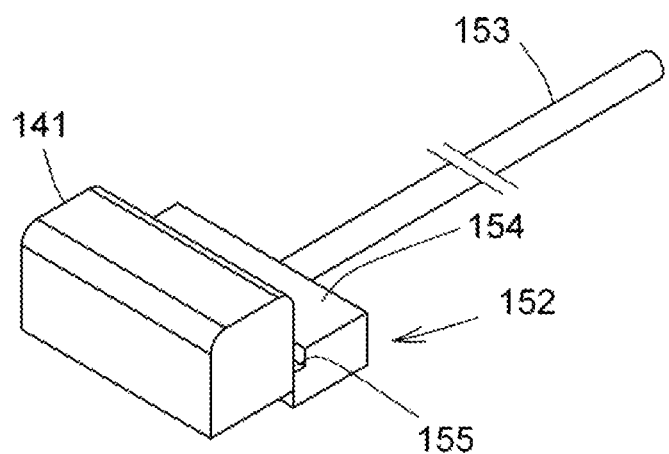
FIG. 23C is a perspective view of a spacer member with a stopper, comprising a plurality of steps joined with a stopper control link, out of the path thereof according to an embodiment of the present invention.
Figure 24:
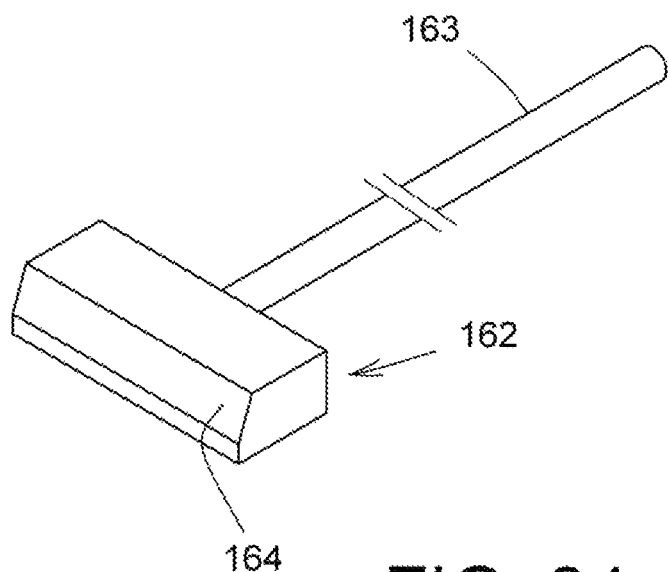
FIG. 24 is a perspective view of a stopper comprising a sloped face joined with a stopper control link according to an embodiment of the present invention.

In an embodiment of the present invention, as shown in FIG. 23A, stopper 152 may comprise a plurality of steps 154, 155, each corresponding to a predetermined height of the spacer member above the tissue supporting surface of the cartridge body. As show in FIG. 23B, in an exemplary embodiment, spacer member 141 resting on step 155 may provide a smaller gap distance between the two jaw members of end effector of the compression gauge instrument and correspondingly a smaller compressed tissue thickness captured and compressed by the two jaw members. As shown in FIG. 23C stopper 152 out of the path of spacer member 141, spacer member 141 may be retracted into the spacer channel to allow sufficient closure of the two jaw members for passage of the end effector and withdrawal of the compression gauge instrument through a trocar. In an embodiment of the present invention, as shown in FIG. 24, stopper 162 may include a sloped face 164 that may allow the height of the spacer member above the tissue supporting surface of the cartridge body to be varied continuously. In an exemplary embodiment, the stopper is depicted generally of a square block shape the stopper may be of any other configuration. In an embodiment the spacer member and stopper may be further configured to include an arrangement to stop the spacer member from being ejected clear out of the spacer channel by the spacer spring. In an alternate embodiment the cavity of the cartridge body may be configured with an arrangement to stop the spacer member from being ejected clear out of the spacer channel by the spacer spring.

Figure 25:
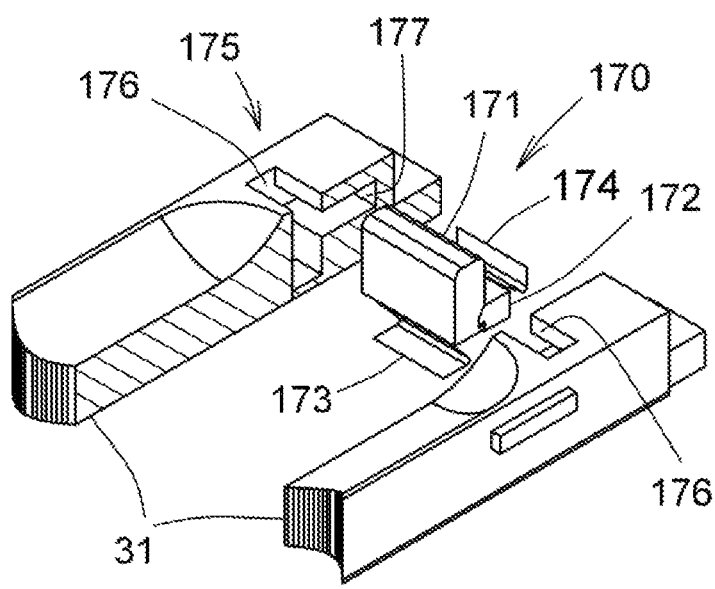
FIG. 25 is a perspective view of a cartridge body, partially broken away, and sectioned and spaced apart, and a spacer assembly according to an embodiment of the present invention.

In an alternate embodiment of the present invention there is provided a compression gauge cartridge comprising a cartridge body configured to allow a spacer member to be extended to and held in position at a predetermined height above the tissue supporting surface of the cartridge body and retracted to or below the height required for insertion and withdrawal through a trocar of the surgical stapler instrument the end effector of which the compression gauge cartridge is mounted in. Referring to FIG. 25 showing a spacer assembly 170 and a cartridge body 31 comprising a compression gauge cartridge, broken away and sectioned apart, in an embodiment of the present invention, cartridge body 31 may be configured to include a cavity 175 for housing a spacer assembly 170 comprising a spacer member 171, a stopper 172, a spacer spring 173 and a stopper spring 174. Cavity 175 may comprise a spacer channel 176 disposed substantially perpendicularly to tissue supporting surface 34 of cartridge body 31 with one end open to tissue supporting surface 34 for passage of spacer member 171 and the other end closed, and a stopper channel 177 disposed to intersect spacer channel 176 substantially perpendicularly thereto in one end and closed in the other end. Spacer member 171 may be of rigid construction and configured to slidably engage spacer channel 176 to enable smooth and substantially precise movement along the length of spacer channel 176. Stopper 172 may be configured to slidably engage stopper channel 177 to enable smooth and substantially precise movement along the length of stopper channel 177. Disposed in spacer channel 176 between the closed end thereof and spacer member 171, spacer spring 173 may be configured to bias spacer member 171 to move in the direction of the open end of spacer channel 176. Disposed in spacer channel 177 between the closed end thereof and stopper 172, stopper spring 174 may be configured to bias stopper 172 to move in the direction of the open end of stopper channel 177 toward spacer channel 176 normally keeps stopper 172 in close contact with and/or in the path of spacer member 171 in spacer channel 176 as shown in FIG. 26A.

Figure 26A:
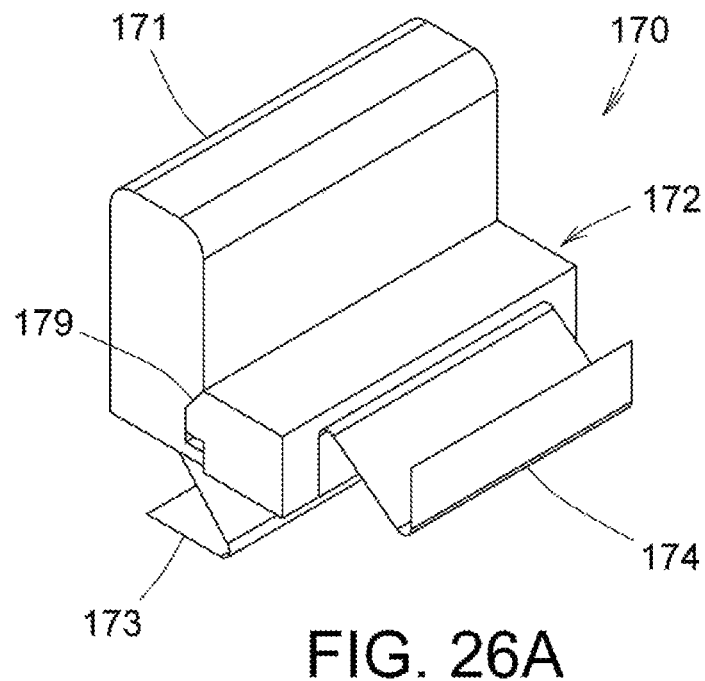
FIG. 26A is a perspective view of a spacer assembly with the stopper in the path of the spacer member according to an embodiment of the present invention.
Figure 26B:
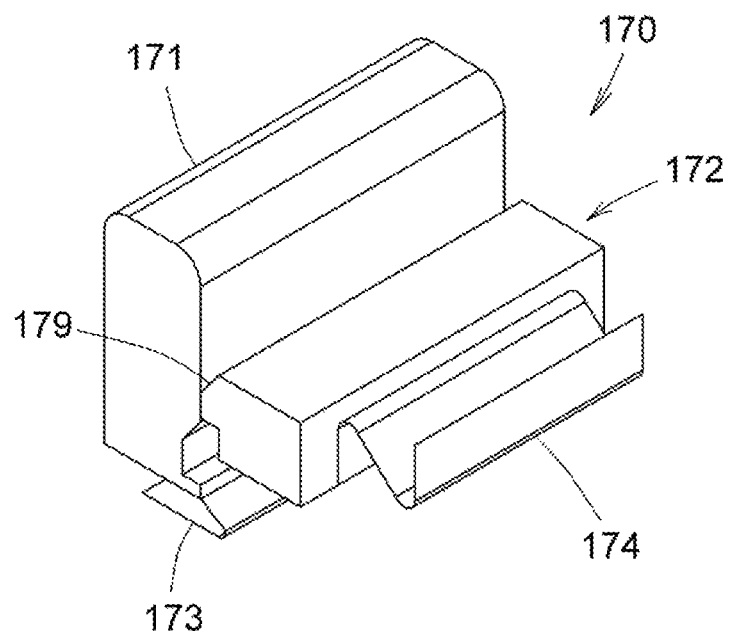
FIG. 26B is a perspective view of a spacer assembly with the stopper out of the path of the spacer member according to an embodiment of the present invention.
Figure 27:
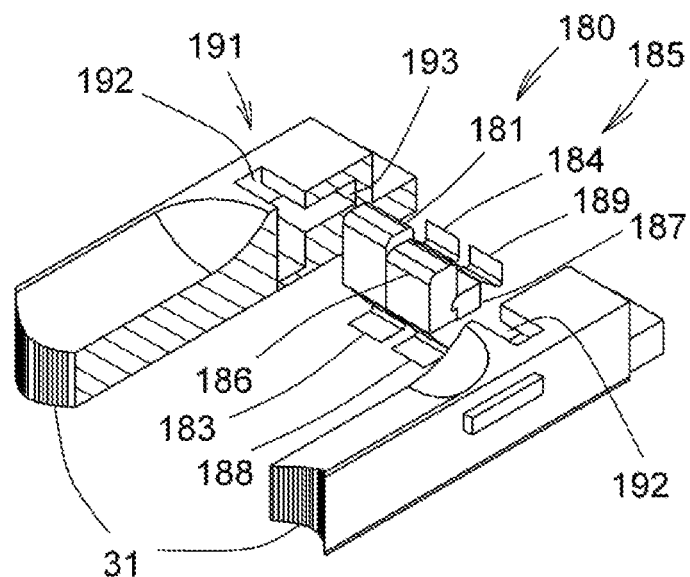
FIG. 27 is a perspective view of a cartridge body, partially broken away, and sectioned and spaced apart, and a plurality of spacer assemblies according to an embodiment of the present invention.

In an embodiment an interface 179 of stopper 172 with spacer member 171 may be configured so that spacer member 171 traveling down spacer channel 176 toward the closed end thereof, for example, driven by closing action of the two jaw members of end effector of the compression gauge instrument, causes stopper 172 to retract into stopper channel 177 toward the closed end thereof as shown in FIG. 26B. Preferably, the strength or spring constant of stopper spring 174 may be such that a magnitude of force required to be applied to stopper 172 by the anvil jaw member to retract stopper 171 (referred to as a threshold force hereinafter) is substantially higher than that of the reactionary load from the compressed tissue between the two jaw members of the compression gauge instrument to enable the physician operator operating the compression gauge instrument by the handle to sense that the two jaw members reached a predetermined gap distance there-between corresponding to the height of spacer member 171. In the path of spacer member 171, as shown in FIG. 26A, stopper 172 substantially rigidly holds spacer member 171 in position extended above tissue supporting surface 34 of cartridge body 31 at a predetermined height maintaining relative positional relationship of the two jaw members of end effector of the compression gauge instrument closed to compress a tissue captured there-between. Out of the path of spacer member 171, as shown in FIG. 26B, stopper 172 allows spacer member 171 to be retracted to or below a height above tissue supporting surface 34 of cartridge body 31 necessary for the two jaw members to be closed sufficiently to allow the end effector of the compression gauge instrument to pass through a trocar. In an embodiment the spacer member and stopper may be further configured to include an arrangement to stop the spacer member from being ejected clear out of the spacer channel by the spacer spring. In an alternate embodiment the cavity of the cartridge body may be configured with an arrangement to stop the spacer member from being ejected clear out of the spacer channel by the spacer spring.

Figure 28A:
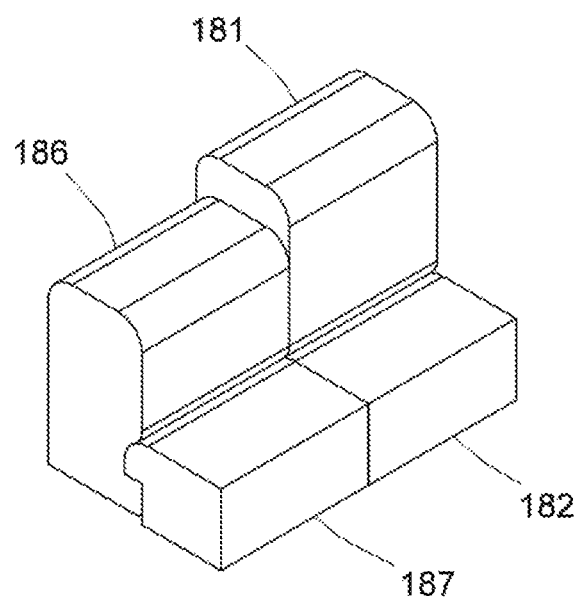
FIGS. 28A-28C are perspective views of a plurality of spacer assemblies according to an embodiment of the present invention.
Figure 28B:
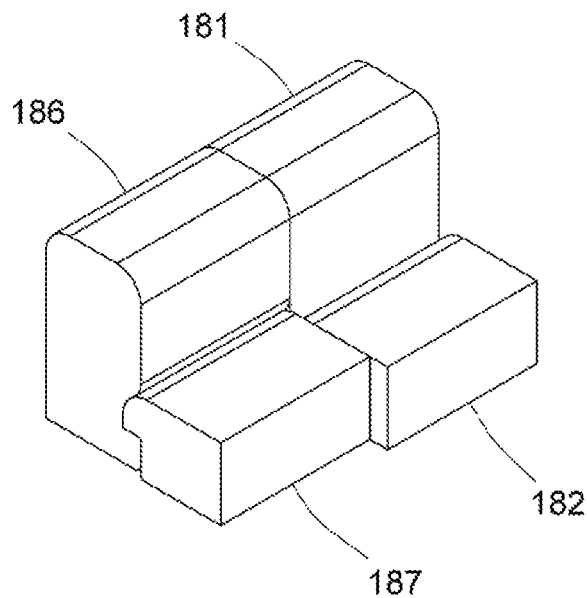
Figure 28C:
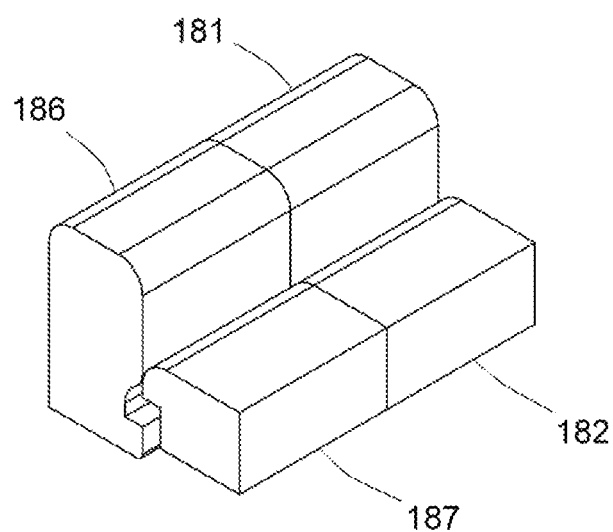

Referring to FIGS. 27 and 28A-28C showing spacer assemblies 180, 185 and a cartridge body 31 comprising a compression gauge cartridge, broken away and sectioned apart, in an embodiment of the present invention, cartridge body 31 may be configured to include a cavity 191 comprising spacer channel 192 and stopper channel 193 for housing spacer assemblies 180, 185, as described in the preceding in relation to FIGS. 25, 26A and 26B, comprising a spacer members 181, 186, respectively. In an embodiment of the present invention spacer assemblies 180, 185 may be of substantially rigid construction except spacer members 181, 186 that are configured to have different lengths along the length of spacer channel 192 or different heights the difference of which corresponds to difference in the gap distance between the two jaw members separated by spacer members 181, 186 or corresponding difference in the tissue thicknesses captured and compressed by the two jaw members. In operation the two jaw members are first held apart at a first predetermined gap distance there-between by spacer member 181 as shown in FIG. 28A. Upon application of a first threshold force by the physician operator of the compression gauge instrument stopper 182 and spacer member 181 retract and the jaw members are closed to and held apart at a second predetermined gap distance by spacer member 186 as shown in FIG. 28B. Upon further application of a second threshold force by the physician operator stopper 187 retracts and spacer members 181, 186 are free to be retracted for further closure of the two jaw members in preparation for withdrawal of the compression gauge instrument through a trocar as shown in FIG. 28C.

Figure 29:
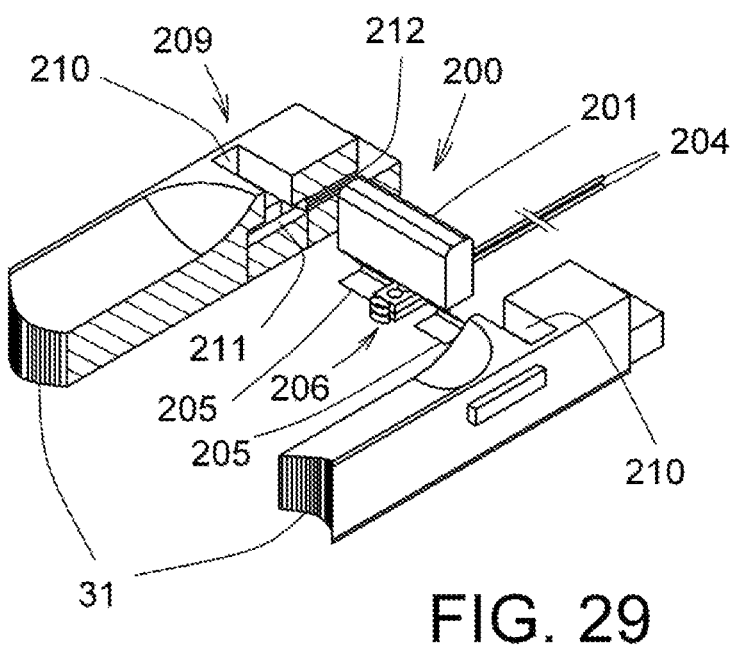
FIG. 29 is a perspective view of a cartridge body, partially broken away, and sectioned and spaced apart, and a spacer assembly according to an embodiment of the present invention.
Figure 30:
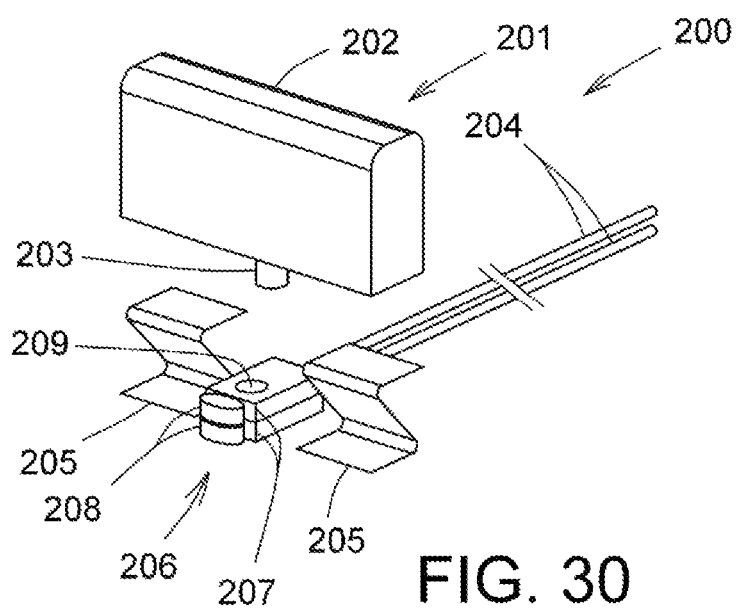
FIG. 30 is an exploded view of a spacer assembly according to an embodiment of the present invention.
Figure 31A:
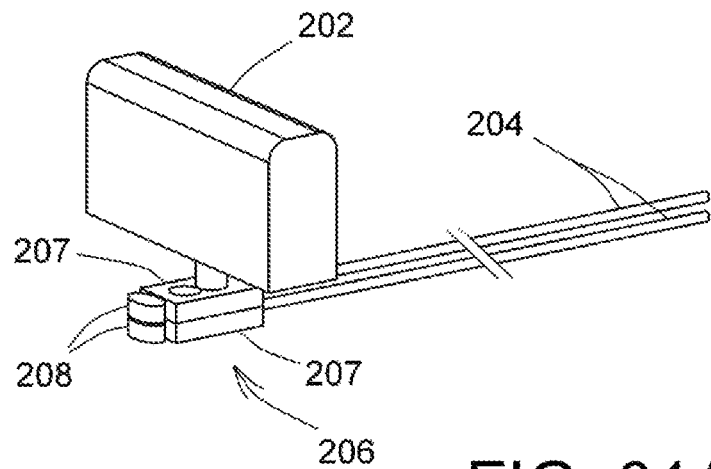
FIGS. 31A-31C are perspective views of a spacer assembly according to an embodiment of the present invention.
Figure 31B:
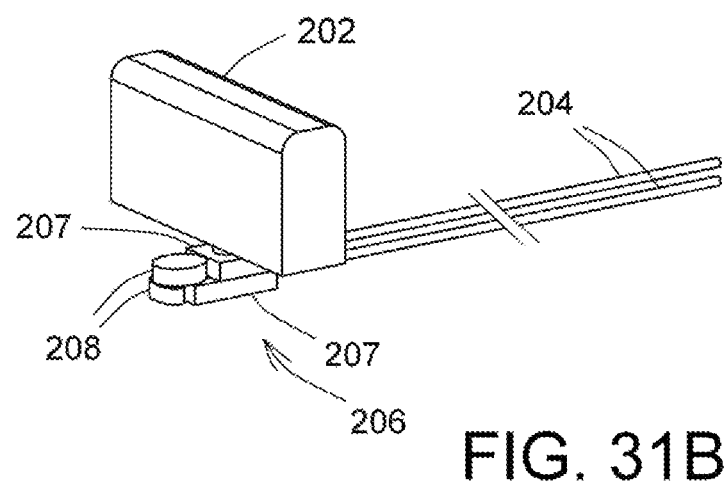
Figure 31C:
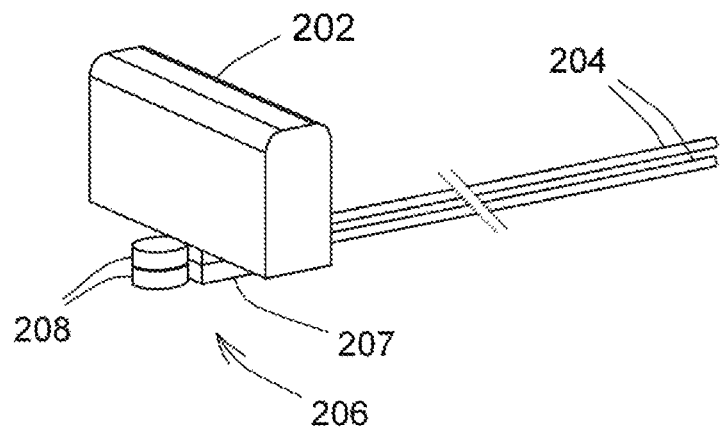

Referring to FIG. 29 showing a spacer assembly 200 and a cartridge body 31 comprising a compression gauge cartridge, broken away and sectioned apart and FIG. 30 showing spacer assembly in an exploded view, in an embodiment of the present invention, cartridge body 31 may be configured to include a cavity 209 for housing spacer assembly 200 comprising a spacer member 201, a stopper stack 206 comprising at least one stopper 207, operatively joined with a stopper control link 204, stacked on top of one another and a stopper spring 208, and a spacer spring 205. Cavity 209 may comprise a spacer channel 210 disposed substantially perpendicularly to tissue supporting surface 34 of cartridge body 31 with one end open to tissue supporting surface 34 for passage of spacer member 201, and a portion of the other end open to a stopper channel 211 and the rest of the other end closed, and stopper channel 211 disposed to intersect spacer channel 210 substantially perpendicularly thereto closed in one end that may include passages 212 for stopper control link 204 in the other end. Spacer member 201 may be configured to slidably engage spacer channel 210 to enable smooth and substantially precise movement along the length of spacer channel 210. Stopper 207 may be configured to slidably engage stopper channel 211 to enable smooth and substantially precise movement along the length of stopper channel 211. Disposed in spacer channel 210 between the closed portion of the end thereof opposite tissue supporting surface 34 and spacer member 201, spacer spring 205 may be configured to bias spacer member 201 to move in the direction of the open end of spacer channel 210. In an embodiment spacer member 201 may be of rigid construction and comprises a spacer body 202 and a spacer stem 203 fixedly joined therewith facing the closed end of spacer channel 210. In an embodiment stopper 207 may be of substantially planar shape of a predetermined thickness and of rigid construction capable of supporting and substantially precisely maintaining spacer member 201 in position under a load from the anvil jaw member. Preferably the length of spacer stem 203 may be configured to be equal to or longer the combined thickness of stoppers 207. Stopper 207 comprises a through hole 209 dimensioned to receive spacer stem 203 of spacer member 201 and, in an embodiment, at least one stoppers 207 are stacked initially with through holes 209 aligned with one another. Sliding movement of stopper 207 in stopper channel 211 may be controlled by stopper control link 204 in similar fashion to how stopper 142 is controlled by stopper control link 143 as described previously referring to FIG. 21. In an embodiment stopper 207 may be biased by stopper spring 208 to return to initial position, as described in FIG. 30 in an embodiment, following a control motion applied to stopper 207 by stopper control link 204. In an embodiment operation of spacer assembly 200 is described hereinafter referring to FIGS. 31A-31C. Initially, stoppers 207 comprising stopper stack 206 may be disposed with through holes 209 aligned with one another but not with spacer stem 203 of spacer member 201 as shown in FIG. 31A rigidly supporting and holding spacer body 202 in position at a predetermined vertical extent or height above the tissue supporting surface of the cartridge body even under a load from the anvil jaw member. In next step the physician operator operates on stopper control link 204 joined with the top most, i.e., the one in contact with spacer stem 203 of spacer member 201 to position through hole 209 thereof to be aligned with spacer stem 203 as shown in FIG. 31B in an embodiment. Under a load from the anvil jaw member spacer stem 203 of spacer member 201 falls into through hole 209 of the top most stopper 207 and spacer stem 203 now rests on the second to the top most stopper 207 and the vertical extent or height thereof above the tissue supporting surface of the cartridge body is reduced by the thickness of the top most stopper 207. In an embodiment similar operation by the physician operator may be performed on the second to the top most stopper 207 to further reduce the vertical extent or height of spacer body 202 above the tissue supporting surface of the cartridge body by the thickness thereof as shown in FIG. 31C.

Figure 32:
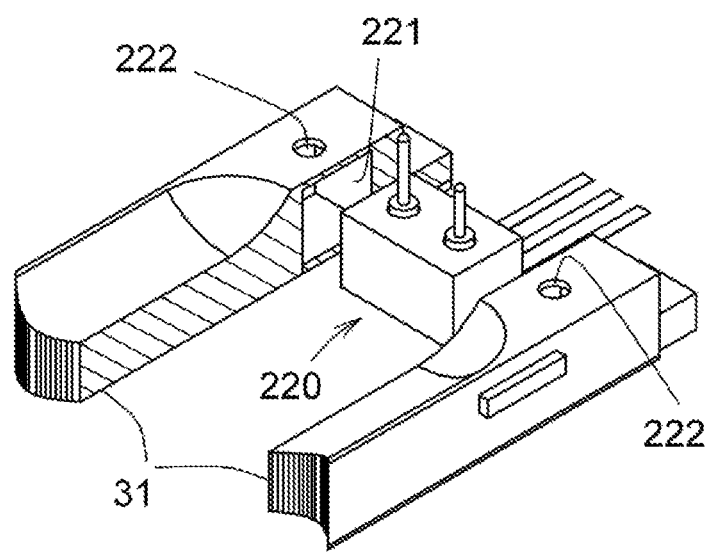
FIG. 32 is a perspective view of a cartridge body, partially broken away, and sectioned and spaced apart, and a gap sensor according to an embodiment of the present invention.
Figure 33:
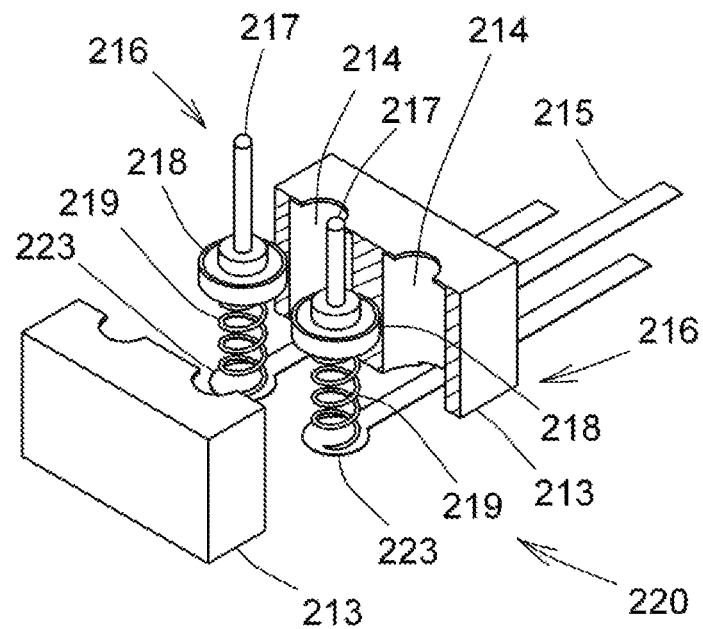
FIG. 33 is an exploded view of a gap sensor according to an embodiment of the present invention.
Figure 34:
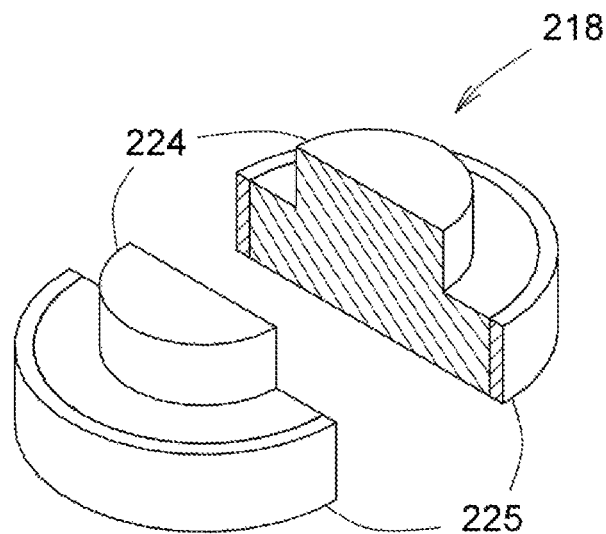
FIG. 34 is a perspective view of a piston comprising a gap sensor sectioned apart according to an embodiment of the present invention.

Referring to FIG. 32 showing a gap sensor 220 and a cartridge body 31 comprising a compression gauge cartridge broken away and sectioned apart and FIG. 33 showing gap sensor 220 in an exploded view, in an embodiment of the present invention, cartridge body 31 may be configured to include a cavity 221 having at least one through hole 222 in the tissue supporting surface of cartridge body 31 for housing gap sensor 220 for providing an electrical signal indicative of the gap distance or angular positional relationship between the two jaw members of end effector of a surgical stapler instrument instrumented with the compression gauge cartridge or a surgical compression gauge instrument. In an embodiment, as shown in detail in FIG. 33, gap sensor 220 may comprise a sensor housing 213, made up of electrically conducting material, with a housing electrode 215 attached thereto including at least one elongated chamber 214, disposed substantially perpendicularly to the tissue supporting surface of the cartridge body and having an opening substantially aligned with at least one through hole 222, for receiving a plunger assembly 216. In an embodiment plunger assembly 216 may comprise a piston 218, preferably configured to slidably engage elongated chamber 214 to enable smooth and substantially precise movement along the length thereof, a piston extension 217, a piston spring 219 and a piston electrode 223. As shown in FIG. 34, in an embodiment piston 218 may be configured to have an electrically conducting piston core 224 lined by an electrical insulation 225 along the perimeter thereof to electrically isolate piston core 224 from sensor housing 213. In an embodiment piston spring 219 is disposed between piston electrode 223 and piston 218 and configured to bias piston 218 in the direction of the tissue supporting surface normally keeping piston core 224 of piston 218 in electrical contact with sensor housing 213. Preferably, piston spring 219 may be made of electrically conducting material in order to establish an electrical connection between piston core 224 and piston electrode 223, and complete a circuit from housing electrode 215 to piston electrode 223.

In an embodiment piston extension 217 may be configured to extend from piston 218 passing through the opening in chamber 214 and at least one through hole 222 and protrude above the tissue supporting surface of cartridge body 31 to a predetermined height, and constructed to be substantially rigid to be able to conduct a load from the anvil jaw member to piston 218 as the two jaw members of the compression gauge instrument are being closed. Preferably, piston extension 217 may be made of electrically non-conducting material to electrically isolate piston core 224 from the anvil jaw member conventionally made of metal. As the closing anvil jaw member reaches and begins to depress piston extension 217 piston core 224 detaches from housing 213 breaking off electrical contact between housing electrode 215 and piston electrode 223 generating an electrical signal in the form of broken electrical continuity just like an ordinary electrical switch being turned off. Preferably, the strength or spring constant of piston spring 219 may be such that a magnitude of force required to be piston extension 217 by the anvil jaw member to force piston 218 to retract is substantially higher than that of the reactionary load from the compressed tissue between the two jaw members of the compression gauge instrument to enable the physician operator operating the compression gauge instrument by the handle to sense that the two jaw members reached a predetermined gap distance there-between corresponding to the height of piston extension 217. The generated signal indicates that the two jaw members reached a predetermined gap distance there-between corresponding to the predetermined height of piston extension 217. In an embodiment there is provided a gap sensor 220, capable of generating signals at a plurality of predetermined gap distances between the two jaw members, comprising a plurality of piston assemblies 216 with piston extension 217 of different height from one another. It is to be understood that gap sensor 220 represents but one exemplary embodiment of a sensor configuration relying on electrical switching for sensing a gap distance between the two jaw members. Numerous other configurations of electrical switch, well known to those of skill in the art, may be employed to construct a gap sensor for generating electrical signal indicative of the gap distance between the two jaw members. In an embodiment an electrical switch gap sensor may be configured to generate signal in the form of established electrical continuity, i.e., just like an electric switch being turned on. In an embodiment a gap sensor may be configured to generate an electrical or electronic signal varying continuously to correspond to continuous change in the gap distance between the two jaw members being closed. In an embodiment there is provided a processor for receiving and processing a signal from a gap sensor and a signal from the force transducer comprising the compression gauge cartridge and producing correlated set of data representative of gap distance and reactionary loads from the compressed tissue, and a display for presenting the results. In an alternate embodiment the processor may be further provided with capability to project a reactionary load at a predetermined gap distance, outside the capability of the compression gauge instrument, based on the correlated data set and known mechanical properties of the subject tissue.

Figure 35:
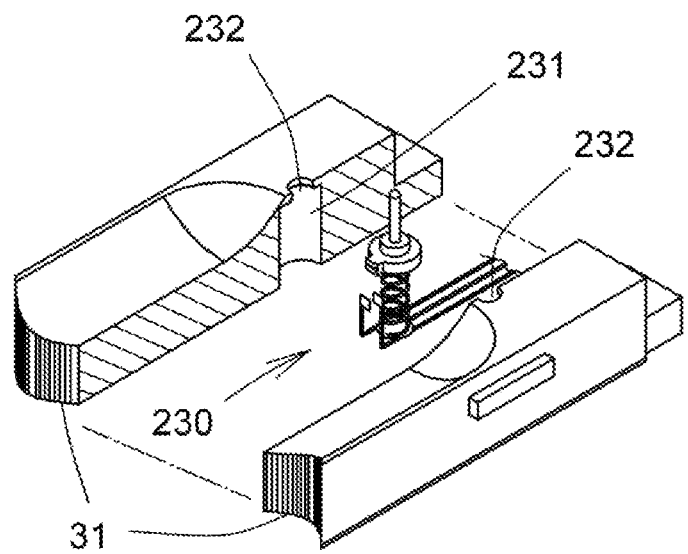
FIG. 35 is a perspective view of a cartridge body, partially broken away, and sectioned and spaced apart, and a gap sensor according to an embodiment of the present invention.
Figure 36:
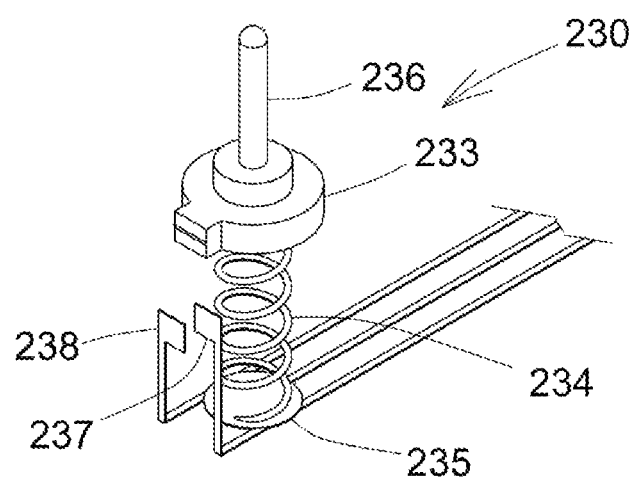
FIG. 36 is a perspective view of a gap sensor according to an embodiment of the present invention.

Referring to FIG. 35 showing in perspective view a gap sensor 230 and a cartridge body 31 comprising a compression gauge cartridge broken away and sectioned apart and FIG. 36 showing in perspective view gap sensor 230 in detail, in an embodiment of the present invention, cartridge body 31 may be configured to include a cavity 231 having a through hole 232 in the tissue supporting surface of cartridge body 31, disposed substantially perpendicularly to the tissue supporting surface of cartridge body 31, for housing gap sensor 230 for providing electrical signals indicative of the gap distance or angular positional relationship between the two jaw members of end effector of a surgical stapler instrument instrumented with the compression gauge cartridge or a surgical compression gauge instrument comprising a compression gauge jaw member comprising gap sensor 230. In an embodiment, as shown in detail in FIG. 36, gap sensor 230 may comprise a piston 233, made up of electrically conducting material and preferably configured to slidably engage cavity 231 to enable smooth and substantially precise movement along the length thereof, a piston spring 234, made up of electrically conducting material, a piston electrode 235, and a piston extension 236, made up of electrically non-conducting or insulating material. There are provided at least one sensor electrode 237, 238 disposed immediately adjacent to cavity 231 arranged such that piston 233 comes into electrical contact therewith during movement in cavity 231. In an embodiment piston spring 234 is disposed between piston electrode 235 and piston 233 to provide an electrical contact there-between and configured to bias piston 233 in the direction of the tissue supporting surface normally keeping piston 233 separated and electrically isolated from sensor electrodes 237, 238. In an embodiment the position of the first point of contact of sensor electrode 237, disposed closest to piston 233, with piston 233 is predetermined, with piston extension 236 of predetermined dimension in the direction of piston movement, to correspond to a first predetermined gap distance between the two jaw members of a surgical stapler instrumented with the compression gauge cartridge or a surgical compression gauge instrument. In an embodiment the distance between the first points of contact of two neighboring sensor electrodes is predetermined to correspond to incremental difference between two predetermined gap distances between the two jaw members of a surgical stapler instrumented with the compression gauge cartridge or a surgical compression gauge instrument.

In an embodiment piston extension 236 may be configured to extend from piston 233 passing through hole 232 and protrude above the tissue supporting surface of cartridge body 31 to a predetermined height, and constructed to be substantially rigid to be able to transfer a load from the anvil jaw member to piston 233 as the two jaw members of end effector are being closed. Preferably, piston extension 236 may be made of electrically non-conducting material to electrically isolate piston 233 from the anvil jaw member conventionally made of metal. As the closing anvil jaw member reaches and begins to depress piston extension 236 piston 233 slides down cavity 231 to reach sensor electrode 237 disposed closest to piston 233, with piston spring 234 in fully extended position, making electrical contact therewith and generating an electrical signal in the form of electrical continuity between piston electrode 235 and sensor electrode 237 just like an ordinary electrical switch being turned on. The generated signal indicates that the two jaw members reached a first predetermined gap distance there-between corresponding to the position of the first point of contact of sensor electrode 237. As the anvil jaw continues to close piston 233 reaches sensor electrode 238, disposed second closest to piston 233, making electrical contact therewith and generating an electrical signal in the form of electrical continuity between piston electrode 235 and sensor electrode 238. The generated signal indicates that the two jaw members reached a second predetermined gap distance there-between corresponding to the position of the first point of contact of sensor electrode 238.

Figure 37:
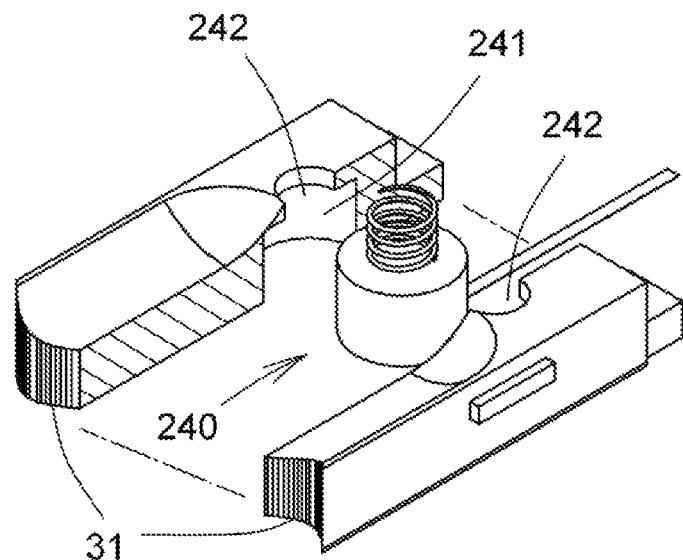
FIG. 37 is a perspective view of a cartridge body, partially broken away, and sectioned and spaced apart, and a gap sensor according to an embodiment of the present invention.
Figure 38:
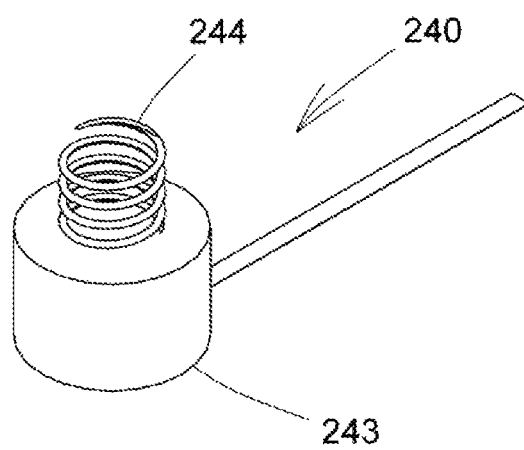
FIG. 38 is a perspective view of a gap sensor according to an embodiment of the present invention.

Referring to FIG. 37 showing in perspective view a gap sensor 240 and a cartridge body 31 comprising a compression gauge cartridge broken away and sectioned apart and FIG. 38 showing in perspective view gap sensor 240 in detail, in an embodiment of the present invention, cartridge body 31 may be configured to include a cavity 241 having a through hole 242 in the tissue supporting surface of cartridge body 31, disposed substantially perpendicularly to the tissue supporting surface of cartridge body 31, for housing gap sensor 240 for providing electrical signal indicative of the gap distance or angular positional relationship between the two jaw members of end effector of a surgical stapler instrument instrumented with the compression gauge cartridge or a surgical compression gauge instrument comprising a compression gauge jaw member comprising gap sensor 240. In an embodiment, as shown in detail in FIG. 38, gap sensor 240 may comprise a force transducer 243 housed in cavity 241 and a sensor spring 244 disposed to rest on the sensitivity or loading area of force transducer 243, where a load to be measured needs to be applied to, on the one end and to extend via through hole 242 above the tissue supporting surface on the other end, which is configured to come in contact with and be depressed by the anvil jaw member as the two jaw members are closed. In an embodiment sensor spring 244 may be calibrated to exert a load, to a predetermined precision, to the loading area of force transducer 243 proportional to change in length thereof occurring when depressed by the closing anvil jaw member. Preferably, there is provided a processor, to which the output signal of force transducer 243 is connected to, which is configured to analyze the output signal and extract corresponding gap distance between the two jaw members for display. In an embodiment sensor spring 244 may be substituted with other elastic element calibrated to exert a load on force transducer 243 proportional to change in a dimension thereof occurring when depressed by the anvil jaw member.

Figure 39:
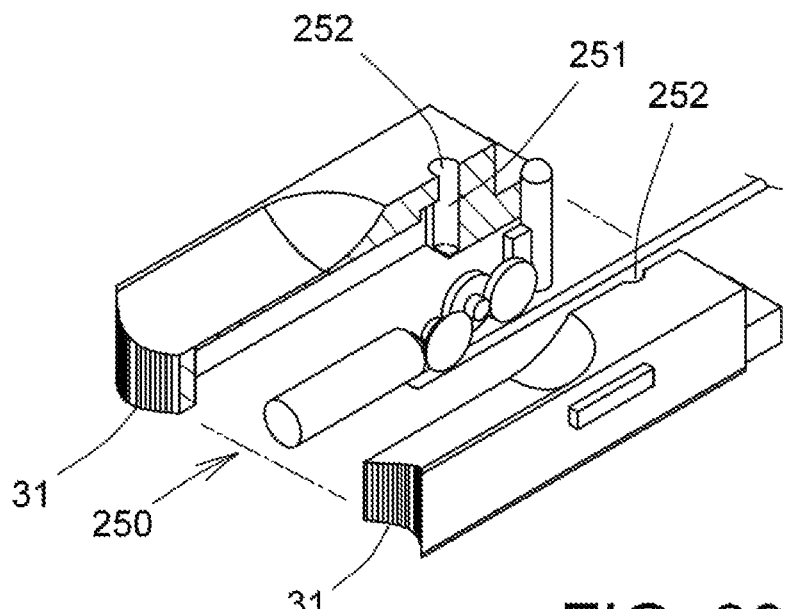
FIG. 39 is a perspective view of a cartridge body, partially broken away, and sectioned and spaced apart, and a gap sensor according to an embodiment of the present invention.
Figure 40:
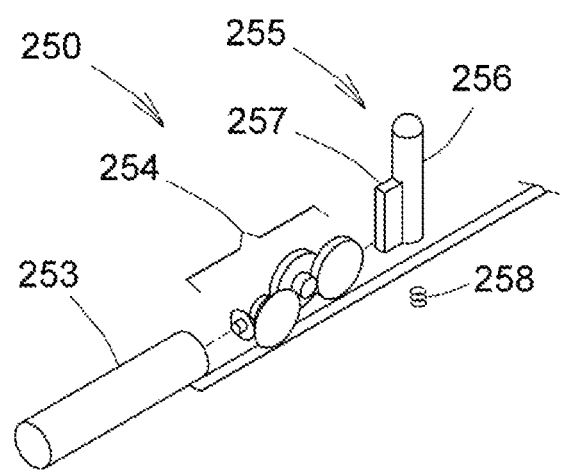
FIG. 40 is an exploded view of a gap sensor according to an embodiment of the present invention.

Referring to FIG. 39 showing in perspective view a gap sensor 250 and a cartridge body 31 comprising a compression gauge cartridge broken away and sectioned apart and FIG. 40 showing in exploded view gap sensor 250 in detail, in an embodiment of the present invention, cartridge body 31 may be configured to include a cavity 251 including an elongated chamber 252 with one end closed and the other open to the tissue supporting surface of cartridge body 31 and disposed substantially perpendicularly to the tissue supporting surface of cartridge body 31 for housing gap sensor 250 for providing electrical signals indicative of the gap distance or angular positional relationship between the two jaw members of end effector of a surgical stapler instrument instrumented with the compression gauge cartridge or a surgical compression gauge instrument comprising a compression gauge jaw member comprising gap sensor 250. In an embodiment, as shown in detail in FIG. 40, gap sensor 250 may comprise a potentiometer 253, a transmission assembly 254, a piston assembly 255 comprising a piston 256 of elongated and rigid construction, and a rack gear 257 fixedly joined with elongated piston 256 substantially along the length thereof, and a piston spring 258. Preferably piston 256 may be configured to extend past the open end of chamber 252 above the tissue supporting surface of cartridge body 31 to a predetermined extent sufficient to come in contact with the anvil jaw member at a predetermined gap distance between the two jaw members and to slidably engage chamber 252 to enable smooth and substantially precise movement along the length thereof when depressed by the anvil jaw member as the two jaw members are closed or urged by piston spring 258 toward the anvil jaw member. Piston assembly 255 is biased by piston spring 258, disposed in chamber 252 between the closed end thereof and piston 256, to move in the direction of the open end of chamber 252. In an embodiment transmission assembly 254 comprises a set of gears including a pinion gear for engaging rack gear 257 for converting linear motion of piston assembly 255 into a circular motion and a gear combination for amplifying the motion of piston assembly 255 and transferring the result of amplification in a rotary motion to potentiometer 253, well known to those of skill in the art, which is configured to convert an input rotary motion into an output voltage signal of magnitude proportional to the degree of input rotary motion. Preferably, there is provided a processor, external to the compression gauge cartridge or the surgical compression gauge instrument, for receiving and processing the output voltage signal to provide an output corresponding to the distance travelled by piston assembly 255 from which the gap distance between the two jaw members at any given point in time can be extracted.

Figure 41:
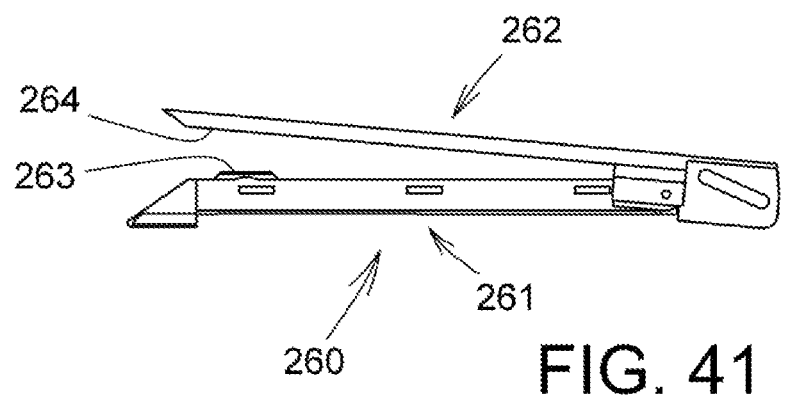
FIGS. 41-44 is a side elevation view of a compression gauge cartridge and an anvil jaw member comprising an end effector of a surgical stapler instrument instrumented with the compression gauge cartridge according to an embodiment of the present invention.
Figure 42A:
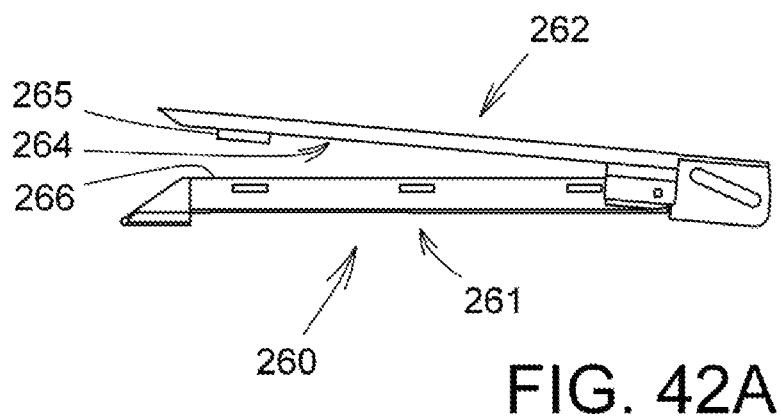
Figure 42B:
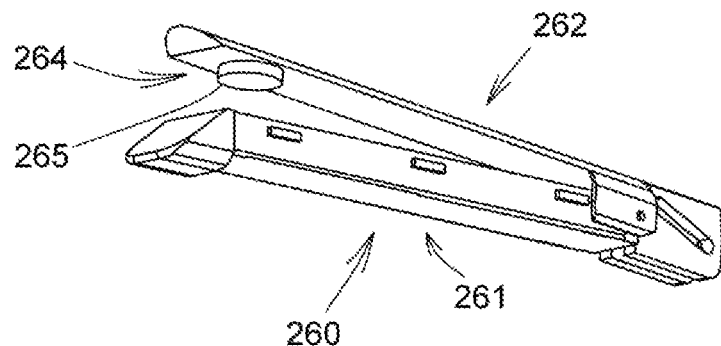
Figure 43:
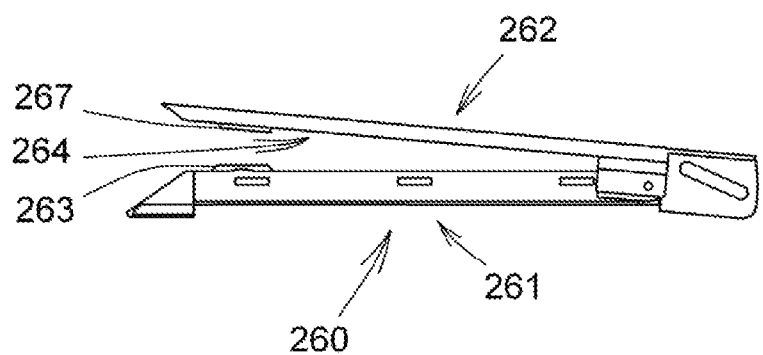
Figure 44:
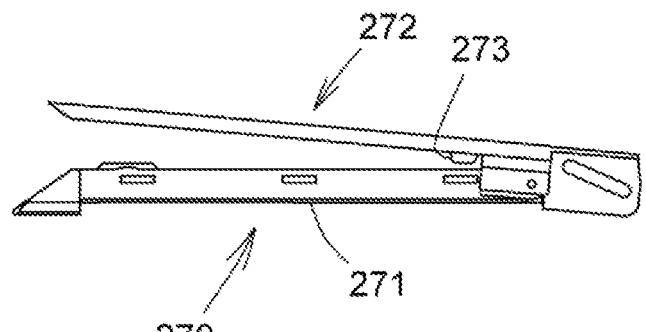

Referring to FIG. 41 showing a compression gauge cartridge 261 and an anvil jaw member 262, having a tissue contacting surface 264, comprising an end effector 260 of a surgical stapler instrument instrumented with compression gauge cartridge 261 disposed in the cartridge bay of the cartridge jaw member thereof, in an embodiment of the present invention, a tissue supporting surface 263 of compression gauge cartridge 261 may be configured to minimize compression of tissue captured between the two jaw members of end effector 260 outside the area covered by the tissue compression face of the compression head comprising the force gauge assembly comprising compression gauge cartridge 261 while tissue contacting surface 264 of anvil jaw member 262 may be configured to be substantially flat without special features thereon for reducing tissue compression. Similarly, in an embodiment, a tissue supporting surface of the compression gauge jaw member of a surgical compression gauge instrument may be configured to minimize compression of tissue captured between the two jaw members of end effector outside the area covered by the tissue compression face of the compression head comprising the force gauge assembly comprising the compression gauge jaw member while the tissue contacting surface of the anvil jaw member may be configured to be substantially flat without special features thereon for reducing tissue compression. In an alternate embodiment, as shown in FIGS. 42A and 42B, a tissue supporting surface 266 of compression gauge cartridge 261 may be configured to be substantially flat without special features thereon for reducing tissue compression and tissue contacting surface 264 of anvil jaw member 262 may be configured to include an anvil compression head 265 of a predetermined shape configured to extend from tissue contacting surface 264 of anvil jaw member 262 to minimize compression of tissue captured between the two jaw members of end effector 260 outside the area covered by the tissue compression face of the compression head. Preferably, the area over which anvil compression head 265 comes into contact with tissue is substantially equal to or larger than that of the tissue compression face of the compression head comprising the force gauge assembly comprising compression gauge cartridge 261. In another alternate embodiment, as shown in FIG. 43, a tissue supporting surface 263 of compression gauge cartridge 261 may be configured to minimize compression of tissue captured between the two jaw members of end effector 260 outside the area covered by the tissue compression face of the compression head and tissue contacting surface 264 of anvil jaw member 262 may also be configured to include an anvil compression head 267 of a predetermined shape configured to extend from tissue contacting surface 264 of anvil jaw member 262 to minimize compression of tissue captured between the two jaw members of end effector 260. Preferably, the area over which anvil compression head 267 comes into contact with tissue is substantially equal to or larger than the area of the tissue compression face of the compression head comprising the force gauge assembly comprising compression gauge cartridge 261. In an embodiment of the present invention, as shown in FIG. 44, a spacer 273 may be disposed on anvil jaw member 272 and not on compression gauge cartridge 271 comprising an end effector 270. Similarly, in an embodiment, a spacer may be disposed on the anvil jaw member and not on the compression gauge jaw member comprising an end effector.

Figure 45A:
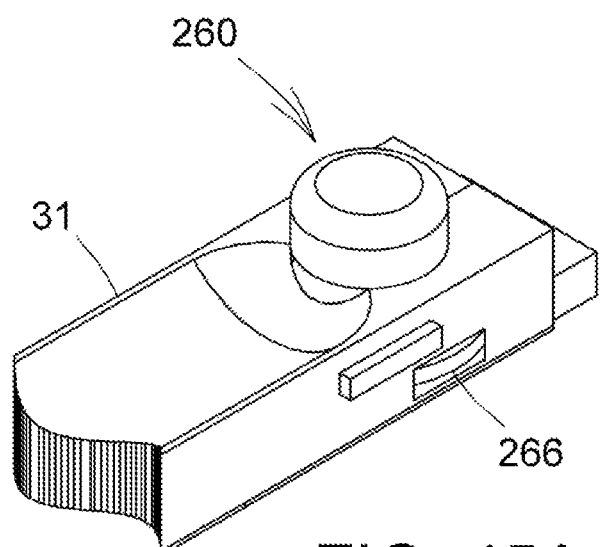
FIGS. 45A and 45B is a perspective view of a cartridge body partially broken away and partially broken away, sectioned and spaced apart, respectively, and a gap sensor according to an embodiment of the present invention.
Figure 45B:
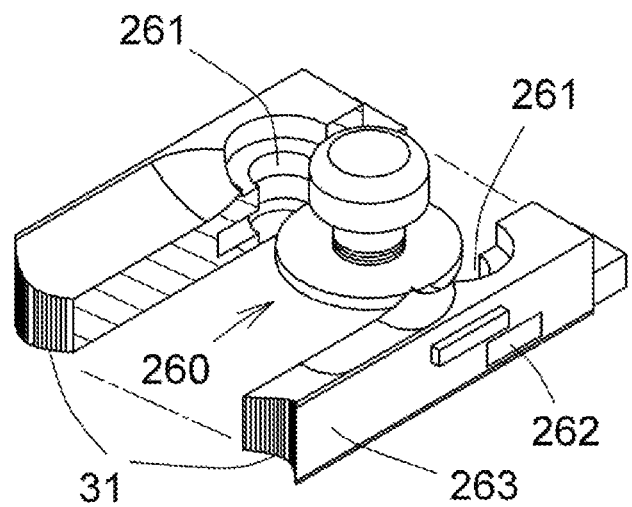
Figure 46:
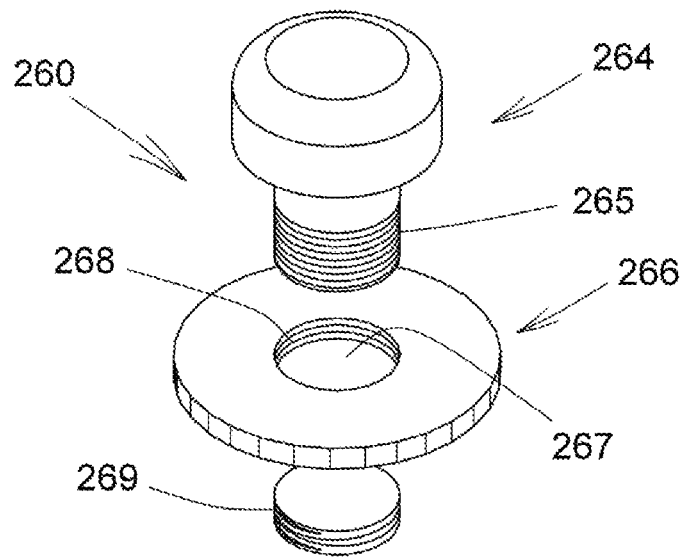
FIG. 46 is a perspective view of a gap sensor according to an embodiment of the present invention.

Referring to FIGS. 45A and 45B showing in perspective view an adjustable and retractable spacer assembly 260 and a cartridge body 31 comprising a compression gauge cartridge partially broken away and partially broken away, sectioned and spaced apart, respectively, and FIG. 46 showing in perspective view spacer assembly 260 in detail, in an embodiment of the present invention, cartridge body 31 may be configured to include a cavity 261 open to the tissue supporting surface of cartridge body 31, disposed substantially perpendicularly to the tissue supporting surface of cartridge body 31, for housing spacer assembly 260 for providing a rigid stop for maintaining a predetermined gap distance or angular positional relationship between the two jaw members of end effector of a surgical stapler instrument instrumented with the compression gauge cartridge or a surgical compression gauge instrument comprising a compression gauge jaw member comprising spacer assembly 260. In an embodiment cavity 261 may be configured to slidably engage spacer assembly 260 to enable smooth and substantially precise movement of spacer assembly 260 therein substantially perpendicularly to the tissue supporting surface of cartridge body 31. In an embodiment, as shown in detail in FIG. 46, spacer assembly 260 may comprise a spacer member 264 of rigid construction having a threaded portion 265 of a gender, a thumb wheel 266 having a through hole 267 with a matching thread 268 of opposite gender to that of threaded portion 265 for receiving spacer member 264 with threaded portion 265 rotatably engaging matching thread 268 and a spacer spring 269. Preferably, thumb wheel 266 may be configured to be partially exposed through a side 263 of cartridge body 31 to allow manipulation by a physician operator. Preferably spacer member 264 may be configured to extend past the opening of cavity 261 above the tissue supporting surface of cartridge body 31 to a predetermined extent sufficient to come in contact with the anvil jaw member at a predetermined gap distance between the two jaw members and spacer spring 269 may be disposed to bias spacer assembly 264 to move in the direction of the opening of cavity 261. In an embodiment the distance above the tissue supporting surface spacer member 264 extends may be adjusted by turning thumb wheel 266 which drives spacer member 264 up and down cavity 261 via the rotatable, threaded engagement between thumb wheel 266 and spacer member 264. When spacer member 264 is depressed by the anvil jaw member as the two jaw members are closed or urged by spacer spring 269 toward the anvil jaw member spacer assembly 260 moves along cavity 261 smoothly and substantially precisely allowing spacer assembly 260 to be retracted into cavity 261, preferably, sufficiently for the two jaw members comprising end effector to be closed and be able to pass through a trocar. Preferably, the strength or spring constant of spacer spring 269 may be such that a magnitude of force required to be applied to spacer member 264 by the anvil jaw member to cause spacer assembly 260 to retract is substantially higher than that of the reactionary load from the compressed tissue between the two jaw members of the compression gauge instrument to enable the physician operator to be able sense that the two jaw members reached a predetermined gap distance corresponding to the extent or height of spacer member 264 above the tissue supporting surface of cartridge boy 31.

In an embodiment of the present invention there is provided a surgical instrument with an end effector comprising a pair of jaw members pivotally engaged with each other through a pivot mechanism, which open and close when driven by a drive mechanism associated with handle operated by a physician, for example, to capture a tissue therebetween, with one of the jaw members instrumented with a spacer assembly comprising a spacer member and a base or a spacer base for maintaining a predetermined gap distance or relative angular positional relationship between the two jaw members when the two jaw members are closed. In an embodiment one of the two jaw members comprising the end effector of the surgical instrument may be an anvil jaw member and the other a compression gauge jaw member comprising a spacer assembly and a force gauge assembly comprising a force transducer and a compression head. The surgical instrument may further comprise a mechanism for controlling the position of the spacer base that may be operated by a physician to select the gap distance between the two jaw members.

Figure 47:
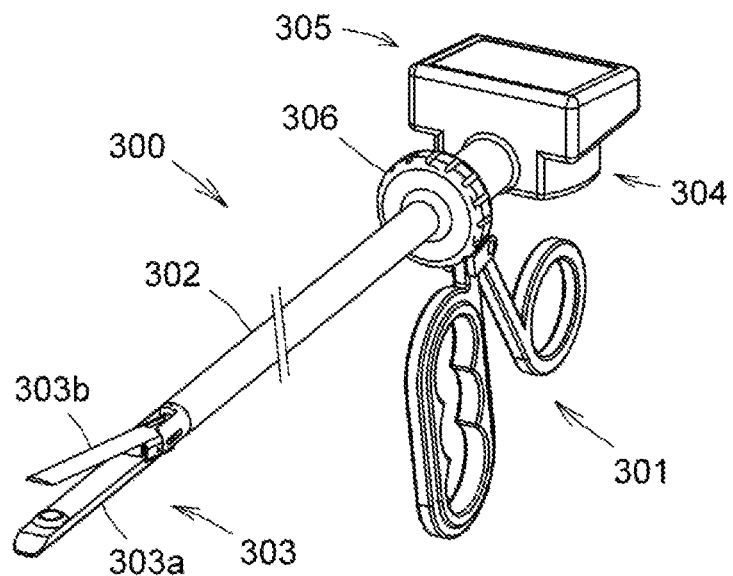
FIG. 47 is a perspective view of a surgical instrument according to an embodiment of the present invention.
Figure 48:
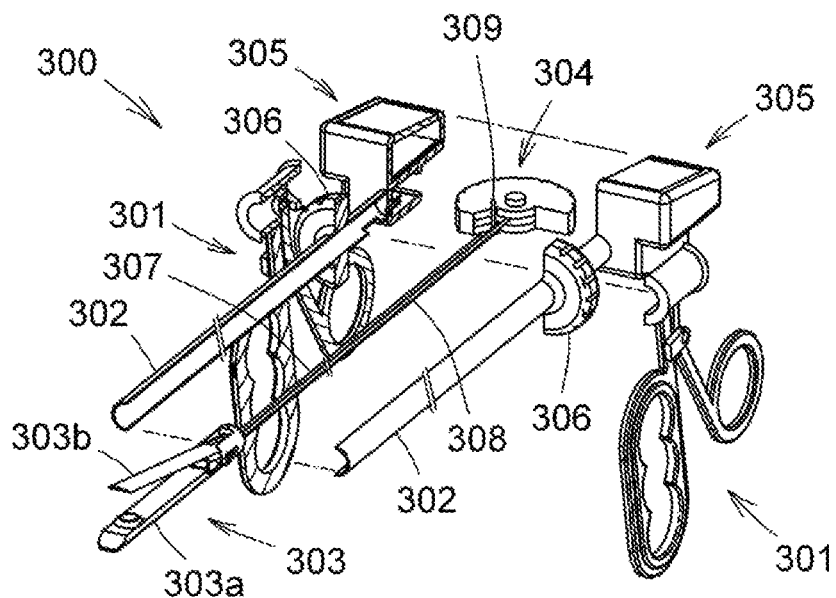
FIG. 48 is a perspective view of a surgical instrument, shown in FIG. 47, partially sectioned apart according to an embodiment of the present invention.
Figure 49:
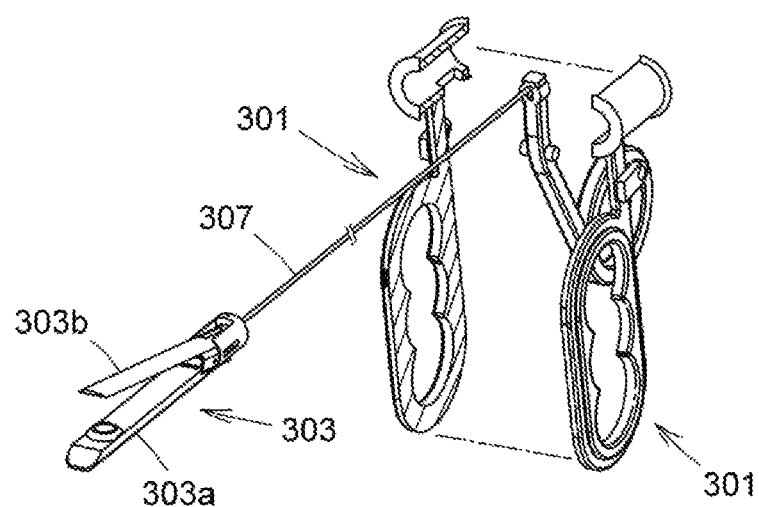
FIG. 49 is a perspective view of a part of a surgical instrument, shown in FIG. 47, partially sectioned apart according to an embodiment of the present invention.
Figure 50:
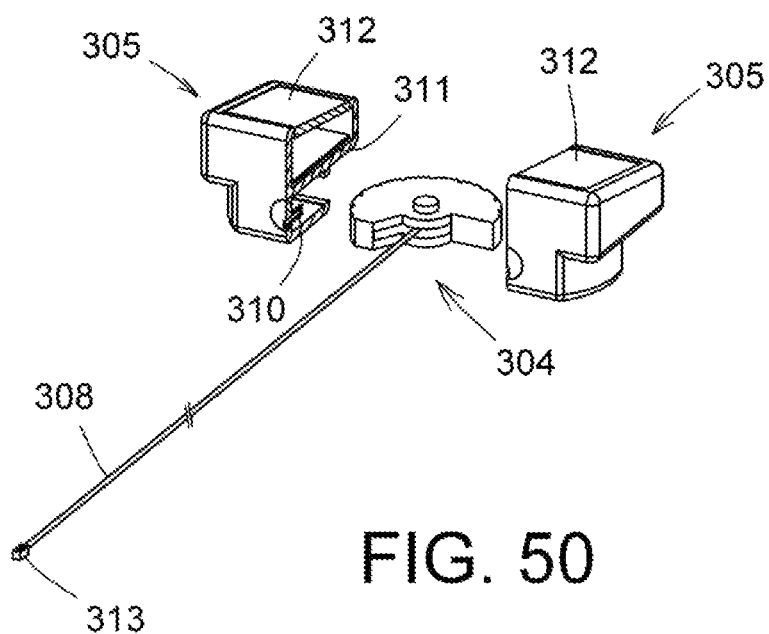
FIG. 50 is a perspective view of a part of a surgical instrument, shown in FIG. 47, partially sectioned apart according to an embodiment of the present invention.
Figure 51:
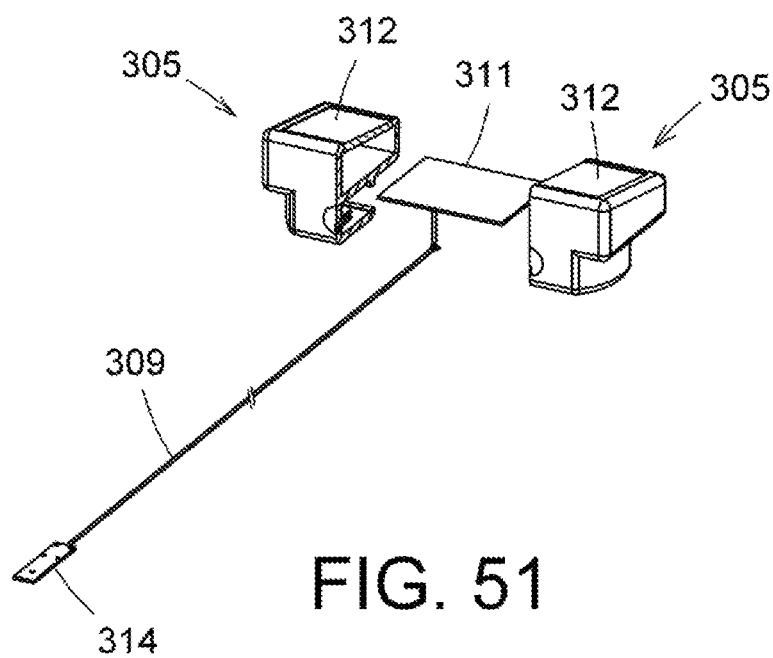
FIG. 51 is a perspective view of a part of a surgical instrument, shown in FIG. 47, partially sectioned apart according to an embodiment of the present invention.

Referring to FIGS. 47 and 48 showing, in an embodiment of the present invention, a surgical instrument 300 in perspective view and a surgical instrument partially sectioned and spaced apart, respectively, for use in a surgical operation, surgical instrument 300 may comprise a handle 301, an elongated shaft 302 extending distally from handle 301 and having a proximal end and a distal end, an end effector 303 supported by elongated shaft 302 at distal end thereof and comprising a pair of jaw members 303a, 303b pivotally engaged with each other, a spacer base control mechanism or a base control mechanism 304, and a signal processor and display unit 305 disposed proximally to handle 301 and at the distal end of elongated shaft 302. In an embodiment of the present invention one of the two jaw members 303a, 303b may be configured as a compression gauge jaw member instrumented with a force gauge assembly and a spacer assembly, and the other jaw member 303b may be configured as an anvil jaw member. In an embodiment the surgical instrument may further comprise a rotation wheel fixedly joined coaxially with elongated shaft 302 and elongated shaft 302 may be configured to rotate with respect to handle 301 so that a physician may rotate elongated shaft 302 along with end effector 303, spacer base control mechanism 304 and signal processor and display unit 305 about the axis or the length direction of elongated shaft 302 to aid in application of the surgical instrument. In an embodiment elongated shaft 302 may comprise a bendable section operably connected with a bending control mechanism in handle 301 to allow articulation of end effector 303 to aid in application of the surgical instrument. As shown in FIG. 48 and in detail in FIG. 49 in an embodiment of the present invention end effector 303 may be operably connected with handle 301 by an end effector control link 307 disposed in elongated shaft 302, which transfers the actuation force applied to handle 301 by a physician or a power driven actuator (see FIG. 65) in operating handle 301 to open or close the two jaw members 303a, 303b comprising end effector 303. As shown in FIG. 48 and in detail in FIG. 50 in an embodiment of the present invention spacer base control mechanism 304 may be operably connected with a spacer base 313 comprising a spacer assembly (for example, see FIGS. 54-56) by a spacer base control link 308 disposed in elongated shaft 302, which transfers the actuation force applied to spacer base control mechanism 304 by a physician or a power driven actuator (see FIG. 65) in operating spacer base control mechanism 304 to manipulate the position of spacer base 313. In an embodiment spacer base control mechanism 304 includes a guide member 310 for guiding spacer base control link 308. Detailed descriptions of various embodiments of spacer base control mechanism are provided later in this Detail Description. As shown in FIG. 50 and in detail in FIG. 51, in an embodiment of the present invention, signal processor and display unit 305 comprises a display screen 312 and an electronic circuit board 311 may be electrically connected with a force transducer 314 by a signal cable including a plurality of conductors or electrical lines for receiving output signals from and supplying power needed in operating force transducer 314. In an embodiment electronic circuit board 311 may be configured to accommodate various electronic components including a signal processor or CPU required to process output signals from force transducer 314 and to drive display screen 312, and to control power driven actuators for operating handle 301 and/or spacer base control mechanism 304 (see FIG. 65). In an embodiment the CPU may display various information produced in the course of signal processing and power driven actuator control on display screen 312 and/or on a remote display screen, for example, via wireless link. In an embodiment an electrical power needed in operating electronic circuit board 311 may be housed signal processor and display unit 305 in the form of one or more batteries. In an alternate embodiment an electrical power may be supplied from an external power source (not shown in the FIGURES).

Figure 52:
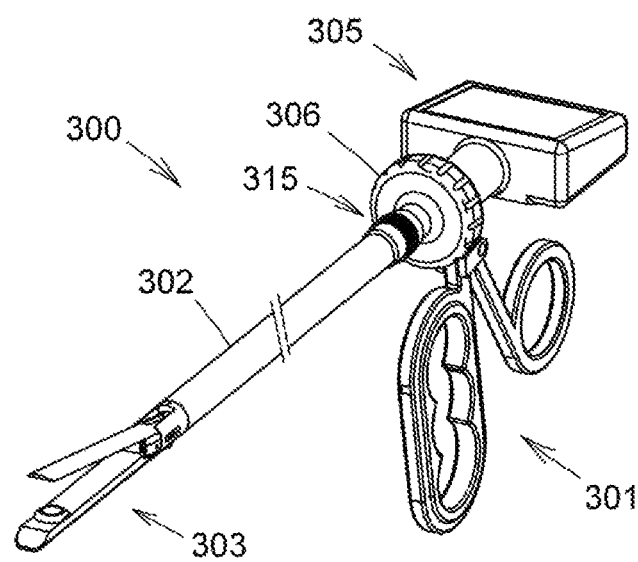
FIG. 52 is a perspective view of a surgical instrument according to another embodiment of the present invention.
Figure 53:
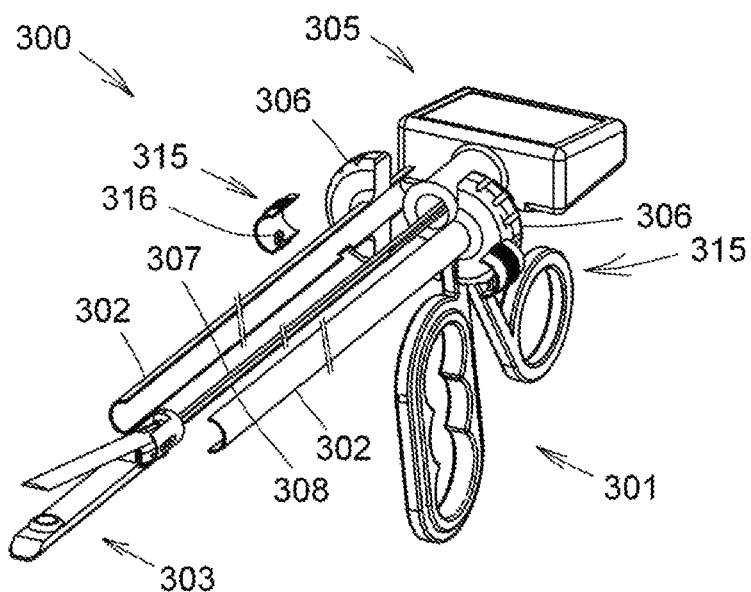
FIG. 53 is a perspective view of a surgical instrument, shown in FIG. 52, partially sectioned apart according to an embodiment of the present invention.

Referring to FIGS. 52 and 53 showing, in an alternate embodiment of the present invention, a surgical instrument 300 in perspective view and a surgical instrument partially sectioned and spaced apart, respectively, for use in a surgical operation, surgical instrument 300 may comprise a spacer base control mechanism 315 disposed distally to handle 301 and having a boss 316 for fixedly attaching spacer base control link 308, and a signal processor and display unit 305 associated with handle 301. In an embodiment spacer base control mechanism 315 may be configured as a collar slidably disposed along and around elongated shaft 302 disposed at a predetermined position along the length thereof. In FIGS. 52 and 53 the same reference characters are used as in FIGS. 47-51 to identify like elements. In an embodiment a physician operates spacer base control mechanism 315 by sliding back and forth along the length of elongated shaft 302 to impart a linear driving force to spacer base control link 308. In an embodiment the surgical instrument may further comprise a rotation wheel fixedly joined coaxially with elongated shaft 302 and elongated shaft 302 may be configured to rotate with respect to handle 301 so that a physician may rotate elongated shaft 302 along with end effector 303 and spacer base control mechanism 304 about the axis or the length direction of elongated shaft 302 to aid in application of the surgical instrument.

Figure 54:
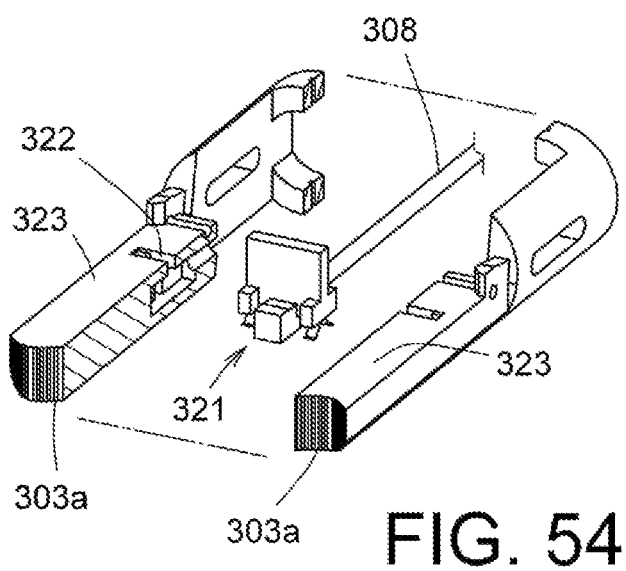
FIG. 54 is a perspective view of a compression gauge jaw member broken away and partially sectioned apart according to an embodiment of the present invention.
Figure 55:
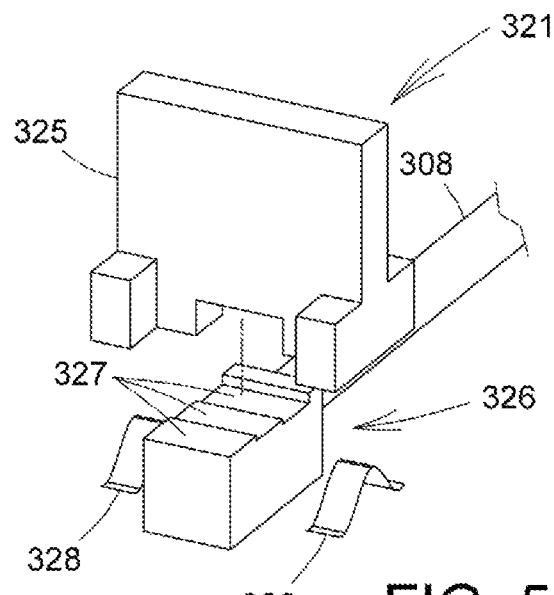
FIG. 55 is an exploded view of a spacer assembly according to an embodiment of the present invention.
Figure 56:
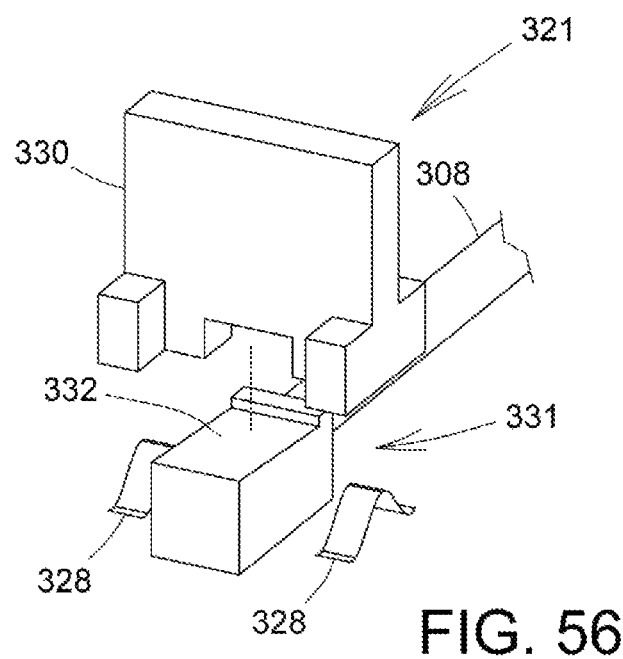
FIG. 56 is an exploded view of a spacer assembly according to another embodiment of the present invention.

In a practical implementation of a spacer assembly described previously with reference to FIGS. 21-24, FIG. 54 shows, in perspective view, a spacer assembly 321 disposed in a compression gauge jaw member 303a, shown partially broken, sectioned and spaced apart, comprising an end effector comprising a surgical instrument in an embodiment of the present invention, and FIG. 55 shows, in perspective view, spacer assembly 321 in detail. As shown in FIG. 54, in an embodiment, compression gauge jaw member 303a may be configured to include a cavity 322 open to a tissue supporting surface 323 thereof for housing spacer assembly 321 for providing a rigid stop to maintain a predetermined gap distance or angular positional relationship between the anvil and compression gauge jaw members comprising the end effector. In an embodiment, as shown in detail in FIG. 55, spacer assembly 321 may comprise a spacer member 325 of rigid construction, a spacer base 326, referred to as a stopper in describing FIGS. 21-24, of rigid construction operatively joined with spacer base control link 308 and configured to support spacer member 325 on a stepped side 327 thereof with each step corresponding to a discrete height of spacer member 325 above tissue supporting surface 323 of jaw member 303a, and spacer springs 328. In an alternate embodiment, as shown in FIG. 56, spacer base 331 may be configured to support spacer member 330 on a sloped side 332 to allow the height of spacer member 325 above tissue supporting surface 323 of jaw member 303a to be varied continuously. In an embodiment of the present invention spacer member 325, 330 and cavity 322 may be configured to allow spacer member 325, 330 to move smoothly and substantially precisely in direction substantially perpendicular to tissue supporting surface 323 of jaw member 303a and spacer base 326, 331 and cavity 322 may be configured to allow spacer base 326, 331 to move smoothly in direction substantially perpendicular to spacer member 325, 330 and parallel to supporting surface 323 of jaw member 303a. In an embodiment spacer springs 328 are configured to bias spacer member 325, 330 toward the anvil jaw member (not shown in FIG. 54). In an embodiment spacer base control link 308 may be directly joined with and configured to transfer a linear actuation force provided by a spacer base control mechanism to drive spacer base 326, 331 to move back and forth substantially linearly and parallel to tissue supporting surface 323 of jaw member 303a to change the position of spacer base 326 with respect to spacer member 325. In an alternate embodiment spacer base control link 308 may be operably joined with spacer base 326, 331 via a motion conversion means to convert, for example, an actuation force transferred via spacer base control link 308 from rotation to linear form, to drive spacer base 326, 331 to move back and forth substantially parallel to tissue supporting surface 323 of jaw member 303a. In an embodiment spacer assembly 321 may include a spring for biasing spacer base 326, 331 toward or away from spacer base control link 308. Spacer assemblies shown in FIG. 12A and FIGS. 45B and 46 are some of exemplary embodiments of spacer assembly requiring a rotation of a spacer base to adjust the height of the spacer member above the tissue supporting surface of a jaw member in which the spacer assembly is housed. Spacer assembly shown in FIGS. 29 and 31C is an exemplary embodiment of spacer assembly requiring a plurality of spacer base control links to adjust the height of the spacer member above the tissue supporting surface of a jaw member in which the spacer assembly is housed.

Figure 57:
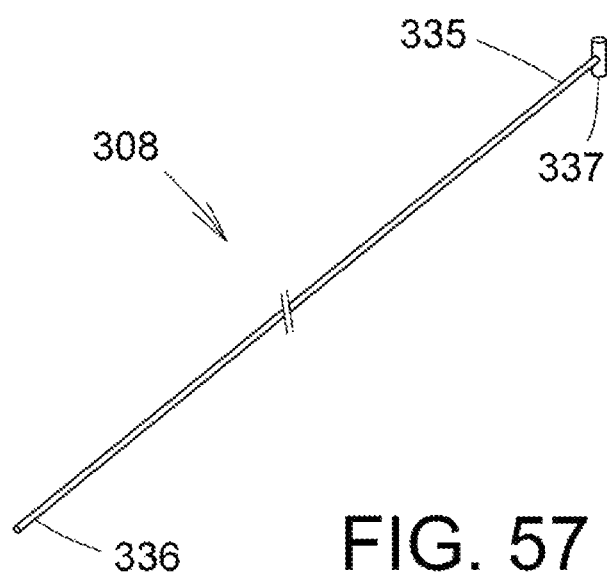
FIG. 57 is a perspective view of a spacer base control link according to an embodiment of the present invention.
Figure 58:
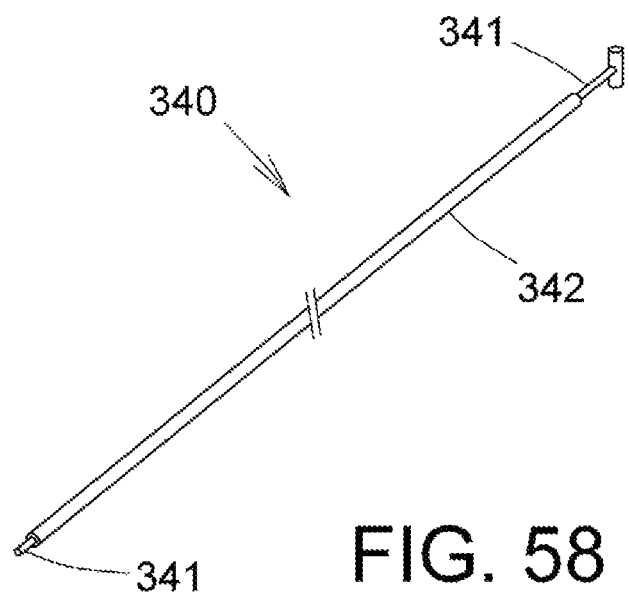
FIG. 58 is a perspective view of a spacer base control link according to another embodiment of the present invention.
Figure 59:
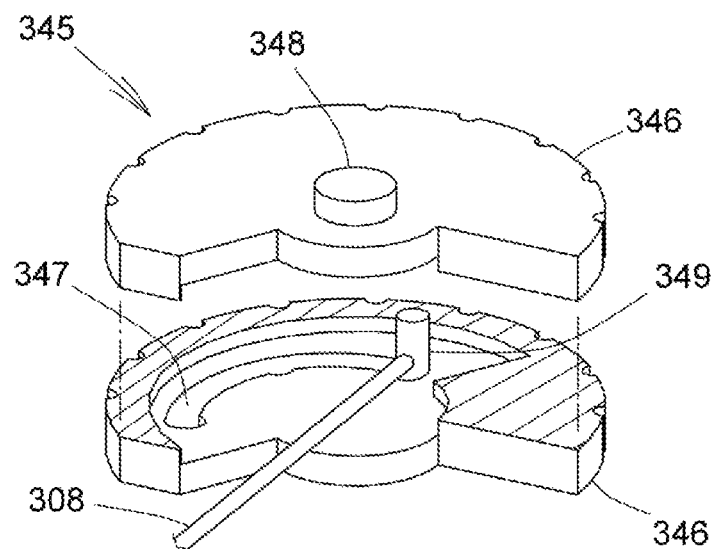
FIG. 59 is a perspective view of a spacer base control mechanism according to an embodiment of the present invention.

Referring to FIGS. 57 and 50, in an embodiment of the present invention, spacer base control link 308, having a proximal end 335 and a distal end 336, may be of any configuration and construction suitable for transfer of actuation force imparted thereto by a spacer base control mechanism 304, which will be described later in this Detailed Description. In an embodiment spacer base control link 308 may be selected from the group including at least one flexible wire, at least one rigid rod, at least one hydraulic or pneumatic line, at least one threaded rod, at least one rigid bar, at least one bar flexible lengthwise and a combination thereof with proximal and distal end 335, 336 of spacer base control link 308 configured to operably engage a spacer base control mechanism and a spacer base, respectively. For example, in an embodiment, proximal end 335 of spacer base control link 308 may be configured or terminated with a cam follower 337 to operably engage a spacer base control mechanism based on a cam driving mechanism, for example, as illustrated in FIG. 59. In an embodiment distal end 336 may be terminated with a force conversion mechanism before being operably joined with a spacer base, selected from the group including a screw on a threaded shaft, a worm gear drive, a rack and pinion gears, a crank mechanism and a cam drive mechanism, to convert a linear actuation force transferred via spacer base control link 308 to a rotational actuation force and vice versa, which is then applied to the spacer base. In an embodiment actuation force provided by a spacer base control mechanism that may be transferred by spacer base control link 308 may include a linear force, i.e., push and/or pull force, a rotational force or a fluid pressure. As shown in FIG. 58 spacer base control link 340 may comprise a core link element 341, for example, a flexible wire, a rigid rod, a threaded rod, a rigid bar, a bar flexible lengthwise housed in a tubular housing 342. Preferably, tubular housing 342 may be constructed to be able to maintain a constant length with two ends thereof fixedly joined with a spacer base control mechanism and a jaw member instrumented with a spacer assembly, for example, a compression gauge jaw member, respectively. In an embodiment tubular housing 342 may be flexible so that spacer base control link 340 may used in an elongated shaft with a bendable section comprising the surgical instrument of the present invention. In an alternate embodiment tubular housing 342 may be rigid.

Figure 60:
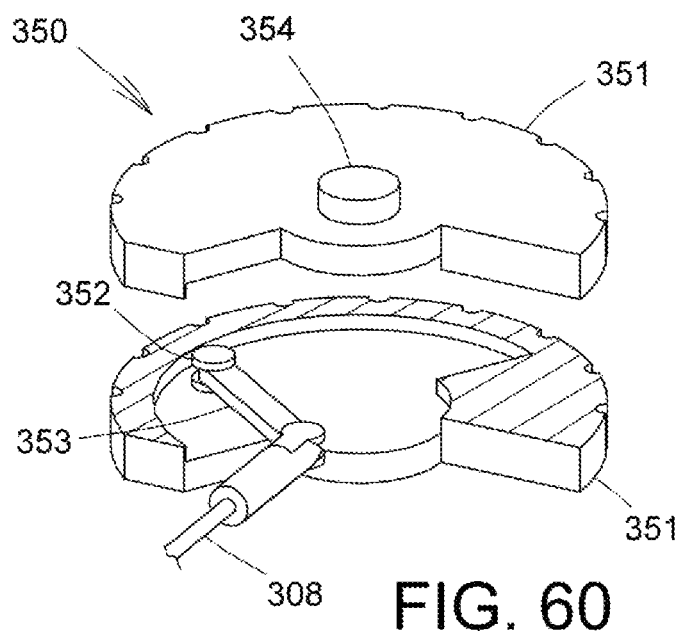
FIG. 60 is a perspective view of a spacer base control mechanism according to another embodiment of the present invention.
Figure 61:
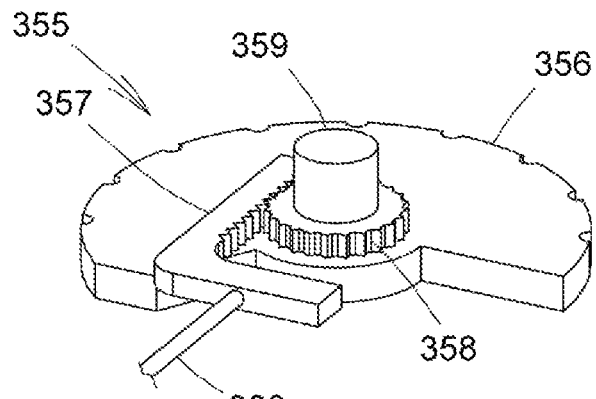
FIG. 61 is a perspective view of a spacer base control mechanism according to another embodiment of the present invention.

Referring to FIG. 59 showing in perspective view a spacer base control mechanism 345 based on a cam drive mechanism, sectioned and spaced apart, in an embodiment of the present invention, spacer base control mechanism 345 may comprise a thumbwheel 346 having a rotation axis 348 disposed substantially perpendicularly to the length direction of spacer base control link 308 and a cam groove 347 configured to receive a cam follower 349 of spacer base control link 308. In an embodiment cam groove 347 may be designed in such a way that rotation of thumbwheel 345 drives cam follower 349 linearly along the length of spacer base control link 308, which may be guided by guide member 310 as shown in FIG. 50. In an embodiment cam groove 347 may be designed to apply a pull force to spacer base control link 308 when rotated in a predetermined direction. In an embodiment cam groove 347 may be designed to apply a pull force to spacer base control link 308 when rotated in a predetermined direction and a push force in opposite direction. Referring to FIG. 60 showing in perspective view a spacer base control mechanism 350 based on a slider-crank mechanism, sectioned and spaced apart, in an alternate embodiment of the present invention, spacer base control mechanism 350 may comprise a thumbwheel 351 having a rotation axis 354 disposed substantially perpendicularly to the length direction of spacer base control link 308 and a crank 353 pivotally joined with a pivot 352 disposed on thumbwheel 351 on one end and spacer base control link 308 on the other end. In an embodiment pivot 352 may be disposed on thumbwheel 351 in such a way that rotation of thumbwheel 351 drives spacer base control link 308 linearly along the length thereof. In an embodiment pivot 352 may be disposed to apply a pull force to spacer base control link 308 when rotated in a predetermined direction. In an embodiment pivot 352 may be disposed to apply a pull force to spacer base control link 308 when rotated in a predetermined direction and a push force in opposite direction. Referring to FIG. 61 showing in perspective view a spacer base control mechanism 355 based on a rack and pinion gears, in an alternate embodiment of the present invention, spacer base control mechanism 355 may comprise a thumbwheel 356 having a rotation axis 359 disposed substantially perpendicularly to the length direction of spacer base control link 308, a pinion gear 385 disposed coaxially with rotation axis 359 and a rack gear 357 fixedly joined with spacer base control link 308. Spacer base control mechanism 355 is capable of providing a pull and push force to spacer base control link 308 depending on the direction of rotation of thumbwheel 356 effectively converting rotational actuation force to linear actuation force.

Figure 62:
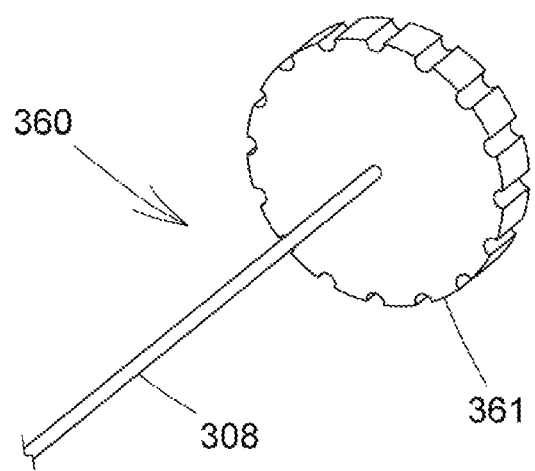
FIG. 62 is a perspective view of a spacer base control mechanism according to another embodiment of the present invention.
Figure 63:
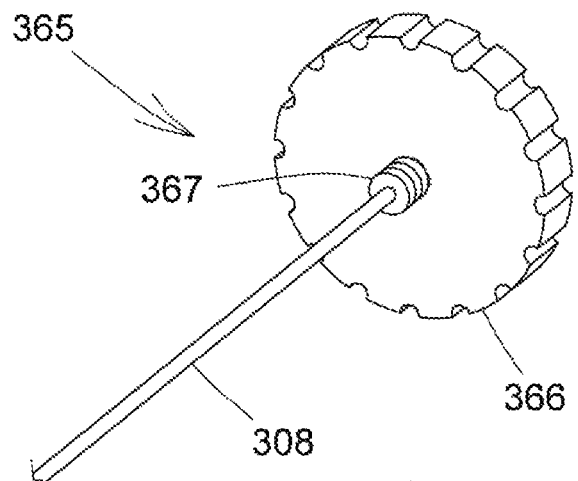
FIG. 63 is a perspective view of a spacer base control mechanism according to another embodiment of the present invention.
Figure 64:
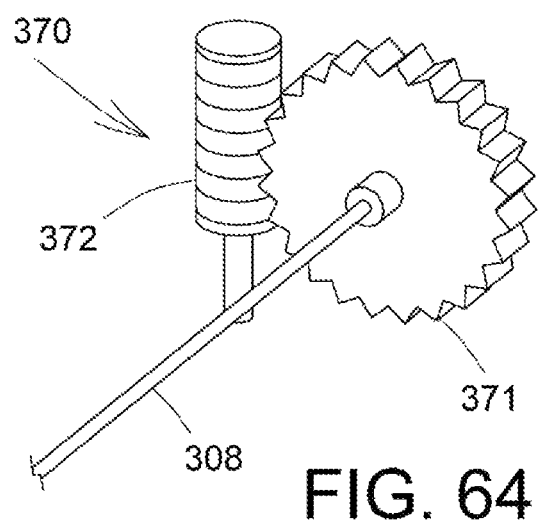
FIG. 64 is a perspective view of a spacer base control mechanism according to another embodiment of the present invention.

Referring to FIG. 62 showing in perspective view a spacer base control mechanism 360 based on a thumbwheel drive, in an embodiment of the present invention, spacer base control mechanism 360 may comprise a thumbwheel 361 with rotation axis disposed substantially in line with the length direction of spacer base control link 308 fixedly joined therewith. Rotation of thumbwheel 361 directly imparts a rotation actuation force to spacer base control link 308. Referring to FIG. 63 showing in perspective view a spacer base control mechanism 365 based on a screw drive, in an embodiment of the present invention, spacer base control mechanism 365 may comprise a thumbwheel 366 with rotation axis disposed substantially in line with the length direction of spacer base control link 308 and a threaded hole disposed coaxially therewith. In an embodiment spacer base control link 308 may be terminated with a threaded rod end 367 with thread matching that of thread hole in thumbwheel 366 to be mated therewith. Rotation of thumbwheel 366 causes a linear motion of spacer base control link 308 through threaded rod end 367. Referring to FIG. 64 showing in perspective view a spacer base control mechanism 370 based on a worm drive, in an embodiment of the present invention, spacer base control mechanism 370 may comprise a worm 372 and a worm gear 371 with rotation axis disposed in line with spacer base control link 308. Rotation of worm 372 causes worm gear 371 to rotate rotationally driving spacer base control link 308.

Figure 65:
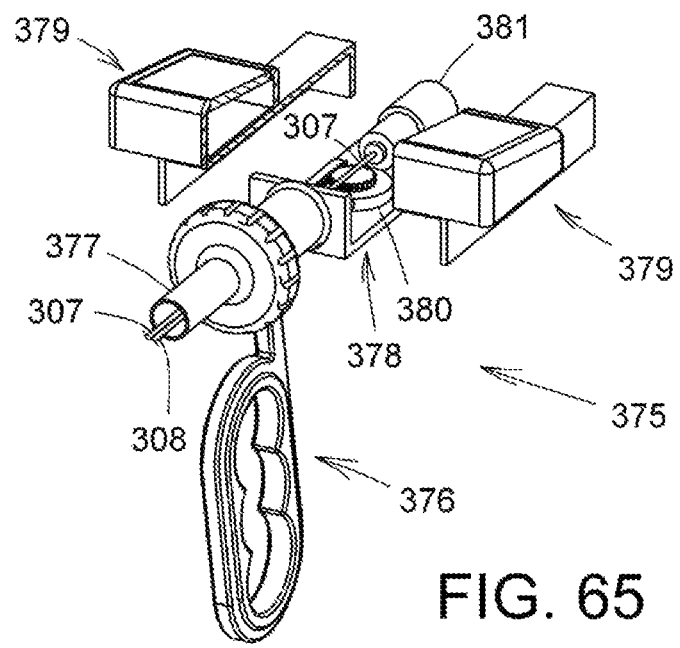
FIG. 65 is a perspective view of a power driven surgical instrument according to an embodiment of the present invention.

Referring to FIG. 65 showing, in an embodiment of the present invention, a surgical instrument 375 in perspective view, partially sectioned and spaced apart, for use in a surgical operation, surgical instrument 375 may comprise a handle 376, an elongated shaft 377 extending distally from handle 376 and having a proximal end and a distal end, an end effector (not shown in FIG. 65) supported by elongated shaft 377 at distal end thereof and controlled by end effector control link 307 configured to be driven by powered actuators, for example, by electrical motor, a spacer base control mechanism 378 configured to be driven by powered actuators, for example, by electrical motor to actuate spacer base control link 308, and a signal processor and display unit 379. In an embodiment of the present invention the powered actuators driving end effector control link 307 and spacer base control link 308 may be controlled by the CPU housed in signal processor and display unit 379, which also may process output signals from the force transducer from a compression gauge jaw member instrumented therewith and drive the display screen. In an embodiment signal processor and display unit 379 may be provided with programmable capabilities to coordinate controls of the end effector and the spacer base comprising the spacer base assembly with the results of processing of output signals from the force transducer.

Figure 66:
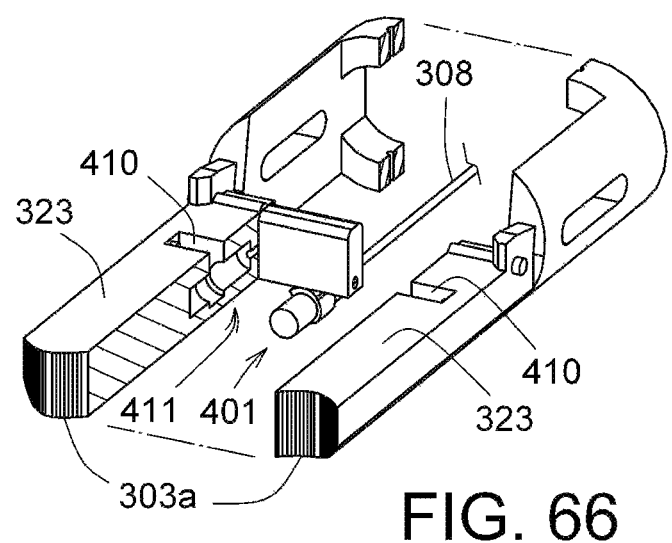
FIG. 66 is a perspective view of a compression gauge jaw member broken away and partially sectioned apart according to an embodiment of the present invention.
Figure 67:
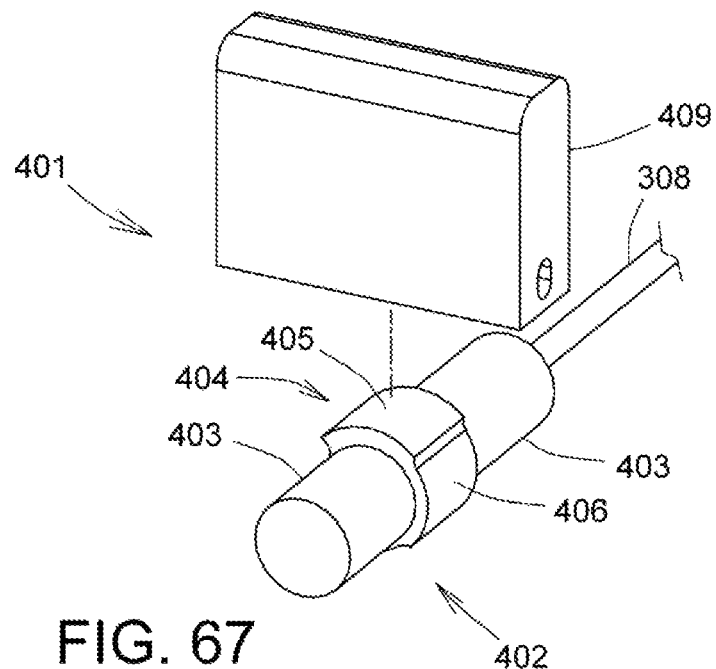
FIG. 67 is an exploded view of a spacer assembly according to an embodiment of the present invention.
Figure 68:
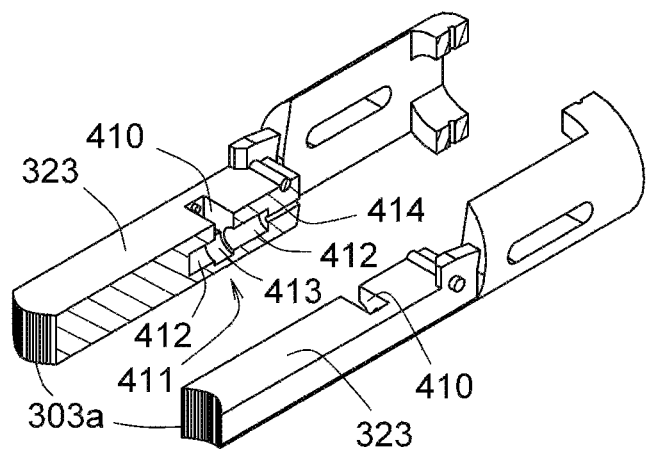
FIG. 68 is a perspective view of a compression gauge jaw member broken away and partially sectioned apart showing details of cavity for housing a spacer assembly according to an embodiment of the present invention.
Figure 69A:
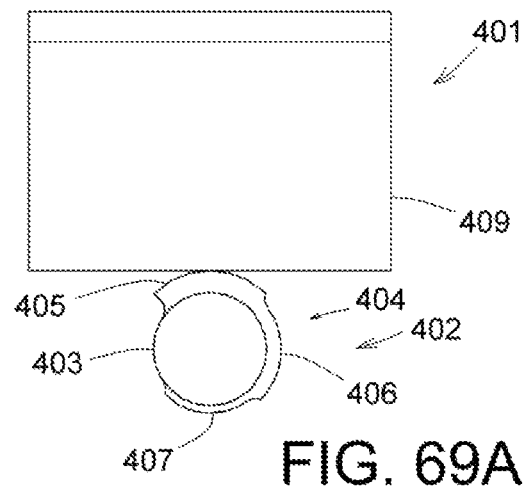
FIGS. 69A and 69B are front elevation views of a spacer assembly shown in FIG. 67 according to an embodiment of the present invention.
Figure 69B:
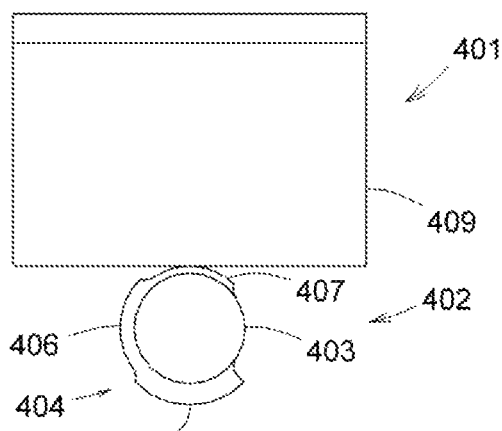
Figure 70:
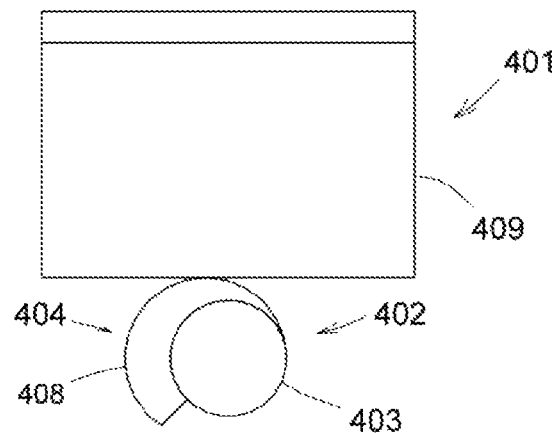
FIG. 70 is a front elevation view of a spacer assembly according to an alternate embodiment of the present invention.

In another practical implementation of a spacer assembly described previously with reference to FIGS. 21-24, FIG. 66 shows, in perspective view, a spacer assembly 401 disposed in a compression gauge jaw member 303a, shown partially broken away, sectioned and spaced apart, comprising an end effector comprising a surgical instrument in an embodiment of the present invention, and FIG. 67 shows, in perspective view, spacer assembly 401 in detail. As shown in FIG. 66, in an embodiment, compression gauge jaw member 303a may be configured to include a cavity 411, open to tissue supporting surface 323 thereof, for housing spacer assembly 401 configured to provide a rigid stop to maintain a predetermined gap distance or angular positional relationship between the anvil and compression gauge jaw member comprising the end effector. In an embodiment, as shown in detail in FIG. 67 in exploded view, and 69A and 69B in front elevation view, spacer assembly 401 may comprise a spacer member 409 of rigid construction, a spacer base 402, referred to as a stopper in describing FIGS. 21-24, of rigid construction. In an embodiment spacer base 402 may be configured as a cam shaft having an cylindrical axle 403 with an axis operatively joined with spacer base control link 308, and a cam 404 having a plurality of discrete cam action face 405, 406, 407, each at a discrete, predetermined distance from the axis of axle 403 and configured to support spacer member 409 thereon. Each cam action face 405, 406, 407 is configured to correspond to a discrete, predetermined height of spacer member 409 above tissue supporting surface 323 of jaw member 303a. In an alternate embodiment, as shown in FIG. 70, cam 404 may be configured to have a cam action face 408 with continuously varying distance from the axis of axle 403 to allow the height of spacer member 325 above tissue supporting surface 323 of jaw member 303a to be varied continuously. In another alternate embodiment cam 404 may be configured to have cam action faces with discretely and continuously varying distance from the axis of axle 403. Referring to FIG. 68 cavity 411 for housing spacer assembly 401 may be configured to comprise an axle portion 412 for receiving and supporting axle 403 under load from spacer member 409 while permitting free rotational motion thereof, a cam portion 413 for receiving cam 404 and a spacer member portion 410 open to the tissue supporting surface 323 of compression gauge jaw member 303a. A passage 414 for spacer base control link 308 may also be provided. In an embodiment of the present invention spacer member 409 and spacer member portion 410 of cavity 411 may be configured to allow spacer member 409 to move smoothly and substantially precisely in direction substantially perpendicular to tissue supporting surface 323 of jaw member 303a and axle portion 412 of cavity 411 to allow axle 403 to rotate smoothly and substantially precisely with the axis of axle 403 disposed substantially perpendicularly to the direction of motion of spacer member 409 and parallel to supporting surface 323 of jaw member 303a. In an embodiment spacer base control link 308 may be directly joined with and configured to transfer a rotational actuation force provided by a spacer base control mechanism in the handle of the surgical instrument, for example, as shown in FIG. 62 to drive spacer base 402 to rotate to adjust the height of spacer member 409 above tissue supporting surface 323 of jaw member 303a as illustrated in FIGS. 69A and 69B showing spacer base 402 in two different rotational positions.

Figure 71A:
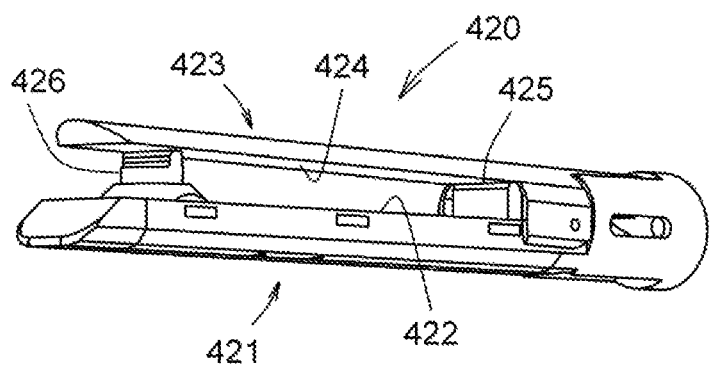
FIG. 71A is a perspective view of an end effector of a surgical compression gauge instrument according to an embodiment of the present invention.
Figure 71B:
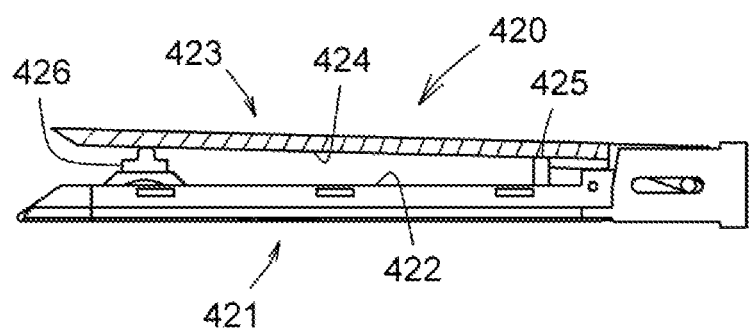
FIG. 71B is a side elevation view of an end effector shown in FIG. 70A with the anvil jaw member shown sectioned along the symmetry plane according to an embodiment of the present invention.

As previously described with reference to FIG. 13A, there are provided methods for calibrating the gap distance between the tissue compression face of the compression head comprising the force gauge assembly and the tissue contacting surface of the anvil jaw member in a surgical stapler instrument instrumented with a compression gauge cartridge or a surgical compression gauge instrument provide with an adjustable spacer member examples of which are shown in FIGS. 12A-12C. There are provided various embodiments of the present invention, described as follows, to facilitate calibration of the gap distance between the tissue compression face of the compression head comprising the force gauge assembly and the tissue contacting surface of the anvil jaw member in a surgical compression gauge instrument comprising a spacer assembly examples of which are shown in FIGS. 54 and 66. As shown in FIGS. 71A and 71B showing an end effector 420 comprising a compression gauge jaw member 421, having a tissue supporting surface 422 and a spacer assembly including spacer member 425, and an anvil jaw member 423 having a tissue contacting surface 424, in perspective view and side elevation view with anvil jaw member 423 sectioned away, respectively, and similarly to the methods described with reference to FIG. 13A, the calibration of the gap distance in a surgical compression gauge instrument comprising a spacer assembly involves initially positioning a reference block 426, of a height corresponding to a predetermined gap distance, between the tissue compression face of the compression head disposed in compression gauge jaw member 421 and tissue contacting surface 424 of anvil jaw member 423, and fully closing the two jaw members 421, 423 comprising end effector 420. If the height of spacer member 425 above tissue supporting surface 422 is less than the distance between tissue contacting surface 424 and tissue supporting surface 422 at the position of spacer member 425 a calibration of end effector 420 needs to be performed to bridge this difference so that spacer member 425 can provide the intended gap distance at the position of the compression head comprising the force gauge assembly between compression gauge jaw member 421 and anvil jaw member 423.

Figure 72:
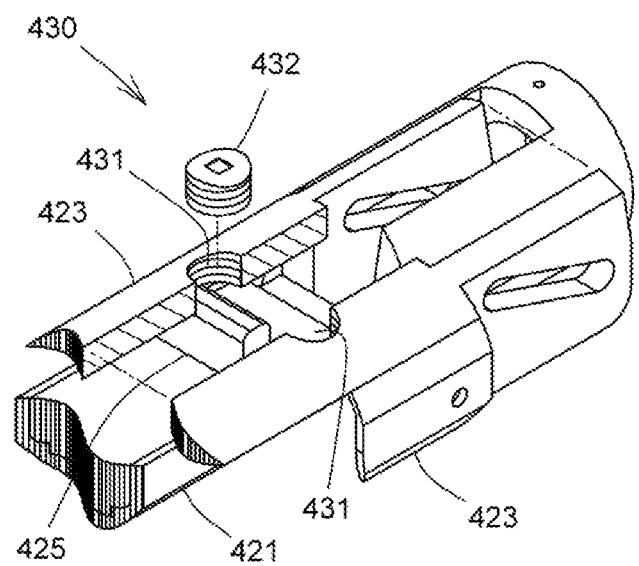
FIG. 72 is a perspective view of a compression gauge jaw member broken away and partially sectioned apart according to an embodiment of the present invention.
Figure 73:
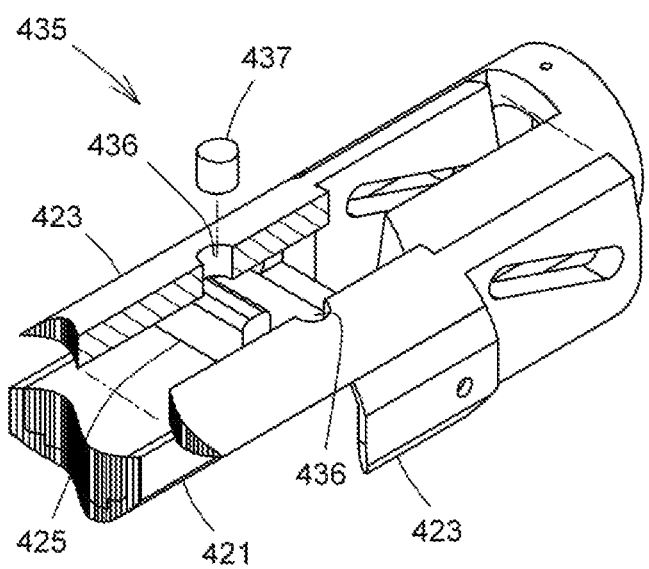
FIG. 73 is a perspective view of a compression gauge jaw member broken away and partially sectioned apart according to an embodiment of the present invention.
Figure 74A:
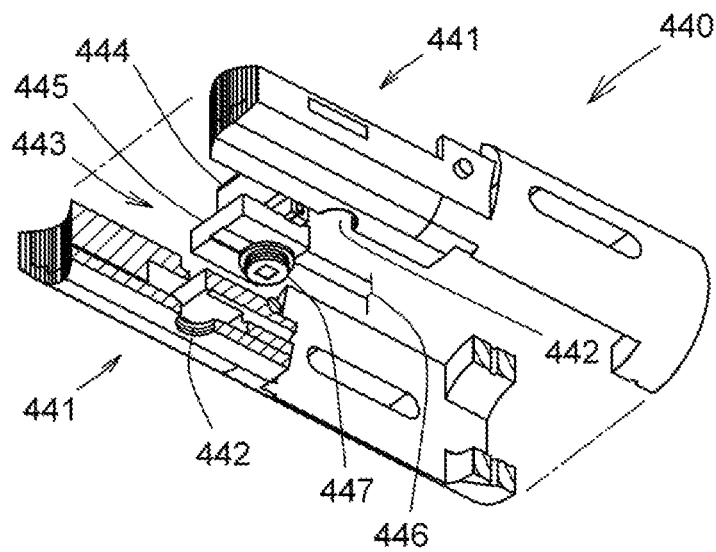
FIG. 74A is a perspective view of a compression gauge jaw member broken away and partially sectioned apart according to an embodiment of the present invention.
Figure 74B:
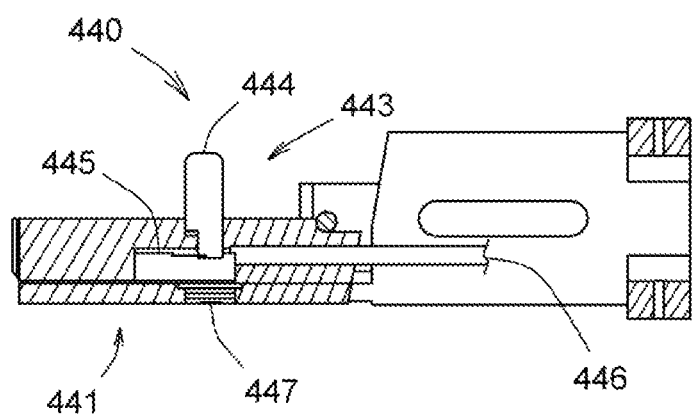
FIG. 74B is a side elevation view of a compression gauge jaw member broken away and partially sectioned apart shown in FIG. 74A according to an embodiment of the present invention.
Figure 75A:
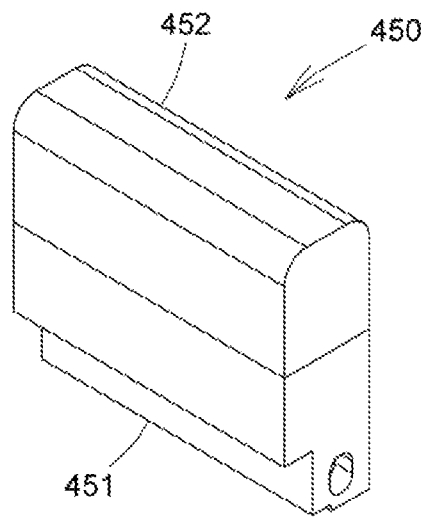
FIG. 75A is a perspective view of a spacer member according to an embodiment of the present invention.
Figure 75B:
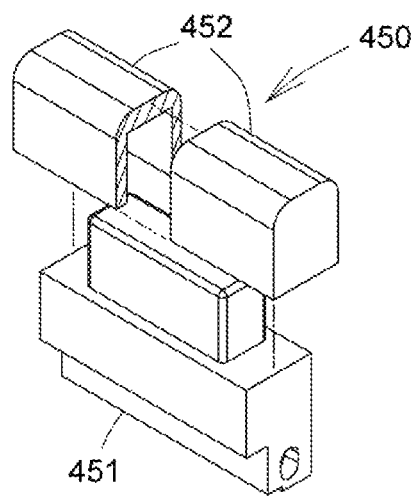
FIG. 75B is an exploded view of a spacer member shown in FIG. 75A partially sectioned apart according to an embodiment of the present invention.

Referring to FIG. 72 showing in perspective view, an end effector 430 comprising a compression gauge jaw member 421 and an anvil jaw member 423, partially broken away and anvil jaw member 423 sectioned and spaced apart, in an embodiment of the present invention calibration of end effector 430 may be performed with the use of a set screw 432 disposed in a threaded through hole 431 in anvil jaw member 423 at the position of spacer member 425 so that the position of set screw 432 may be adjusted by turning to fill the gap between tissue the contacting surface of anvil jaw member 423 and the anvil contacting face of spacer member 425. In an alternate embodiment, as shown in FIG. 73, calibration of end effector 435 may be performed with the use of a plug 437 press fitted into a through hole 436 in anvil jaw member 423 at the position of spacer member 425 so that the position of plug 437 may be adjusted to fill the gap between the tissue contacting surface of anvil jaw member 423 and the anvil contacting face of spacer member 425. In another alternate embodiment, as shown in FIGS. 74A and 74B showing a compression gauge jaw member 441 comprising an end effector 440 partially broken away, sectioned and spaced apart, and in side elevation view with compression gauge jaw member 441 sectioned, respectively, calibration of end effector 440 may be performed with the use of a set screw 447 disposed in a threaded through hole 442 disposed on the side of compression gauge jaw member 441 opposite the tissue supporting surface thereof at the position of spacer member 444 so that set screw 447 may be in contact with spacer base 445. During calibration the position of set screw 447 may be adjusted by turning to move spacer assembly 443, comprising spacer member 444, spacer base 445 and spacer base control link 446, toward the anvil jaw member to fill the gap between the tissue contacting surface of the anvil jaw member and the anvil contacting face of spacer member 444. In an alternate embodiment calibration of the end effector may be performed with the use of a plug press fitted into a smooth through hole disposed on the side of compression gauge jaw member 441 opposite the tissue supporting surface thereof at the position of spacer member 444 so that the plug may be in contact with spacer base 445. In another alternate embodiment calibration of the end effector may be performed with the use of a spacer member whose height can be adjusted to fill the gap between the tissue contacting surface of the anvil jaw member and the anvil contacting face of spacer member 444. Shown in FIGS. 75A and 75B are an exemplary embodiment of a spacer member 450 shown in perspective view, and exploded and partially sectioned view, respectively, comprising a body portion 451 and an interchangeable cap portion 452 configured to be securely fitted with each other. Cap portion 452 may be interchanged as needed during calibration of the end effector comprising spacer member 450 with another one having a dimension required to fill the gap between the tissue contacting surface of the anvil jaw member and the anvil contacting face of spacer member 450.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

While preferred illustrative embodiments of the invention are described above, it will be apparent to those skilled in the art that various changes and modifications may be made therein without departing from the invention. Accordingly, the appended claims should be used to interpret the scope of the present invention.

What is claimed is:
1. A surgical compression gauge instrument comprising:
  a handle portion;
  a body portion extending distally from said handle portion; and
  a tool assembly extending distally from and operatively connected to said body portion, comprising:
  a first jaw member;
  a second jaw member movable relative to said first jaw member, wherein said second jaw member is movable between an open position and a closed position defined by a gap distance between said first jaw member and said second jaw member;
  a force gauge assembly comprising a force transducer and a compression head; and
  a spacer assembly supported by said first jaw member comprising:
  an adjustable spacer member movable relative to said first jaw member; and
  a stopper, wherein said stopper is configured and disposed to provide a rigid stop to said adjustable spacer member at a predetermined position relative to said first jaw member,
  wherein said adjustable spacer member is configured to rigidly constrain said motion of said second jaw member relative to said first jaw member,
  wherein said gap distance between said first jaw member and said second jaw member in said closed position is adjustably determined by said predetermined position and configuration of said adjustable spacer member relative to said first jaw member.

2. The surgical compression gauge instrument of claim 1, wherein said first jaw member comprises a compression gauge jaw member and said second jaw member comprises an anvil jaw member.

3. The surgical compression gauge instrument of claim 1, wherein said stopper is of a configuration for holding said adjustable spacer member at a predetermined position relative to said first jaw member.

4. The surgical compression gauge instrument of claim 1, wherein said stopper is of a stepped configuration for discretely adjusting said position of said adjustable spacer member relative to said first jaw member.

5. The surgical compression gauge instrument of claim 1, wherein said stopper of a sloped configuration for continuously adjusting said position of said adjustable spacer member relative to said first jaw member.

6. The surgical compression gauge instrument of claim 1, wherein said spacer assembly is supported in a cavity, comprising a spacer channel and a stopper channel, disposed in said first jaw member.

7. The surgical compression gauge instrument of claim 1, wherein said spacer assembly further comprises a spacer spring.

8. The surgical compression gauge instrument of claim 1, wherein said spacer assembly further comprises a stopper control link operatively joined with said stopper.

9. A surgical compression gauge instrument comprising:
a handle portion;
a body portion extending distally from said handle portion; and
a tool assembly extending distally from and operatively connected to said body portion, comprising:
a first jaw member;
a second jaw member movable relative to said first jaw member, wherein said second jaw member is movable between an open position and a closed position defined by a gap distance between said first jaw member and said second jaw member;
a force gauge assembly comprising a force transducer and a compression head; and
a spacer assembly supported by said first jaw member comprising:
an adjustable spacer member movable relative to said first jaw member; and
a stopper stack comprising a plurality of stoppers stacked on top of one another, wherein said stopper stack is configured and disposed to provide a rigid stop to said adjustable spacer member at a predetermined position relative to said first jaw member,
wherein said adjustable spacer member is configured to rigidly constrain said motion of said second jaw member relative to said first jaw member,
wherein said gap distance between said first jaw member and said second jaw member in said closed position is adjustably determined by said predetermined position and configuration of said adjustable spacer member relative to said first jaw member.

10. The surgical compression gauge instrument of claim 9, wherein each stopper comprising said stopper stack further comprises a stopper control link operatively joined therewith.

11. A surgical compression gauge instrument comprising:
a handle portion;
a body portion extending distally from said handle portion; and
a tool assembly extending distally from and operatively connected to said body portion, comprising:
a first jaw member;
a second jaw member movable relative to said first jaw member, wherein said second jaw member is movable between an open position and a closed position defined by a gap distance between said first jaw member and said second jaw member;
a force gauge assembly comprising a force transducer and a compression head; and
a spacer assembly supported by said first jaw member comprising:
an adjustable spacer member movable relative to said first jaw member; and
a threaded portion; and a thumb wheel with a threaded hole, wherein said threaded portion is disposed to rotatably engage said threaded hole of said thumb wheel and configured to provide a rigid stop to said adjustable spacer member at a predetermined position relative to said first jaw member,
wherein said adjustable spacer member is configured to rigidly constrain said motion of said second jaw member relative to said first jaw member,
wherein said gap distance between said first jaw member and said second jaw member in said closed position is adjustably determined by said predetermined position and configuration of said adjustable spacer member relative to said first jaw member.

12. A surgical compression gauge instrument comprising:
a handle portion;
a body portion extending distally from said handle portion; and
a tool assembly extending distally from and operatively connected to said body portion, comprising:
a first jaw member;
a second jaw member movable relative to said first jaw member, wherein said second jaw member is movable between an open position and a closed position defined by a gap distance between said first jaw member and said second jaw member;
a force gauge assembly comprising a force transducer and a compression head; and
a spacer assembly supported by said first jaw member comprising:
an adjustable spacer member movable relative to said first jaw member;
a spacer base comprising a cam shaft having a cylindrical axle with an axis; and a cam and configured to provide a rigid stop to said adjustable spacer member at a predetermined position relative to said first jaw member,
wherein said adjustable spacer member is configured to rigidly constrain said motion of said second jaw member relative to said first jaw member,
wherein said gap distance between said first jaw member and said second jaw member in said closed position is adjustably determined by said predetermined position and configuration of said adjustable spacer member relative to said first jaw member.

13. The surgical compression gauge instrument of claim 12, wherein said cam comprises a plurality of cam action face, each of said cam action face circumferentially disposed around said cylindrical axle at discrete, predetermined distance from said axis of said cylindrical axle for discretely adjusting said position of said adjustable spacer member relative to said first jaw member.

14. The surgical compression gauge instrument of claim 12, wherein said cam comprises a cam action face with continuously varying distance from said axis of said cylindrical axle for continuously adjusting said position of said adjustable spacer member relative to said first jaw member.

15. The surgical compression gauge instrument of claim 12, wherein said spacer assembly further comprises a spacer base control link operatively joined with said cylindrical axle of said cam shaft.

16. A surgical compression gauge instrument comprising:
a handle portion;
a body portion extending distally from said handle portion; and
a tool assembly extending distally from and operatively connected to said body portion, comprising:
a first jaw member having a tissue supporting surface;
a second jaw member having a tissue contacting surface and movable relative to said first jaw member, wherein said second jaw member is movable between an open position and a closed position defined by a gap distance between said first member and said second jaw member;
a force gauge assembly comprising a force transducer and a compression head; and
a spacer assembly supported by said first jaw member comprising:
an adjustable spacer member comprising:
a body portion having an anvil contacting face and of a predetermined height above said tissue supporting surface of said first jaw member; and
a cap portion of a predetermined dimension, wherein said cap portion is interchangeably disposed in contact with said body portion between said tissue contacting surface of said second jaw member and said anvil contacting face of said body portion to adjust said height of said body portion above said tissue supporting surface of said first jaw member; and
wherein said gap distance between said first jaw member and said second jaw member in said closed position is adjustably determined by said predetermined height of said body portion of said adjustable spacer member above said tissue supporting surface of said first jaw member and said dimension of said cap portion.

17. The surgical compression gauge instrument of claim 16, wherein said body portion of said adjustable spacer member is movable relative to said first jaw member and said spacer assembly further comprises a stopper, wherein said stopper is configured and disposed to provide a rigid stop to said body portion of said adjustable spacer member at an adjustably predetermined position relative to said first jaw member.

* * * * *